United States Patent [19]
Chang et al.

[11] Patent Number: 6,121,283
[45] Date of Patent: Sep. 19, 2000

[54] APO B-SECRETION/MTP INHIBITORY AMIDES

[75] Inventors: George Chang, Ivoryton; George Joseph Quallich, North Stonington, both of Conn.

[73] Assignee: Pfizer Inc, New York, N.Y.

[21] Appl. No.: 09/284,466

[22] PCT Filed: Nov. 3, 1997

[86] PCT No.: PCT/IB97/01368

§ 371 Date: Apr. 20, 1999

§ 102(e) Date: Apr. 20, 1999

[87] PCT Pub. No.: WO98/23593

PCT Pub. Date: Jun. 4, 1998

Related U.S. Application Data

[60] Provisional application No. 60/032,307, Nov. 27, 1996.

[51] Int. Cl.$^7$ .................. C07D 217/04; A61K 31/47
[52] U.S. Cl. ........................... 514/307; 546/139
[58] Field of Search .............. 546/139; 514/307

[56] References Cited

U.S. PATENT DOCUMENTS 4,022,900  5/1977  Mathison .................. 424/258

FOREIGN PATENT DOCUMENTS 0643057  2/1994  European Pat. Off. .
9626205  8/1996  WIPO .
9640640  12/1996  WIPO .

*Primary Examiner*—Zinna Northington Davis

*Attorney, Agent, or Firm*—Peter C. Richardson; Gregg C. Benson; Carl J. Goddard

[57] ABSTRACT

This invention is directed to compounds of formula (I) or the stereoisomers, pharmaceutically acceptable salts and hydrates thereof. The compounds are Apo B/MTP inhibitors and are useful in the treatment of various disorders and conditions such as atherosclerosis, pancreatitis, obesity, hypercholesteremia, hypertriglyceridemia, hyperlipidemia, and diabetes. The compounds of this invention are also useful in combination with other pharmaceutical agents including cholesterol biosynthesis inhibitors and cholesterol absorption inhibitors, especially HMG-CoA reductase inhibitors and HMG-CoA synthase inhibitors; HMG-CoA reductase gene expression inhibitors; CETP inhibitors; bile acid sequestrants; fibrates; cholesterol absorption inhibitors; ACAT inhibitors, squalene synthetase inhibitors, ion-exchange resins, anti-oxidants and niacin. This invention is also directed to intermediates and processes useful in the preparation of compounds of formula (I)

56 Claims, No Drawings

APO B-SECRETION/MTP INHIBITORY AMIDES

CROSS-REFERENCE TO RELATED APPLICATIONS

This application is the National Stage filing under 35 U.S.C. §371 based on PCT/IB97/01368, filed internationally on Nov. 3, 1997, which claims priority from U.S. Provisional Application No. 60/032,307, filed Nov. 27, 1996.

FIELD OF THE INVENTION

This invention relates to compounds which are inhibitors of microsomal triglyceride transfer protein (MTP) and/or apolipoprotein B (Apo B) secretion and which are, accordingly, useful for the prevention and treatment of atherosclerosis and its clinical sequelae, for lowering serum lipids, and in the prevention and treatment of related diseases. The invention further relates to pharmaceutical compositions comprising these compounds and to methods of treating atherosclerosis, obesity, and related diseases and/or conditions with said compounds, either alone or in combination with other medicaments, including lipid lowering agents. Further still, the invention relates to certain processes and intermediates related thereto which are useful in the preparation of the compounds of the instant invention.

BACKGROUND OF THE INVENTION

Microsomal triglyceride transfer protein catalyzes the transport of triglyceride, cholesteryl ester, and phospholipids and has been implicated as a putative mediator in the assembly of Apo B-containing lipoproteins, biomolecules which contribute to the formation of atherosclerotic lesions. Specifically, the subcellular (lumen of the microsomal fraction) and tissue distribution (liver and intestine) of MTP have led to speculation that it plays a role in the assembly of plasma lipoproteins, as these are the sites of plasma lipoprotein assembly. The ability of MTP to catalyze the transport of triglyceride between membranes is consistent with this speculation, and suggests that MTP may catalyze the transport of triglyceride from its site of synthesis in the endoplasmic reticulum membrane to nascent lipoprotein particles within the lumen of the endoplasmic reticulum.

Compounds which inhibit MTP and/or otherwise inhibit Apo B secretion are accordingly useful in the treatment of atherosclerosis and other conditions related thereto. Such compounds are also useful in the treatment of other diseases or conditions in which, by inhibiting MTP and/or Apo B secretion, serum cholesterol and triglyceride levels may be reduced. Such conditions may include, for example, hypercholesterolemia, hypertriglyceridemia, pancreatitis, and obesity; and hypercholesterolemia, hypertriglyceridemia, and hyperlipidemia associated with pancreatitis, obesity, and diabetes. For a detailed discussion, see for example, Wetterau et al., Science, 258, 999–1001, (1992), Wetterau et al., Biochem. Biophys. Acta., 875, 610–617 (1986), European patent application publication No. 0 584 446 A2, and European patent application publication No. 0 643 057 A1 the latter of which discloses certain compounds of the generic formulae

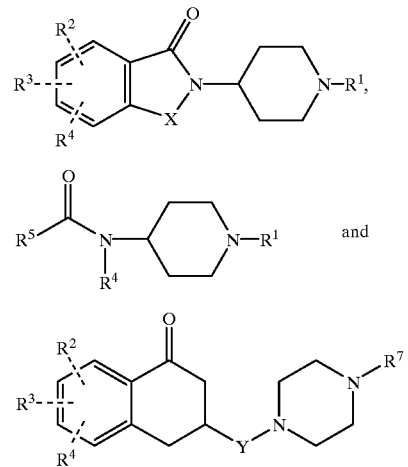

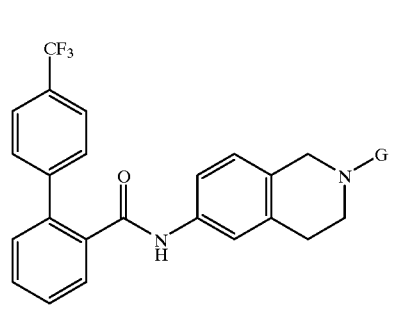

which have utility as inhibitors of MTP.

SUMMARY OF THE INVENTION

The instant invention relates to compounds which are Apo B-secretion/MTP inhibitors represented by the structural formula (I), including the stereoisomers and the pharmaceutically acceptable salts and hydrates thereof, (I)

wherein G is selected from:

(a) a phenyl or heterocyclic ring wherein said heterocyclic ring contains a total of from 3 to 14 ring atoms, wherein said heterocyclic ring incorporates a total of from 1 to 4 ring heteroatoms selected independently from oxygen, nitrogen, and sulfur, wherein the individual rings of said heterocyclic ring may be independently saturated, partially saturated or aromatic, and wherein each of said phenyl or heterocyclic rings may have optionally from 1 to 4 substituents selected independently from halogen, hydroxy, cyano, nitro, oxo, thioxo, aminosulfonyl, phenyl, phenoxy, phenylthio, benzyl, benzoyl, benzyloxy, $(C_1-C_{10})$alkyl, $(C_1-C_4)$ perfluoroalkyl, $(C_1-C_{10})$alkoxy, $(C_1-C_4)$ perfluoroalkoxy, $(C_1-C_{10})$alkoxycarbonyl, $(C_1-C_{10})$ alkylthio, $(C_1-C_{10})$alkylamino, di$(C_1-C_{10})$alkylamino, $(C_1-C_{10})$alkylaminocarbonyl, di$(C_1-C_{10})$ alkylaminocarbonyl, di$(C_1-C_{10})$alkylamino$(C_1-C_{10})$ alkoxy, $(C_1-C_{10})$acyl, $(C_1-C_{10})$perfluoroacyl, $(C_1-C_{10})$ acyloxy, $(C_1-C_{10})$acyloxy$(C_1-C_{10})$alkyl, $(C_1-C_6)$ acylamino and $(C_6-C_6)$perfluoroacylamino;

(b) —CH$_2$CN, (c) —CH 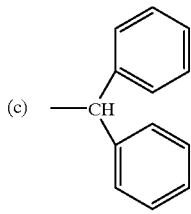

(d) (C$_2$–C$_{12}$)alkyl or (C$_2$–C$_{12}$)perfluoroalkyl wherein each of said (C$_2$–C$_{12}$)alkyl and (C$_2$–C$_{12}$)perfluoroalkyl is substituted optionally with from 1–3 substituents selected independently from:

(1) phenyl, halogen, nitro, cyano, hydroxy, —NR$^1$R$^2$, —OCOR$^3$, (C$_1$–C$_4$)alkoxy, (C$_1$–C$_4$)perfluoroalkoxy, (C$_1$–C$_4$)thioalkoxy or (C$_1$–C$_4$)perfluorothioalkoxy, where R$^1$ and R$^2$ in the definition of —NR$^1$R$^2$ are each selected independently from hydrogen, formyl, phenyl, benzyl, benzoyl, (C$_3$–C$_8$)cycloalkyl, (C$_3$–C$_8$)cycloalkenyl, (C$_1$–C$_4$)alkyl, (C$_1$–C$_4$)perfluoroalkyl, (C$_1$–C$_{10}$)alkoxycarbonyl, (C$_1$–C$_6$)acyl, (C$_1$–C$_6$)perfluoroacyl, aminocarbonyl, (C$_1$–C$_{10}$)alkylaminocarbonyl, di(C$_1$–C$_{10}$)alkylaminocarbonyl, aminosulfonyl, (C$_1$–C$_4$)alkylaminosulfonyl, di(C$_1$–C$_4$)alkylaminosulfonyl, (C$_1$–C$_4$)perfluoroalkylaminosulfonyl, (C$_1$–C$_4$)perfluoroalkylaminosulfonyl, di(C$_1$–C$_4$)alkylsulfonyl, and (C$_1$–C$_4$)perfluoroalkylsulfonyl, or where R$^1$ and R$^2$, taken together with the nitrogen atom to which they are attached, form a saturated, partially-saturated or aromatic heterocyclic ring, wherein said heterocyclic ring contains a total of from 3 to 14 ring atoms and incorporates optionally an additional 1 to 4 ring heteroatoms selected independently from oxygen, nitrogen and sulfur, wherein said heterocyclic ring may have optionally from 1 to 4 substituents selected independently from halogen, hydroxy, cyano, nitro, oxo, thioxo, aminosulfonyl, phenyl, phenoxy, phenylthio, benzyl, benzoyl, benzyloxy, (C$_1$–C$_{10}$)alkyl, (C$_1$–C$_4$)perfluoroalkyl, (C$_1$–C$_{10}$)alkoxy, (C$_1$–C$_4$)perfluoroalkoxy, (C$_1$–C$_{10}$)alkoxycarbonyl, (C$_1$–C$_{10}$)alkylthio, (C$_1$–C$_{10}$)alkylamino, di(C$_1$–C$_{10}$)alkylamino, (C$_1$–C$_{10}$)alkylaminocarbonyl, di(C$_1$–C$_{10}$)alkylaminocarbonyl, di(C$_1$–C$_{10}$)alkylamino(C$_1$–C$_{10}$)alkoxy, (C$_1$–C$_{10}$)acyl, (C$_1$–C$_{10}$perfluoroacyl (C$_1$–C$_{10}$)acylamino, (C$_1$–C$_{10}$)acyloxy, and (C$_1$–C$_{10}$)acyloxy, and (C$_1$–C$_{10}$)alkyl, where R$^3$ is selected from —NR$^1$R$^2$, phenyl, (C$_1$–C$_{10}$)alkyl, (C$_1$–C$_4$)perfluoroalkyl, (C$_1$–C$_6$)alkoxy and (C$_1$–C$_6$)perfluoroalkoxy, (2) (C$_3$–C$_8$)cycloalkyl or (C$_3$–C$_8$)cycloalkenyl wherein each of said (C$_3$–C$_8$)cycloalkyl and (C$_3$–C$_8$)cycloalkenyl may have optionally from 1 to 4 substituents selected independently from halogen, hydroxy, cyano, nitro, oxo, thioxo, aminosulfonyl, phenyl, phenoxy, phenylthio, benzyl, benzoyl, benzyloxy, (C$_1$–C$_{10}$)alkyl, (C$_1$–C$_4$)perfluoroalkyl, (C$_1$–C$_{10}$)alkoxy, (C$_1$–C$_4$)perfluoroalkoxy, (C$_1$–C$_{10}$)alkoxycarbonyl, (C$_1$–C$_{10}$)alkylthio, (C$_1$–C$_{10}$)alkylamino, di(C$_1$–C$_{10}$)alkylamino,(C$_1$–C$_{10}$)alkylaminocarbonyl, di(C$_1$–C$_{10}$)alkylaminocarbonyl, di(C$_1$–C$_{10}$)alkylamino (C$_1$–C$_{10}$)alkoxy, (C$_1$–C$_{10}$)acyl, (C$_1$–C$_{10}$)perfluoroacyl, (C$_1$–C$_{10}$)acylamino, (C$_1$–C$_{10}$)perfluoroacylamino, (C$_1$–C$_{10}$)acyloxy, and (C$_1$–C$_{10}$)acyloxy(C$_1$–C$_{10}$)alkyl, and (3) a saturated, partially-saturated or aromatic heterocyclic ring containing a total of from 3 to 14 ring atoms, wherein said heterocyclic ring incorporates a total of from 1 to 4 ring heteroatoms selected independently from oxygen, nitrogen and sulfur, wherein said heterocyclic ring may have optionally from 1 to 4 substituents selected independently from halogen, hydroxy, cyano, nitro, oxo, thioxo, aminosulfonyl, phenyl, phenoxy, phenylthio, benzyl, benzoyl, benzyloxy, (C$_1$–C$_{10}$)alkyl, (C$_1$–C$_4$)perfluoroalkyl, (C$_1$–C$_{10}$)alkoxy, (C$_1$–C$_4$)perfluoroalkoxy, (C$_1$–C$_{10}$)alkoxycarbonyl, (C$_1$–C$_{10}$)alkylthio, (C$_1$–C$_{10}$)alkylamino, di(C$_1$–C$_{10}$)alkylamio, (C$_1$–C$_{10}$)alkylaminocarbonyl, di(C$_1$–C$_{10}$)alkylaminocarbonyl, di(C$_1$–C$_{10}$)alkylamino (C$_1$–C$_{10}$)alkoxy, (C$_1$–C$_{10}$)acyl, (C$_1$–C$_{10}$)perfluoroacyl, (C$_1$–C$_{10}$)acylamino, (C$_1$–C$_{10}$)perfluoroacylamino, (C$_1$–C$_{10}$)acyloxy, and (C$_1$–C$_{10}$)acyloxy(C$_1$–C$_{10}$)alkyl, provided that (C$_2$–C$_{12}$)alkyl does not include unsubstituted allyl;

(e) (C$_3$–C$_8$)cycloalkyl or (C$_3$–C$_8$)cycloalkenyl wherein each of said (C$_3$–C$_8$)cycloalkyl and (C$_3$–C$_8$)cycloalkenyl may have optionally from 1 to 4 substituents selected independently from halogen, hydroxy, cyano, nitro, oxo, thioxo, aminosulfonyl, phenyl, phenoxy, phenylthio, benzyl, benzoyl, benzyloxy, (C$_1$–C$_{10}$)alkyl, (C$_1$–C$_4$)perfluoroalkyl, (C$_1$–C$_{10}$)alkoxy, (C$_1$–C$_4$)perfluoroalkoxy, (C$_1$–C$_{10}$)alkoxycarbonyl, (C$_1$–C$_{10}$)alkylthio, (C$_1$–C$_{10}$)alkylamino, di(C$_1$–C$_{10}$)alkylamino, (C$_1$–C$_{10}$)alkylaminocarbonyl, di(C$_1$–C$_{10}$)alkylaminocarbonyl, di(C$_1$–C$_{10}$)alkylamino(C$_1$–C$_{10}$)alkoxy, (C$_1$–C$_{10}$)acyl, (C$_1$–C$_{10}$)perfluoroacyl, (C$_1$–C$_{10}$)acylamino, (C$_1$–C$_{10}$)perfluoroacylamino, (C$_1$–C$_{10}$)acyloxy, and (C$_1$–C$_{10}$)acyloxy(C$_1$–C$_{10}$)alkyl; and (f) —(CH$_2$)$_n$COR$^4$, where R$^4$ is selected from hydroxy, phenyl, —NR$^1$R$^2$, (C$_1$–C$_4$)alkyl, (C$_1$–C$_4$)perfluoroalkyl, (C$_1$–C$_4$)alkoxy, (C$_1$–C$_4$)perfluoroalkoxy, (C$_3$–C$_8$)cycloalkyl, and (C$_3$–C$_8$)cycloalkenyl, where n is an integer from 1 to 4.

A preferred subgroup of the compounds of formula (I) and the stereoisomers, pharmaceutically acceptable salts and hydrates thereof, includes those compounds wherein G is selected from:

(a) a phenyl or heterocyclic ring wherein said heterocyclic ring contains a total of from 3 to 7 ring atoms, wherein said heterocyclic ring incorporates a total of from 1 to 4 ring heteroatoms selected independently from oxygen, nitrogen, and sulfur, wherein said heterocyclic ring may be saturated, partially saturated or aromatic, and wherein each of said phenyl or heterocyclic rings may each have optionally from 1 to 4 substituents selected independently from halogen, hydroxy, phenyl, benzyl, benzoyl, benzyloxy, (C$_1$–C$_{10}$)alkyl, (C$_1$–C$_4$)perfluoroalkyl, (C$_1$–C$_{10}$)alkoxy, (C$_1$–C$_4$)perfluoroalkoxy, (C$_1$–C$_{10}$)alkoxycarbonyl, (C$_1$–C$_{10}$)alkylthio, (C$_1$–C$_{10}$)alkylamio, di(C$_1$–C$_{10}$)alkylamino, (C$_1$–C$_{10}$)alkylaminocarbonyl, di(C$_1$–C$_{10}$)alkylaminocarbonyl, di(C$_1$–C$_{10}$)alkylamino(C$_1$–C$_{10}$)alkoxy, (C$_1$–C$_{10}$)acyl, (C$_1$–C$_{10}$)perfluoroacyl, (C$_1$–C$_6$)acylamino, (C$_1$–C$_6$)perfluoroacylamino, (C$_1$–C$_{10}$)acyloxy, and (C$_1$–C$_{10}$)acyloxy(C$_1$–C$_{10}$)alkyl;

(b) (C$_2$–C$_{12}$)alkyl wherein said (C$_2$–C$_{12}$)alkyl is substituted optionally with from 1–3 substituents selected from:

(1) phenyl, halogen, cyano, hydroxy, —NR$^1$R$^2$, —OCOR$^3$, (C$_1$–C$_4$)alkoxy, or (C$_1$–C$_4$)perfluoroalkoxy, where R$^3$ is selected from —NR$^1$R$^2$, (C$_1$–C$_4$)alkyl and (C$_1$–C$_4$)perfluoroalkyl, (2) (C$_3$–C$_6$)cycloalkyl or (C$_3$–C$_6$)cycloalkenyl wherein each of said (C$_3$–C$_6$)cycloalkyl and (C$_3$–C$_6$)cycloalkenyl may optionally have from 1 to 4 substituents selected independently from hydroxy, $(C_1-C_4)$alkyl, $(C_1-C_4)$alkoxy, and $(C_1-C_4)$alkoxycarbonyl, and (3) a saturated, partially-saturated or aromatic heterocyclic ring containing a total of from 3 to 6 ring atoms, wherein said heterocyclic ring incorporates a total of from 1 to 4 ring heteroatoms selected independently from oxygen, nitrogen and sulfur, wherein said heterocyclic ring may have optionally from 1 to 4 substituents selected independently from halogen, hydroxy, phenyl, benzyl, benzoyl, benzyloxy, $(C_1-C_{10})$alkyl, $(C_1-C_4)$perfluoroalkyl, $(C_1-C_{10})$alkoxy, $(C_1-C_{10})$alkoxycarbonyl, $(C_1-C_{10})$alkylthio, $(C_1-C_{10})$alkylamino, di$(C_1-C_{10})$alkylamino, $(C_1-C_{10})$alkylaminocarbonyl, di$(C_1-C_{10})$alkylaminocarbonyl, di$(C_1-C_{10})$alkylamino$(C_1-C_{10})$alkoxy, $(C_1-C_4)$perfluoroalkoxy, $(C_1-C_{10})$acyl, $(C_1-C_{10})$acylamino, $(C_1-C_{10})$perfluoroacylamino, $(C_1-C_{10})$acyloxy, and $(C_1-C_{10})$acyloxy$(C_1-C_{10})$alkyl;

provided that $(C_2-C_{12})$alkyl does not include unsubstituted allyl, (c) $(C_3-C_6)$cycloalkyl or $(C_3-C_6)$cycloalkenyl wherein each of said $(C_3-C_6)$cycloalkyl and $(C_3-C_6)$cycloalkenyl may have optionally from 1 to 4 substituents selected independently from hydroxy, $(C_1-C_4)$alkyl, $(C_1-C_4)$alkoxy, $(C_1-C_{10})$acylamino, $(C_1-C_{10})$perfluoroacylamino and $(C_1-C_4)$alkoxycarbonyl; and (d) —$(CH_2)_n COR^4$, where $R^4$ is selected from hydroxy, phenyl, —$NR^1R^2$, $(C_1-C_4)$alkyl, $(C_1-C_4)$perfluoroalkyl, $(C_1-C_4)$alkoxy, $(C_1-C_4)$perfluoroalkoxy, $(C_3-C_6)$cycloalkyl, and $C_3-C_6$ cycloalkenyl, where n is an integer from 1 to 4.

More particularly preferred of the compounds of formula (I) including the stereoisomers, pharmaceutically acceptable salts and hydrates thereof, are those compounds of the subgroup wherein G is selected from:

(a) $(C_2-C_{12})$alkyl, wherein said $(C_2-C_{12})$alkyl is substituted optionally with a group selected from phenyl, halogen, cyano, hydroxy, $(C_1-C_4)$alkoxy, or a saturated, partially-saturated or aromatic heterocyclic ring selected from thienyl, pyrazolyl, pyrrolidinyl, pyrrolyl, furanyl, thiazolyl, isoxazolyl, imidazolyl, triazolyl, tetrahydropyranyl, pyridyl, and pyrimidyl, wherein each of said heterocyclic rings may have optionally from 1 to 3 substitutents selected independently from halogen, $(C_1-C_4)$acyl, $(C_1-C_4)$perfluoroacyl, $(C_1-C_4)$alkyl, $(C_1-C_4)$perfluoroalkyl $(C_1-C_4)$alkoxy, $(C_1-C_4)$alkylaminocarbonyl, and $(C_1-C_4)$acylamino;

provided that $(C_2-C_{12})$alkyl does not include unsubstituted allyl;

(b) —$(CH_2)_n NR^1R^2$, where n is an integer from 2 to 4; and (c) —$(CH_2)_n COR^4$, where n is 1 or 2.

The following compounds of formula (I), including the stereoisomers and the pharmaceutically acceptable salts and hydrates thereof, listed hereinbelow together with their corresponding IUPAC chemical names, are especially preferred wherein G is selected from:

—$CH_2COOH$,
{6-[(4'-Trifluoromethylbiphenyl-2-carbonyl)-amino]-3,4-dihydro-1H-isoquinolin-2-yl}-acetic acid;

—$(CH_2)_4CH_3$,
4'-Trifluoromethylbiphenyl-2-carboxylic acid-(n-pentyl-1,2,3,4-tetrahydroisoquinolin-6-yl)-amide;

—$(CH_2)_3OCH_3$,
4'-Trifluoromethylbiphenyl-2-carboxylic acid-[2-(3-methoxypropyl)-1,2,3,4-tetrahydroisoquinolin-6-yl]-amide;

—$(CH_2)_2OCH_3$,
4'-Trifluoromethylbiphenyl-2-carboxylic acid-[2-(2-methoxyethyl)-1,2,3,4-tetrahydroisoquinolin-6-yl]-amide;

—$(CH_2)_2OCH_2CH_3$,
4'-Trifluoromethylbiphenyl-2-carboxylic acid-[2-(2-ethoxyethyl)-1,2,3,4-tetrahydroisoquinolin-6-yl]-amide;

—$(CH_2)_2CN$,
4'-Trifluoromethylbiphenyl-2-carboxylic acid-[2-(2-cyanoethyl)-1,2,3,4-tetrahydroisoquinolin-6-yl]-amide;

—$(CH_2)_2OCOCH_3$,
Acetic acid 2-{6-[(4'-trifluoromethylbiphenyl-2-carbonyl)-amino]-3,4-dihydro-1H-isoquinolin-2-yl}-ethyl ester;

—$(CH_2)_2OCON(CH_3)_2$,
Dimethylcarbamic acid 2-{6-[(4'-trifluoromethylbiphenyl-2-carbonyl)-amino]-3,4-dihydro-1H-isoquinolin-2-yl}ethyl ester;

—$(CH_2)_2NH_2$,
4'-Trifluoromethylbiphenyl-2-carboxylic acid-[2-(2-aminoethyl)-1,2,3,4-tetrahydroisoquinolin-6-yl]-amide;

—$(CH_2)_2NHCOCH_3$,
4'-Trifluoromethylbiphenyl-2-carboxylic acid-[2-(2-acetylaminoethyl)-1,2,3,4-tetrahydroisoquinolin-6-yl]-amide;

—$(CH_2)_2CON(CH_3)_2$,
4'-Trifluoromethylbiphenyl-2-carboxylic acid-[2-(2-dimethylcarbamoylethyl)-1,2,3,4-tetrahydroisoquinolin-6-yl]-amide;

—$CH_2CON(CH_3)_2$,
4'-Trifluoromethylbiphenyl-2-carboxylic acid-(2-dimethylcarbamoylethyl-1,2,3,4-tetrahydroisoquinolin-6-yl)-amide;

—$CH_2CON(CH_2CH_3)_2$,
4'-Trifluoromethylbiphenyl-2-carboxylic acid-(2-diethylcarbamoylethyl-1,2,3,4-tetrahydroisoquinolin-6-yl)-amide;

—$(CH_2)_2NHS(O)_2CH_3$,
4'-Trifluoromethylbiphenyl-2-carboxylic acid-[2-(2-methanesulfonylaminoethyl)-1,2,3,4-tetrahydroisoquinolin-6-yl]-amide;

—$(CH_2)_2NHCOCF_3$,
4'-Trifluoromethylbiphenyl-2-carboxylic acid-{2-[2-(2,2,2-trifluoroacetylamino)-ethyl]-1,2,3,4-tetrahydroisoquinolin6-yl}-amide;

—$(CH_2)_2NHCOCH_2CH_3$,
4'-Trifluoromethylbiphenyl-2-carboxylic acid-[2-(2-propionylaminoethyl)-1,2,3,4-tetrahydroisoquinolin-6-yl]-amide;

—$(CH_2)_2NHCOOCH_3$,
(2-{6-[4'-Trifluoromethylbiphenyl-2-carbonyl)-amino]-3,4-dihydro-1H-isoquinolin-2-yl}ethyl)carbamic acid methyl ester;

—$(CH_2)_2NHCHO$,
4'-Trifluoromethylbiphenyl-2-carboxylic acid-[2-(2-formylaminoethyl)-1,2,3,4-tetrahydroisoquinolin-6-yl]-amide;

—$(CH_2)_2NHCONHCH_3$,
4'-Trifluoromethylbiphenyl-2-carboxylic acid-{2-[2-(3-methylureido)-ethyl]-1,2,3,4-tetrahydroisoquinolin-6-yl}-amide;

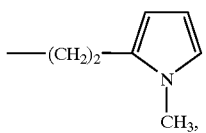

4'-Trifluoromethylbiphenyl-2-carboxylic acid-{2- [2-(1-methyl-1H-pyrrol-2-yl)ethyl]-1,2,3,4-tetrahydroisoquinolin-6-yl}-amide;

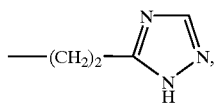

4'-Trifluoromethylbiphenyl-2-carboxylic acid-{2-[2-(2H-[1,2,4]triazol-3-yl-ethyl]-1,2,3,4-tetrahydroisoquinolin-6-yl}-amide;

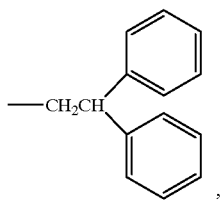

4'-Trifluoromethylbiphenyl-2-carboxylic acid-[2-(2,2-diphenylethyl)-1,2,3,4-tetrahydroisoquinolin-6-yl]-amide;

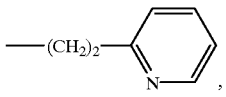

4'-Trifluoromethylbiphenyl-2-carboxylic acid-[2-(2-pyridin-2-yl-ethyl-1,2,3,4-tetrahydroisoquinolin-6-yl]-amide;

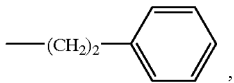

4'-Trifluoromethylbiphenyl-2-carboxylic acid-(2-phenylethyl-1,2,3,4-tetrahydroisoquinolin-6-yl)-amide;

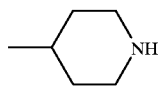

4'-Trifluoromethylbiphenyl-2-carboxylic acid-(2-piperidin-4-yl-1,2,3,4-tetrahydroisoquinolin-6-yl)-amide; and

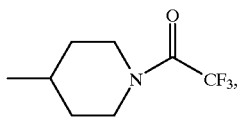

4'-Trifluoromethylbiphenyl-2-carboxylic acid-[2-(1-trifluoromethylacetyl-piperidin-4-yl)-1,2,3,4-tetrahydroisoquinolin-6-yl]-amide.

The following selected functional group definitions and examples thereof are employed throughout the instant specification and the appendant claims and are offered by way of illustration, and not by limitation.

The term "acyl" refers to either a straight or branched chain hydrocarbon moiety attached to a carbonyl group. Representative of such radicals are acetyl, propionyl, butyryl, and isobutyryl, and the like.

Term "alkyl" includes both straight and branched chain hydrocarbon radicals, having optional unsaturation in the form of double or triple-bonded carbon atoms. Representative of such radicals are methyl, ethyl, propyl, propylene, propynyl, isopropyl, isopropylene, butyl, isobutyl, isobutylene, tert-butyl, pentyl, hexyl, and so forth.

The term "alkoxy" includes a straight or branched chain hydrocarbon radical attached to an oxygen atom. Illustrative of such radicals are methoxy, ethoxy, propoxy, isopropoxy, butoxy, isobutoxy, pentoxy, hexoxy, heptoxy, and the like.

Reference to the term "halogen" is inclusive of fluorine, chlorine, bromine, and iodine unless noted otherwise.

The term "perfluoro", when used in conjunction with a specified hydrocarbon radical, is meant to include a substituent wherein the individual hydrogen atoms thereof may be substituted therefor with one or more and preferably from 1 to 9 fluorine atoms. Exemplary of such radicals are trifluoromethyl, pentafluoroethyl, heptafluoropropyl and the like.

Illustrative values for the term "$(C_1-C_{10})$alkoxycarbonyl" include methoxycarbonyl, ethoxycarbonyl, propoxycarbonyl, isopropoxycarbonyl, butoxycarbonyl, and the like.

Illustrative values for the term "$(C_1-C_{10})$alkylthio" include the corresponding sulfur-containing congeners of the term "alkoxy" as defined hereinabove, including methylthio, ethylthio, propylthio, isopropylthio, butylthio, isobutylthio, pentylthio, hexylthio, heptylthio, and the like.

Illustrative values for the term "$(C_1-C_{10})$alkylamino" include methylamino, ethylamino, propylamino, isopropylamino, butylamino, isobutylamino, and so forth.

Illustrative values for the term "di$(C_1-C_{10})$alkylamino" include dimethylamino, diethylamino, dipropylamino, di-isopropylamino, and the like as well as N-methyl-N'-ethylamino, N-ethyl-N'-propylamino, N-propyl-N'-isopropylamino, and the like.

Illustrative values for the term "$(C_1-C_{10})$acyloxy" include acetyloxy, propionyloxy, butyryloxy, and the like and also include such radicals which incorporate a cyclic substituent such as benzoyloxy.

Illustrative values for the term "$(C_3-C_8)$cycloalkyl" include cyclopropyl, cyclobutyl, cyclopentyl, cyclohexyl, and the like.

Illustrative values for the term "$(C_3-C_8)$cycloalkenyl" include cyclopropenyl, cyclobutenyl, cyclopentenyl, cyclohexenyl, cycloheptenyl, and the like.

It is to be understood that the term "heterocyclic ring" as employed throughout the instant specification and appendant claims embraces heterocyclic radicals which may be either monocyclic and polycyclic in nature. Exemplary of monocyclic heterocyclic ring systems are radicals such as furanyl, thienyl, pyrazolyl, pyrrolidinyl, pyrrolyl, thiazolyl, isoxazolyl, imidazolyl, triazolyl, tetrahydropyranyl, pyridyl, pyrimidyl, and so forth. Exemplary of polycyclic heterocyclic ring systems are radicals such as indolyl, benzofuranyl, benzimidazolyl, quinolinyl, acridinyl, phthalazinyl, and the like.

It is to be understood further that if a carbocyclic or heterocyclic ring may be bonded or otherwise attached to a designated substrate, including compound (I), through differing ring atoms without denoting a specific point of attachment, then all possible points are intended, whether through a carbon atom or a trivalent nitrogen atom. For example, the term "pyridyl" means 2-, 3-, or 4-pyridyl, the term "thienyl" means 2-, or 3-thienyl, and so forth.

The terms "treating" or "treatment" as employed herein are meant to embrace prophylactic as well as disease-remitive treatment.

The instant invention further provides pharmaceutical compositions suitable for the treatment of conditions including atherosclerosis, pancreatitis, obesity, hypercholesterolemia, hypertriglyceridemia, hyperlipidemia and diabetes, which comprise a therapeutically effective amount of a compound of formula (I) shown and defined hereinabove, including the stereoisomers, pharmaceutically acceptable salts and hydrates thereof, in combination with a pharmaceutically acceptable carrier or diluent.

The compounds of the instant invention inhibit or decrease Apo B secretion, likely by the inhibition of MTP, although it may be possible that additional mechanisms are involved. The compounds are useful in treating any of the disease states or conditions in which Apo B, serum cholesterol, and/or triglyceride levels are elevated. Accordingly, the instant invention provides a method for inhibiting or decreasing Apo B secretion in a mammal in need thereof which comprises the administration of an Apo B secretion inhibiting or decreasing amount of a compound of formula (I) or a stereoisomer, pharmaceutically acceptable salt or hydrate thereof. The invention further provides a method of treating a condition selected from atherosclerosis, pancreatitis, obesity, hypercholesterolemia, hypertriglyceridemia, hyperlipidemia, and diabetes which comprises administering to a mammal, especially a human, in need of such treatment a therapeutically effective amount of compound (I) or a stereoisomer, pharmaceutically acceptable salt or hydrate thereof. A preferred subgroup of the conditions described hereinabove is atherosclerosis, obesity, hypercholesterolemia, hypertriglyceridemia, hyperlipidemia, and diabetes.

The compounds of this invention may be used in conjunction with other pharmaceutical agents, including other lipid lowering agents. Such agents include, for example, cholesterol biosynthesis inhibitors and cholesterol absorption inhibitors, especially HMG-CoA reductase inhibitors and HMG-CoA synthase inhibitors; HMG-CoA reductase gene expression inhibitors; CETP inhibitors; bile acid sequestrants; fibrates; cholesterol absorption inhibitors; ACAT inhibitors, squalene synthetase inhibitors, ion-exchange resins, anti-oxidants and niacin. In combination therapy treatment, the compounds of the instant invention and the other drug therapies may be administered to mammals (e.g. humans) by conventional methods.

Specific cholesterol absorption inhibitors and cholesterol biosynthesis inhibitors are described in detail hereinbelow. Additional cholesterol absorption inhibitors are known to those skilled in the art and are described, for example, in PCT WO 94/00480.

Any HMG-CoA reductase inhibitor may be employed as the second compound in the combination therapy aspect of the instant invention. The term HMG-CoA reductase inhibitor refers to a compound which inhibits the biotransformation of hydroxymethylglutaryl-coenzyme A to mevalonic acid as catalyzed by the enzyme HMG-CoA reductase. Such inhibition may be determined readily by one of skill in the art according to standard assays (e.g., Methods of Enzymology, 1981; 71: 455–509 and the references cited therein). A variety of these compounds are described and referenced hereinbelow. U.S. Pat. No. 4,231,938 (the disclosure of which is hereby incorporated by reference) discloses certain compounds isolated after cultivation of a microorganism belonging to the genus Aspergillus, such as lovastatin. Also, U.S. Pat. No. 4,444,784 (the disclosure of which is hereby incorporated by reference) discloses synthetic derivatives of the aforementioned compounds, such as simvastatin. Additionally, U.S. Pat. No. 4,739,073 (the disclosure of which is hereby incorporated by reference) discloses certain substituted indoles, such as fluvastatin. Further, U.S. Pat. No. 4,346,227 (the disclosure of which is hereby incorporated by reference) discloses ML-236B derivatives, such as pravastatin. In addition, EP 491,226 teaches certain pyridyldihydroxyheptenoic acids, such as rivastatin. Also, U.S. Pat. No. 4,647,576 (the disclosure of which is hereby incorporated by reference) discloses certain 6-[2-(substituted-pyrrol-1-yl)alkyl]-pyran-2ones such as atorvastatin. Other HMG-CoA reductase inhibitors will be known to those skilled in the art.

Any HMG-CoA synthase inhibitor may be used as the second compound in the combination therapy aspect of this invention. The term HMG-CoA synthase inhibitor refers to a compound which inhibits the biosynthesis of hydroxymethylglutaryl-coenzyme A from acetyl-coenzyme A and acetoacetyl-coenzyme A, catalyzed by the enzyme HMG-CoA synthase. Such inhibition may be determined readily by one of skill in the art according to standard assays (e.g., Methods of Enzymology, 1975; 35: 155–160 and Methods of Enzymology, 1985; 110: 19–26 and the references cited therein). A variety of these compounds are described and referenced hereinbelow. U.S. Pat. No. 5,120,729 (the disclosure of which is hereby incorporated by reference) discloses certain beta-lactam derivatives. U.S. Pat. No. 5,064,856 (the disclosure of which is hereby incorporated by reference) discloses certain spiro-lactone derivatives perpared by culturing the microorganism MF5253. U.S. Pat. No. 4,847,271 (the disclosure of which is hereby incorporated by reference) discloses certain oxetane compounds such as 11-(3hydroxymethyl-4-oxo-2-oxetayl)-3,5,7-trimethyl-2,4-undecadienoic acid derivatives. Other HMG-CoA synthase inhibitors will be known to those skilled in the art.

Any compound that decreases HMG-CoA reductase gene expression may be used as the second compound in the combination therapy aspect of this invention. These agents may be HMG-CoA reductase transcription inhibitors that block the transcription of DNA or translation inhibitors that prevent translation of mRNA coding for HMG-CoA reductase into protein. Such inhibitors may either affect transcription or translation directly, or may be biotransformed into compounds that have the aforementioned attributes by one or more enzymes in the cholesterol biosynthetic cascade or may lead to the accumulation of an isoprene metabolite that has the aforementioned activities. Such regulation is readily determined by those skilled in the art according to standard assays (Methods of Enzymology, 1985; 110: 9–19). Several such compounds are described and referenced below however other inhibitors of HMG-CoA reductase gene expression will be known to those skilled in the art U.S. Pat. No. 5,041,432 (the disclosure of which is incorporated herein by reference) discloses certain 15-substituted lanosterol derivatives. Other oxygenated sterois that suppress the biosynthesis of HMG-CoA reductase are discussed by E.I. Mercer (Prog. Up. Res., 1993; 32: 357–416).

Any compound having activity as a CETP inhibitor can serve as the second compound in the combination therapy aspect of the instant invention. The term CETP inhibitor refers to compounds which inhibit the cholesteryl ester transfer protein (CETP) mediated transport of various cholesteryl esters and triglycerides from high density lipoprotein (HDL) to low density lipoprotein (LDL) and very low density liprotein (VLDL). A variety of these compounds are described and referenced hereinbelow however other CETP inhibitors will be known to those skilled in the art U.S. Pat. No. 5,512,548 (the disclosure of which is incorporated herein by reference) discloses certain polypeptide derivatives having activity as CETP inhibitors, while certain CETP-inhibitory rosenonolactone derivatives and phosphate-containing analogs of cholesteryl ester are disclosed in J. Antibiot., 1996; 49(8): 815–816, and Bioorg. Med. Chem. Lett; 1996; 6: 1951–1954, respectively.

Any ACAT inhibitor can serve as the second compound in the combination therapy aspect of this invention. The term ACAT inhibitor refers to compounds which inhibit the intracellular esterification of dietary cholesterol by the enzyme acyl CoA:cholesterol acyltransferase. Such inhibition may be determined readily by one of skill in the art according to standard assays, such as the method of Heider et al. described in Journal of Lipid Research., 1983; 24: 1127. A variety of these compounds are described and referenced hereinbelow however other ACAT inhibitors will be known to those skilled in the art. U.S. Pat. No. 5,510,379 (the disclosure of which is incorporated by reference) discloses certain carboxysulfonates, while WO 96/26948 and WO 96/10559 both disclose urea derivatives having ACAT inhibitory activity.

Any compound having activity as a squalene synthetase inhibitor can serve as the second compound in the combination therapy aspect of the instant invention. The term squalene synthetase inhibitor refers to compounds that inhibit the condensation of two molecules of farnesylpyrophosphate to form squalene, a reaction that is catalyzed by the enzyme squalene synthetase. Such inhibition is readily determined by those skilled in the art according to standard methodology (Methods of Enzymology 1969; 15: 393–454 and Methods of Enzymology 1985; 110: 359–373 and references cited therein). A summary of squalene synthetase inhibitors has been complied (Curr. Op. Ther. Patents (1993) 861–4). European patent application publication No. 0 567 026 A1 discloses certain 4,1-benzoxazepine derivatives as squalene synthetase inhibitors and their use in the treatment of hypercholesterolemia and as fungicides. European patent application publication No. 0 645 378 A1 discloses certain seven- or eight-membered heterocycles as squalene synthetase inhibitors and their use in the treatment and prevention hypercholesterolemia and fungal infections. European patent application publication No. 0 645 377 A1 discloses certain benzoxazepine derivatives as squalene synthetase inhibitors useful for the treatment of hypercholesterolemia or coronary sclerosis. European patent application publication No. 0 611 749 A1 discloses certain substituted amino acid derivatives useful for the treatment of arteriosclerosis. European patent application publication No. 0 705 607 A2 discloses certain condensed seven- or eight-membered heterocyclic compounds useful as antihypertriglyceridemic agents. PCT publication WO96/09827 discloses certain combinations of cholesterol absorption inhibitors and cholesterol biosynthesis inhibitors including benzoxazepine derivatives and benzothiazepine derivatives. European patent application publication No. 0 071 725 A1 discloses a process for preparing certain optically-active compounds, including benzoxazepine derivatives, having plasma cholesterol and triglyceride lowering activities.

It will be appreciated by those skilled in the art that certain compounds of the instant invention may contain an asymmetrically-substituted carbon atom and accordingly may exist in, and/or be isolated in, optically-active and racemic forms. Furthermore, some compounds may exhibit polymorphism. It is to be understood that the present invention encompasses any and all racemic, optically-active, polymorphic and stereoisomeric forms, or mixtures thereof, which form or forms possess properties useful in the treatment of the conditions noted hereinabove, it being well known in the art how to prepare optically-active forms (for example, by resolution of the racemic form by recrystallization techniques, by synthesis from optically-active starting materials, by chiral synthesis, or by chromatographic separation using a chiral stationary phase) and how to determine efficacy for the treatment of the conditions noted herein by the standard tests described hereinafter.

DETAILED DESCRIPTION OF THE INVENTION

In the discussion which follows, certain common chemical and procedural abbreviations and acronyms therefor have been employed which include: Me (methyl); Et (ethyl); Bn (benzyl); THF (tetrahydrofuran); DMF (dimethylfornamide); BOC (tert-butyloxycarbonyl, a protecting group); DMAP (1,1'-dimethylaminopyridine), Ms (methanesulfonyl, mesyl); TFA (trifluoroacetic acid); Ac (acetyl); RP (reverse phase); HPLC (high performance liquid chromatography); TLC (thin layer chromatography).

The compounds of formula (I) are most conveniently synthesized by employing processes analogous to those known in the chemical arts for the production of similar compounds. Such processes for the manufacture of a compound of formula (I) as defined in detail hereinabove are provided as further features of the invention and are illustrated by the following procedures in which the meanings of generic radicals are as previously defined unless otherwise qualified. The processes involve coupling a compound of formula (II),

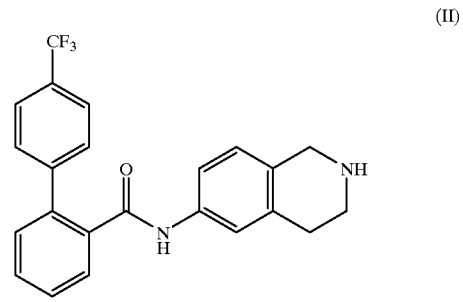

(II)

which contributes the "western" portion of the molecule, i.e the moiety consisting of formula (II) with the hydrogen removed from the tetrahydroisoquinolinyl ring nitrogen, with a reactant which adds the "eastern", i.e. —G moiety. Reactants which furnish the eastern moiety are generally commercially available or are well precedented in the chemical literature. The compound of formula (II) has the chemical name "4'-trifluoromethylbiphenyl-2-carboxylic acid-(1,2,3,4-tetrahydroisoquinolin-6-yl)-amide" and is referred to hereinafter as simply "compound (II)" for the sake of convenience. The western portion of the molecule which it contributes to the compounds of formula (I) is usually known as the 6-[(4'-trifluoromethyl)biphen-2-ylcarbonylamino]-3,4-dihydro-1H-isoquinolin-2-yl moiety, although less frequently, when named as a substitutent in a compound, this ring system may also be denoted as a 6-substituted "3,4-dihydro-1H-isoquinolin-2-yl" moiety.

An additional aspect of the instant invention provides for an acid addition salt of compound (II). The isoquinoline ring nucleus of compound (II) contains an isolated basic center and may therefore form an acid addition salt with various organic and inorganic conjugate acids. For purposes of the instant invention, the expression "acid addition salt" is intended to include but not be limited to such salts as the hydrochloride, hydrobromide, sulfate, hydrogen sulfate, phosphate, hydrogen phosphate, dihydrogenphosphate, acetate, succinate, citrate, methanesulfonate (mesylate) and p-toluenesulfonate (tosylate) salts, as well as any hydrated or solvated forms thereof. Of these, the p-toluenesulfonate (tosylate) salt form is generally preferred.

The compound of formula (II) may be synthesized as outlined in Schemes 1–4 and detailed experimental descriptions of each of these methods is disclosed sequentially in Examples 1–4 hereinbelow. A further feature of the instant invention provides a preferred process including certain intermediates related thereto, for the preparation of compound (II) and this method is outlined hereinbelow in Scheme 4.

Referring now to Scheme 1,2-(4-bromophenyl) ethylamine hydrobromide is reacted with ethyl formate in the presence of a base to form N-[2-(4-bromophenyl)ethyl] formamide (1). The formamide derivative thus produced is then cyclized to the desired dihydroisoquinoline derivative (2) by treatment with phosphorus pentoxide in polyphosphoric acid. Treatment of the cyclized product with a hydrogen halide gas, (e.g., hydrogen chloride) forms the hydrogen halide salt of 7-bromo-3,4-dihydroisoquinoline. The hydrogen halide salt thus produced is then reduced to afford 7-bromo-1,2,3,-tetrahydroisoquinoline (3). The reduced product is then nitrated by treatment with potassium nitrate in concentrated sulfuric acid and the regioisomerically-pure nitrated fractions are separated to yield 7-bromo-6-nitro-1, 2,3,4-tetrahydroisoquinoline (4). The nitro compound (4) is then protected by functionalization of the tetrahydroisoquinoline ring nitrogen atom with an appropriate protecting group. Exemplary of such protecting groups for the nitrogen atom are benzyl and BOC groups respectively, however other protecting groups may also be employed depending upon other remote functionalities present in the molecule and the conditions of the preparative method involved. For a general description of protecting groups and their uses, see T. W. Greene, *Protective Groups in Organic Synthesis*, John Wiley & Sons, New York, 1991. The resulting N-protected tetrahydroisoquinoline product (5) is hydrogenated in the presence of palladium on calcium carbonate to form the corresponding 6-amino derivative (6). The amine thus formed is coupled with 4'-trifluoromethylbiphenyl-2-carboxylic acid or an activated form thereof to furnish the corresponding amide derivative (7). Examples of activated forms of carboxylic acids, as well as 4'-trifluoromethylbiphenyl-2-carboxylic acid, include the corresponding acid halide, an activated derivative which may be formed by reacting the free add with an appropriate, commercially-available carbodiimide, e.g., 1-(3-dimethylaminopropyl)-3-ethylcarbodiimide hydrochloride (EDC) or 1,1'-carbonyldiimidazole (CDI), as well as various other activated forms which will be recognized readily by those skilled in the art. If desired, the EDC may advantageously be polymer bound as disclosed in U.S. Pat. No. 5,416,193 (the disclosure of which is incorporated herein by reference). Additionally, the activated carboxylic acid is normally reacted in the presence of a suitable base, for example, an amine which may be polymer bound, such as polymer bound morpholino-polystyrene. The above method of activating carboxylic acids for coupling with appropriate substrates is not to be construed as being limited to the case of 4'-trifluoromethylbiphenyl-2-carboxylic acid, but may be applied equally to any carboxylic acid residue disclosed in the instant specification and the appendant claims. Conventional deprotection of the functionalized tetrahydroisoquinoline ring nitrogen atom of (7) then furnishes compound (II), 4'-trifluoromethylbiphenyl-2-carboxylic acid-(1,2,3,4-tetrahydroisoquinolin-6-yl)-amide.

Alternatively, compound (II) may be synthesized by a second route as outlined in Scheme 2. Referring now to Scheme 2,2-chloro-4-nitrobenzoic acid is treated with dimethyl malonate in the presence of base to form compound (8). Compound (8) may then be treated with aqueous alcoholic base to effect hydrolysis and decarboxylation to yield compound (9). Compound (9) may, if desired, be treated with acetic anhydride in toluene or other suitable solvent to furnish anhydride (10). Reduction of compound (9) or ringopening of compound (10) affords the corresponding diol (11) which is then cyclized by treatment with mesyl chloride followed by ammonia, thus affording compound (12). Compound (12) is then N-protected in a manner similar to that described in Scheme 1, to yield compound (13), which, in turn, is reduced to furnish amine (6). Amine (6) is then coupled with 4'-trifluoromethylbiphenyl-2-carboxylic acid or an activated form thereof as shown and described hereinabove in Scheme 1 to furnish the corresponding amide analog (7) of compound (II). Compound (7) is then N-deprotected as described previously to afford compound (II).

SCHEME 1

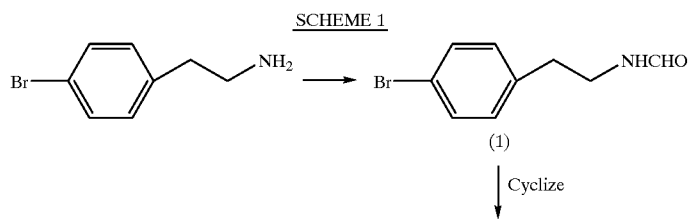

(1)

Cyclize

-continued
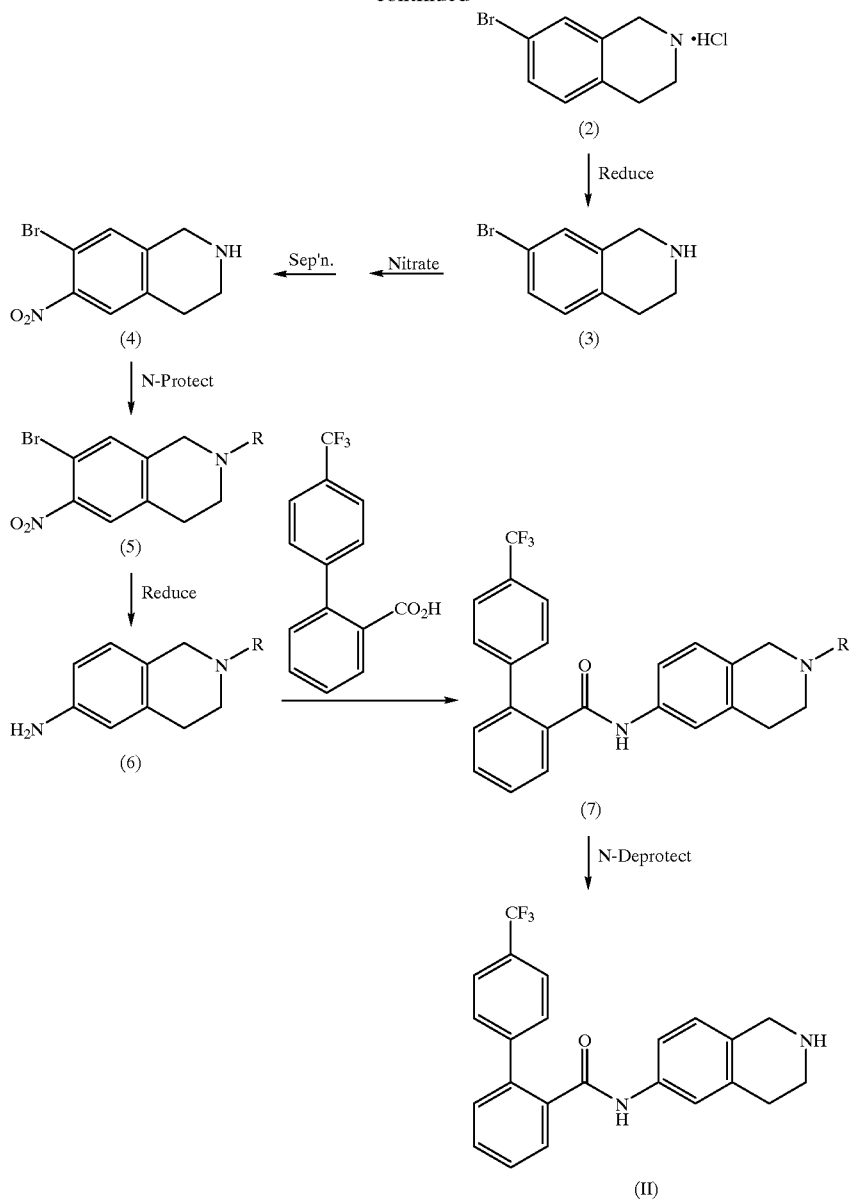
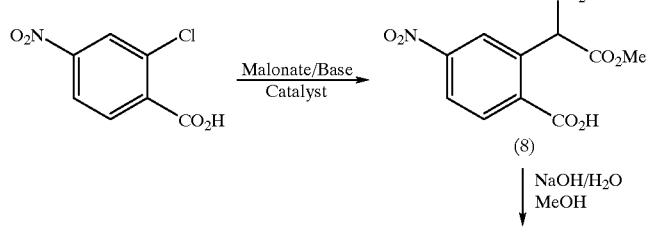
SCHEME 2

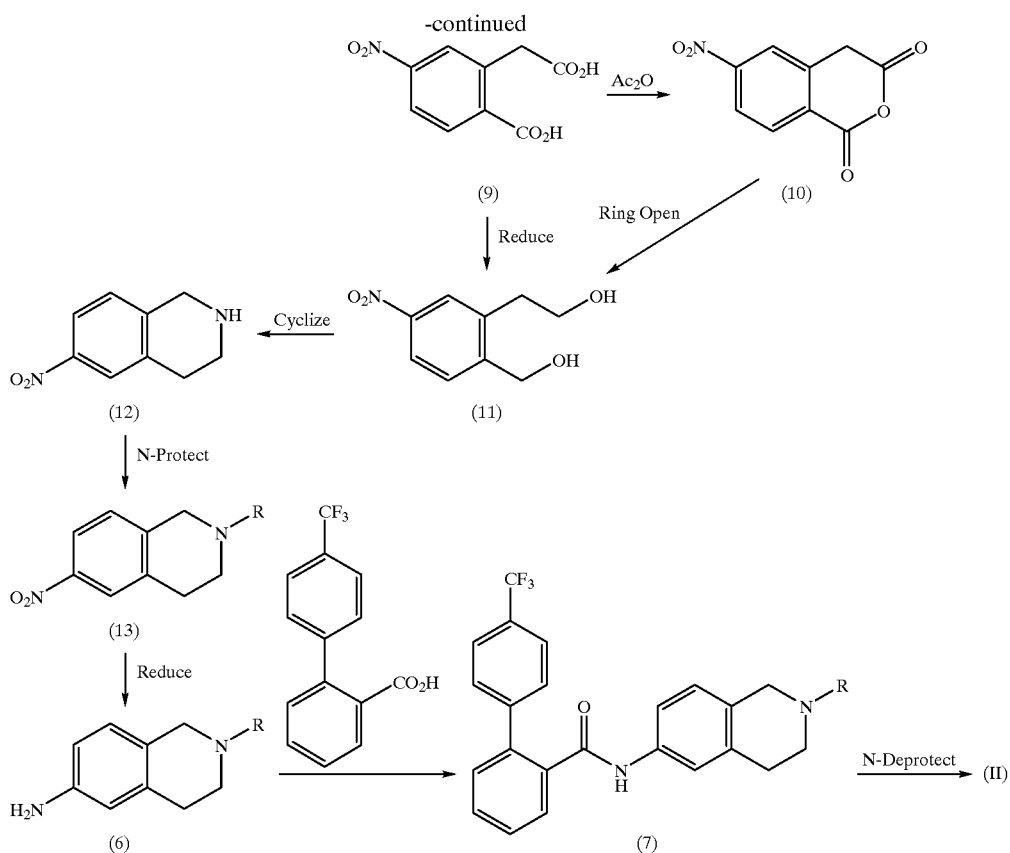

In an additional, alternative synthetic route, compound (II) may be synthesized as shown and described in Scheme 3. The nitro diol (11) from Scheme 2, is hydrogenated in the presence of a suitable catalyst, for example platinum on carbon, to form the corresponding amino diol (14). The diol so produced may then be reacted with 4'-trifluoromethylbiphenyl-2-carboxylic acid or an activated form thereof to afford amide (15). Cyclization of compound (15) with ammonia in the presence of a suitable catalyst in a manner similar to that shown and described in Scheme 2 furnishes compound (II).

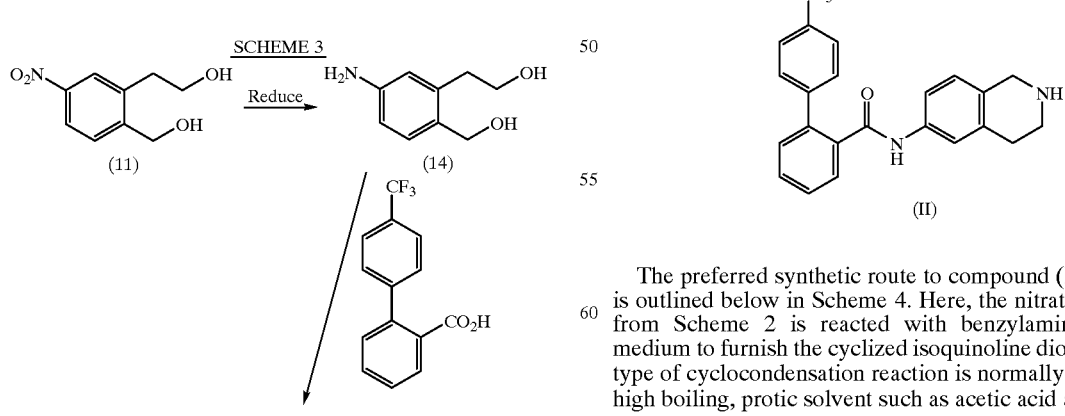

The preferred synthetic route to compound (II), however, is outlined below in Scheme 4. Here, the nitrated diacid (9) from Scheme 2 is reacted with benzylamine in acidic medium to furnish the cyclized isoquinoline dione (16). This type of cyclocondensation reaction is normally effected in a high boiling, protic solvent such as acetic acid at a temperature sufficient to induce ring-closure, usually the reflux temperature of the solvent In the practice of the instant process, preferably an acetic acid solution of benzylamine and compound (9) is heated at reflux temperature for a period of 18 hours and the formed isoquinoline dione (16) is isolated by conventional workup. Alternatively, diacid (9) may be converted into an activated form as described hereinabove and then condensed with benzylamine. A two-step reduction furnishes the N-protected, 6-amino isoquinoline derivative (18) which is then functionalized with 4'-trifluoromethylbiphenyl-2-carboxylic acid or an activated form thereof to afford the benzylated amide (19). In the initial step of the reduction process, dione (16) may be reduced to compound (17) by a variety of reducing agents including various diborane and borohydride complexes such as diborane/THF, diborane/DMS, sodium borohydride/boron trifluoride etherate, and the like in aprotic solvent systems such as THF, alkyl ethers, toluene and so forth at temperatures which range from about 0° C. to the reflux temperature of the chosen solvent. In the preferred mode of the instant process, compound (16) is reduced to the N-protected, 6-nitroisoquinoline derivative (17) using sodium borohydride/boron trifluoride etherate in THF at 0° to reflux over a period of approximately 16 hours. In the second reductive step of the instant process, compound (17) is reduced to amine (18). The skilled artisan will recognize readily a number of methods available for the reduction of the aromatic nitro group of compound (17) including Zn/aqueous HCl, Fe/acetic acid/water, and a diversity of catalytic methods including hydrogenation in the presence of palladium, platinum, platinum oxide, rhenium and the like in protic or aprotic solvents at hydrogen pressures ranging from 1–1,000 psi. In the practice of the instant process, it is preferred that the reduction of compound (17) be effected using catalytic hydrogenation in the presence of platinum oxide in THF at a hydrogen pressure of 50 psi. Compound (18) is then coupled with 4'-trifluoromethylbiphenyl-2-carboxylic acid as described in Scheme 1 to furnish amide (19). A variety of preparative methods for the deprotection of compound (19) will be known to those skilled in the art. In the practice of the instant process, compound (19) is preferably deprotected using palladium hydroxide on carbon in the presence of ammonium formate. The deprotection step is effected at a temperature of 60° C. for a period of approximately 3 hours in a methanol/THF solvent system.

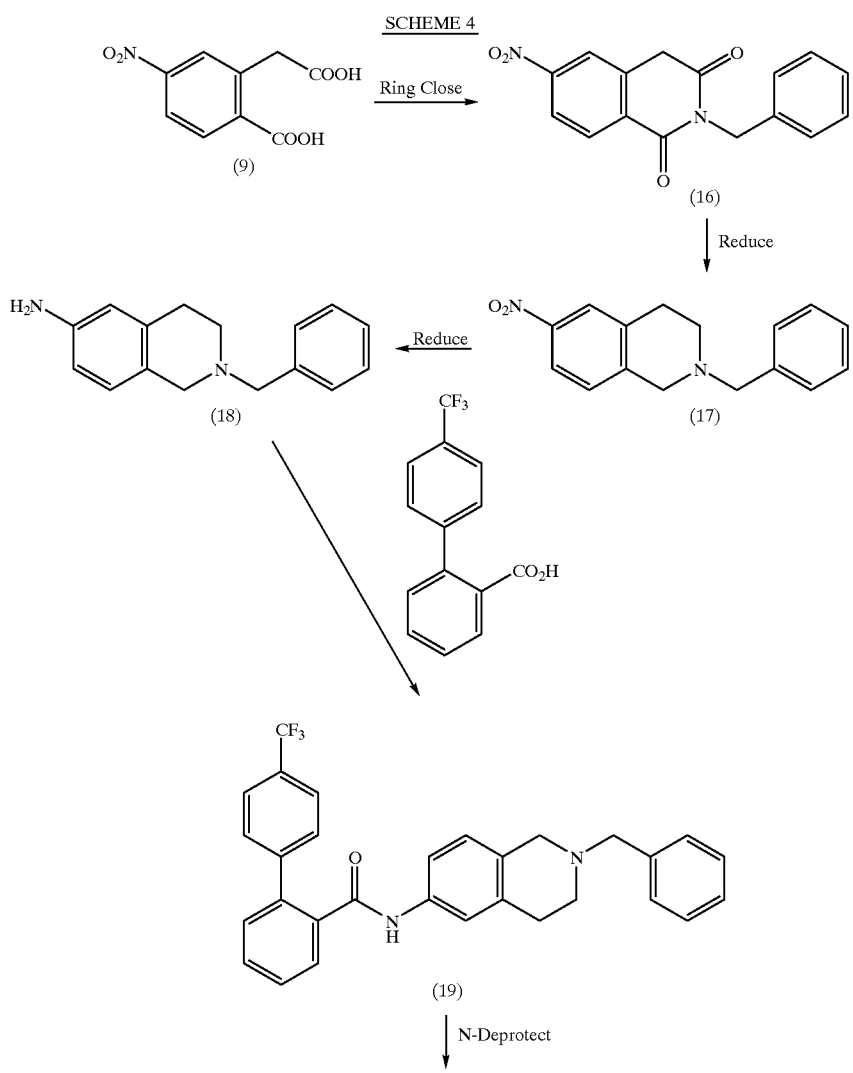

-continued

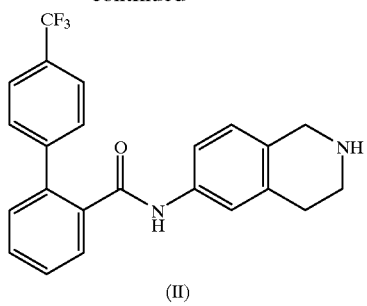

(II)

The coupling processes employed in the synthesis of compounds of formula (I) begin with compound (II) and generally involve conventional methods or minor modifications thereof. With specific reference to the compounds of the instant invention a total of ten preparative routes were used for the preparation of compounds of structure (I) and each of these is described in general terms in Methods A–J hereinbelow. It is to be understood, however, that the various preparative methods disclosed in the instant specification were chosen generally on the basis of convenience and not of limitation. The skilled artisan will appreciate that many conceptually viable pathways are available for the synthesis of compounds of structure (I), including various combinations of Methods A–J, and the exemplary schemes outlined hereinbelow are not to be construed as being the only possible preparative approaches. Experimental details and certain physicochemical data for each of the synthetic methods is furnished in Examples 5–14. For each individual Method A–J an exemplary synthesis is provided, which is followed thereafter by a listing of cognate preparations for each of the following respective methods. For the compounds of structure (I) described in this section it is noted that the free base was usually isolated. For use in biological screens, the free base was, in most instances, converted into the hydrochloride salt form by conventional methods.

Method A

The procedure of Method A is represented by the following scheme and is essentially analogous to the route described by Abdel-Magid, et al., Tetrahedron. Lett., 1990; 31: 5595. In Method A, an appropriately substituted aldehyde is condensed with compound (II) via a reductive amination procedure. Although a diversity of reducing agents such as sodium borohydride, sodium cyanoborohydride, lithium aluminum hydride, sodium triacetoxyborohydride and other suitable borohydride reducing agents may be employed with success in the practice of Method A, sodium triacetoxyborohydride is usually preferred. In addition, 1.0 to 2.0 equivalents of aldehyde are generally preferred. The reductive amination procedure of Method A may be carried out in either a protic or aprotic solvent such as methanol, ethanol, THF, or DMF.

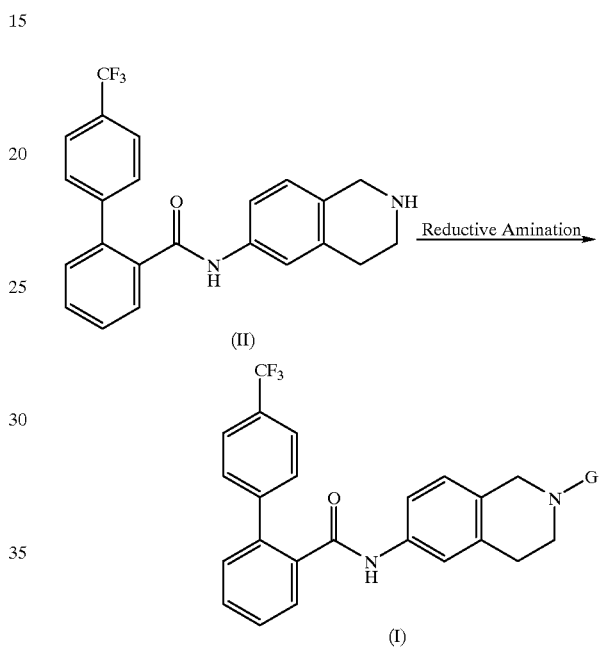

The experimental details and physicochemical data of the compounds produced by Method A are provided in Example 5 hereinbelow. A minor modification of this method was used to synthesize several related derivatives and these compounds, together with representative preparations, are also included in Example 5.

Method B

The procedure of Method B is represented by the following scheme. In Method B, a cyclocondensation reaction involving diol (15) and an appropriately-substituted amine is effected in the presence of a suitable activating agent. Any suitable activating agent which is able to convert the two hydroxyl moieties of (15) into reactive leaving groups may be employed. For example, the hydroxyl groups may be converted into their respective mesylates, tosylates, or triflates by reaction with a corresponding acid, acid halide or acid anhydride. Alternatively, the dihydroxyalkyl substituents of compound (15) may be converted into alkyl halides. In the practice of the instant Method, mesyl chloride is generally preferred as the cyclization catalyst. The cyclocondensation reaction of Method B is normally performed in an aprotic solvent such as THF or methylene chloride.

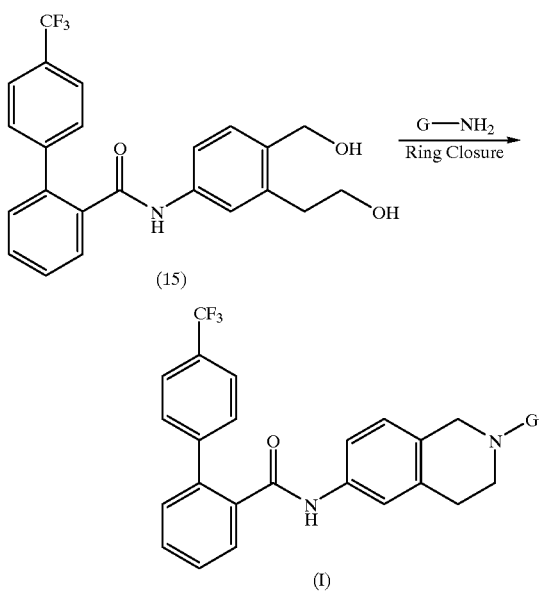

The experimental details and physicochemical data of the compounds produced according to Method B are provided in Example 6 hereinbelow.

Method C

The procedure of Method C is represented by the following scheme. In Method C, compound (II) is coupled, in the presence of a base, with an appropriate G-bearing moiety activated with a leaving group (—X). While many such leaving groups will be known to the skilled artisan, for purposes of the instant invention, it is generally preferred that the leaving group be a halogen atom such as chlorine, bromine or iodine, most preferably bromine. A wide variety of organic and inorganic bases may be used with success in this coupling reaction. However, it is generally preferred that an inorganic base, such as potassium carbonate be employed. Normally, the coupling reaction of Method C is conducted in an aprotic solvent such as DMF or acetonitrile.

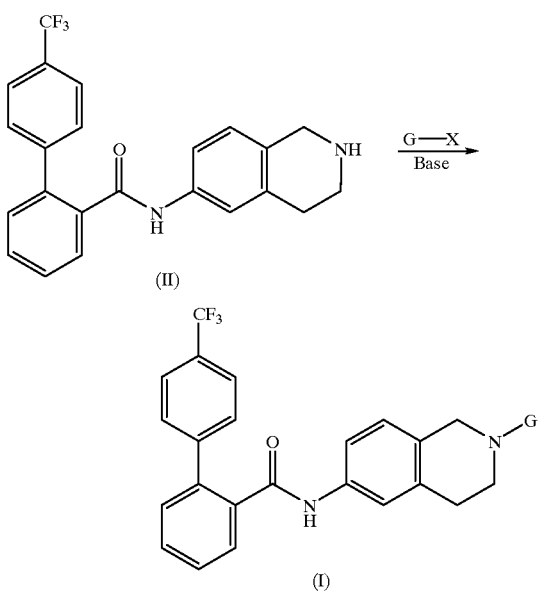

In two instances described hereinbelow, minor modifications with respect to reaction solvent and base were employed in the above coupling reaction. The experimental details and physicochemical data for the compounds produced by Method C, including certain modifications thereto, are provided in Example 7 hereinbelow.

Method D

The procedure of Method D is represented by the following scheme. In Method D, compound (II) is coupled with an appropriate G-bearing substrate via a Michael addition reaction. Such addition reactions are well known to those skilled in the art, including the various permutations thereof. For a detailed discussion of the Michael addition reaction see, for example, H. O. House, *Modem Synthetic Reactions,* 2nd Ed., W. A. Benjamin, Inc., Menlo Park, Calif., 1972). These addition reactions are normally carried out in protic solvents such as water, the lower alcohols (e.g. methanol or ethanol) or acetic acid. In the present example, acetic acid is generally preferred.

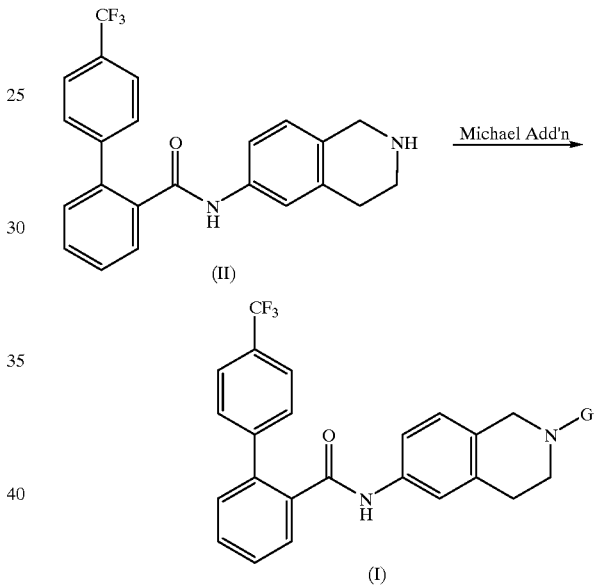

The experimental details and physicochemical data of the compounds produced according to Method D are provided in Example 8 hereinbelow.

Method E

The procedure of Method E is represented by the following scheme. In Method E, an activated form of Compound 70 from Example 7 is converted into the corresponding amide derivative by reaction with an appropriately substituted amine. A diversity of preparative methods are known to the skilled artisan for the amidation of carboxylic acid residues. For example, the acid substrate may be activated in the form of an acid halide, such as an acid chloride. An alterative, preferred method of carboxylic acid activation comprises the formation of an activated intermediate by the reaction of the free carboxylic acid with an appropriate carbodiimide, e.g. 1,1'-carbonyldiimidazole (CDI) or, preferably, 1-(3-dimethylaminopropyl)-3-ethylcarbodiimide hydrochloride (EDC). Such activation methods are described in detail hereinabove.

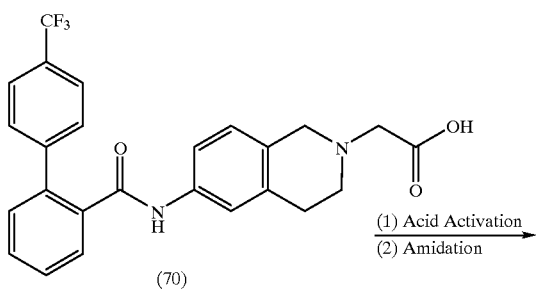

(70)

(1) Acid Activation
(2) Amidation

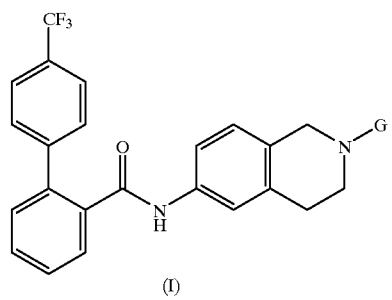

(I)

The experimental details and physicochemical data of the compounds produced according to Method E are provided in Example 9 hereinbelow.

Method F

The procedure of Method F is represented by the following scheme. In the practice of Method F, a precursor incorporating a reducible moiety, i.e. G', is converted into compound (I). It is to be understood that a wide variety of reducible substrates may be transformed successfully using this method and that this procedure is no way limited to the instant example which is illustrative for the synthesis of a compound of structure (I) by the reduction of a carbonyl compound. For purposes of the instant Method, an appropriately substituted carbonyl derivative (II') may be synthesized by treating compound (II) with a carboxylic acid or an activated form thereof. In the present case the compound, 4'-trifluoromethylbiphenyl-2-carboxylic acid-[2-(thiophen-2-yl-acetyl)-1,2,3,4-tetrahydroisoquinolin-6-yl]-amide (II') is converted into the corresponding reduced form (I) by treatment with an appropriate reducing agent. Reducing agents suitable for this purpose may include, for example, sodium borohydride, lithium aluminum hydride and other suitable borohydride compounds, catalytic hydrogenation, and so forth. In the instant example, sodium borohydride is generally preferred. A solvent system compatible with other functional groups which may be present and the nature of the reducible moiety involved will be determined readily by one of ordinary skill in the art. Such solvents include, for example, THF, DMF, acetic acid, methanol, ethanol and the like. However, depending upon the reactive nature of the reducible moiety, certain deviations which will be well known to the skilled artisan, may be required from the above general teaching.

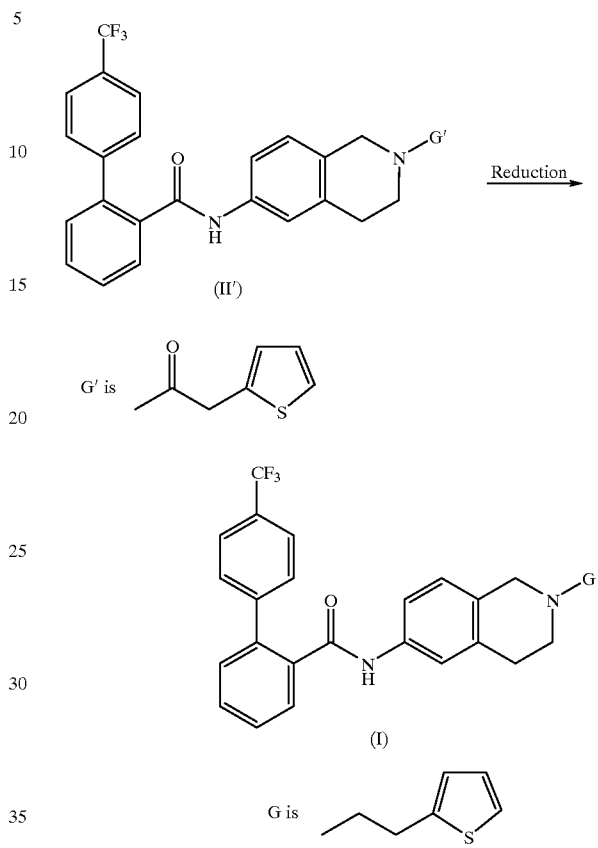

The related synthetic details and physicochemical data for the compounds produced according to Method F, including compound (II') are described hereinbelow in Example 10.

Method G

The procedure of Method G is represented by the following general scheme. In Method G, Compound 67 from Example 6 is derivatized by an appropriate synthetic sequence, preferably acylation, of the N-hydroxyethyl moiety of the isoquinoline nucleus. Where applicable, such derivatiation reactions, including acylation, may be effected in the presence of a base. For example, various organic bases such as triethylamine, pyridine, N,N'-dimethylaminopyridine, and the like may be employed conveniently. Similarly, certain inorganic bases such as sodium carbonate, potassium carbonate, and the like may also be used with success. In the practice of Method G, an organic base such as N,N'-dimethylaminopyridine is usually preferred. As has been noted previously, it is well within the ability of the skilled artisan to effect derivatizations of the N-hydroxyethyl moiety other than the acylation transformations disclosed in Method G, and the teachings of the instant Method are not be construed as being limited solely thereto.

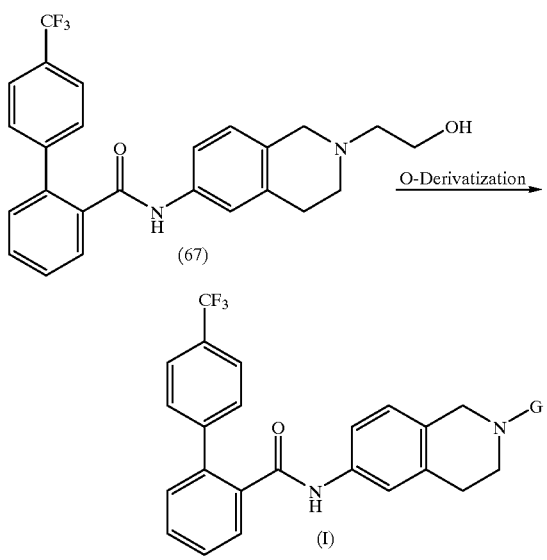

Specific values for —G will be found in Example 11 along with the synthetic details and physicochemical data related thereto.

Method H

The complete procedure of Method H is represented in the following two schemes.

In Step 1 of Method H, Compound 49 from Example 6 is hydrolyzed to the free N-aminoethyl Compound 94. In the practice of Method H. Compound 94 is most conveniently isolated in the form of the free base, however one skilled in the art will appreciate that a wide variety of acid addition salts may be formed with this substrate, if desired. Such acid addition salt forms may be formed as described hereinbelow.

Step 1

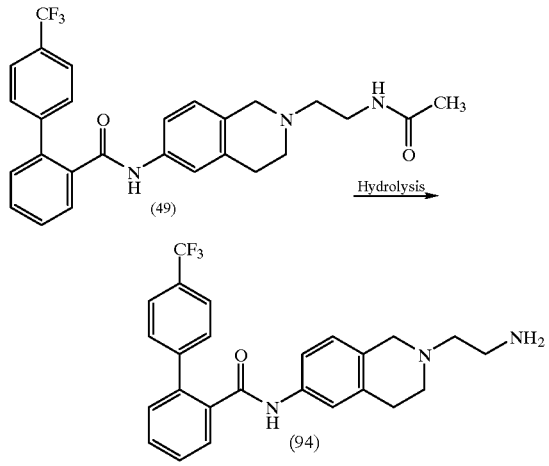

Step 2

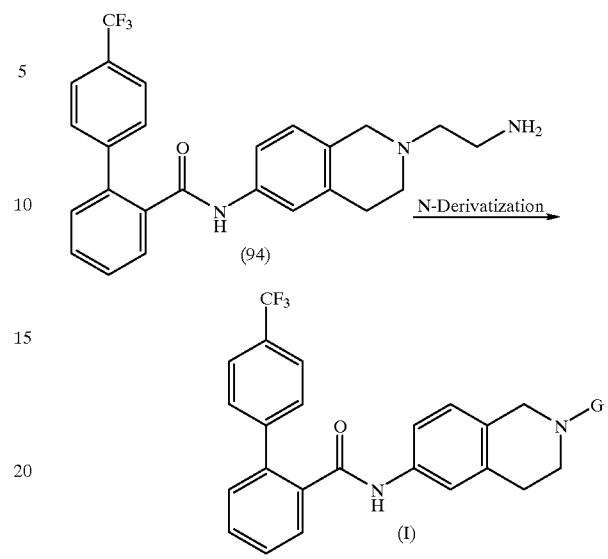

In Step 2 of Method H, the N-aminoethyl moiety of the isoquinoline ring nucleus of Compound 94 is derivatized in an appropriate synthetic sequence, preferably amidation. The N-aminoethyl moiety of Compound 94 may be amidated with a wide variety of reagents which may include carboxylic acids, acid halides, acid anhydrides, isocyanates, isothiocyanates and similar reactants which will be well known to those skilled in the art. The amidation procedures of Method H may be effected with or without the presence of a base. Furthermore, an activating agent such as 1,1'-carbonyldiimidazole (CDI) or 1-(3-dimethylaminopropyl)-3-ethylcarbodiimide hydrochloride (EDC) may be employed where appropriate. It is well within the purview of the skilled artisan to effect derivatizations of the N-aminoethyl moiety other than the preferred amidation transformations disclosed in Method H, and the teachings of the instant Method are not to be construed as being limited solely thereto. In several instances minor variations in the choice of amidating reagents were employed in the synthesis of certain compounds by this Method and pertinent experimental details for each of these variations are found in Example 12.

Specific values for —G as well as synthetic details and physicochemical data related thereto are presented in Example 12 shown hereinbelow.

Method I

The complete procedure of Method I is represented by the following two schemes.

In Step 1 of Method I, Compound 61 from Example 6 is deprotected to furnish Compound 106. In the instant example, catalytic hydrogenation was used to effect deprotection although alternate routes will be known to the skilled artisan.

Step 1

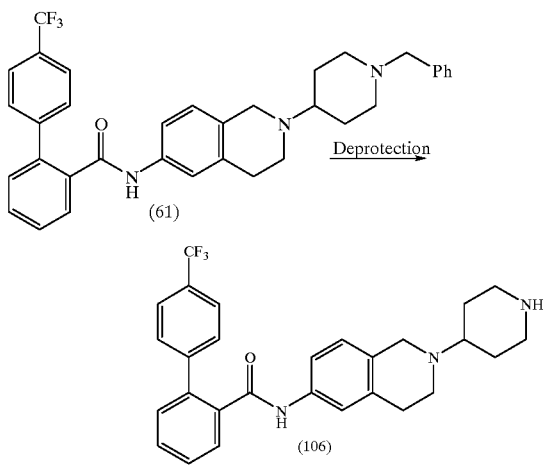

In Step 2 of Method I the piperidine ring nitrogen of Compound 106 is derivatized with an appropriate functionality, preferably an alkyl or acyl group. One skilled in the art will appreciate readily the fact that many analogous transformations are possible at this nitrogen atom by the introduction of substituents other than those described herein.

Step 2

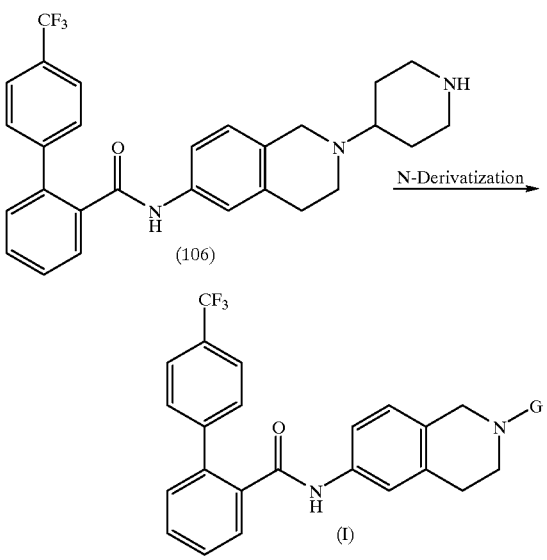

For purposes of the instant invention, the preferred alkyl or acyl substituents may be introduced by a variety of known methods. Alkylation procedures may involve contacting the amine substrate with an alkylating agent for example and alkyl halide or, preferably, alkylating the amine by a reductive amination procedure such as that described hereinabove in Method A. Acylation of the amine is preferably effected by a process analogous to that described hereinabove in Method H.

Exemplary, non-limiting values for -G as well as the synthetic details and physicochemical data related thereto for Method I will be found in Example 13 hereinbelow.

Method J

The procedure of Method J is shown below. Here, the cyanoethyl group of Compound 74 from Example 7 is cyclized with formic hydrazine in the presence of base to yield Compound 111. It will be appreciated that the nitrile moiety of Compound 74 is capable of functioning as the penultimate precursor to other heterocyclic ring systems and the present example is offered only for the purpose of illustration and not limitation.

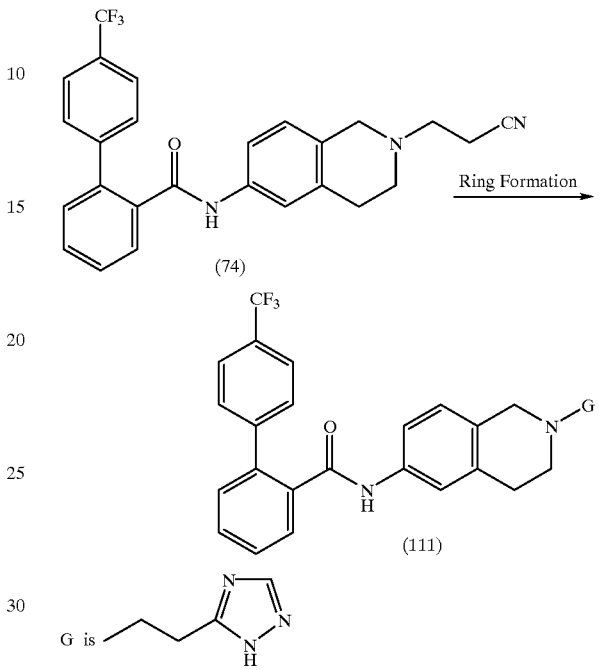

The preparative details and physicochemical data related thereto for Compound 111 of Method J are found in Example 14 hereinbelow.

Conventional methods and/or techniques of purification and separation known to those skilled in the art may be used to isolate the compounds of this invention. Such techniques include, for example, the well-known and established types of chromatography (such as HPLC, column chromatography using common adsorbents such as silica gel, and thin layer chromatography), recrystallization, and differential (i.e., liquid-liquid) extraction techniques.

The compounds described herein form cationic salts such as acid addition salts and the expression "pharmaceutically-acceptable salts" is intended to define but not be limited to such salts as the hydrochloride, hydrobromide, sulfate, hydrogen sulfate, phosphate, hydrogen phosphate, dihydrogenphosphate, acetate, succinate, citrate, methanesulfonate (mesylate) and p-toluenesulfonate (tosylate) salts, as well as hydrated or solvated forms thereof. For many compounds polyaddition salts are feasible and/or desirable.

The acid addition salts of the compounds of the present invention, including those of compound (II), may be prepared readily by reacting the base forms with an appropriate conjugate acid. When the salt is of a monobasic acid (e.g., the hydrochloride, the hydrobromide, the p-toluenesulfonate, the acetate), the hydrogen form of a dibasic acid (e.g., the hydrogen sulfate, the succinate) or the dihydrogen form of a tribasic acid (e.g., the dihydrogen phosphate, the citrate), at least one molar equivalent and usually a molar excess of the acid is employed. However when such salts as the sulfate, the hemisuccinate, the hydrogen phosphate or the phosphate are desired, the appropriate and stoichiometric equivalent of the acid will generally be used. The free base and the add are usually combined in a co-solvent from which the desired salt precipitates, or can be otherwise isolated by concentration of the mother liquor or by the precipitative effect obtained by the addition of a non-solvent.

The compounds of the instant invention are orally administrable and are accordingly used in combination with a pharmaceutically acceptable carrier or diluent suitable to oral dosage forms. Suitable pharmaceutically-acceptable carriers include inert solid fillers or diluents and sterile aqueous or organic solutions. The active compound will be present in such pharmaceutical compositions in amounts sufficient to provide the desired dosage amount in the range described below. Thus, for oral administration the compounds may be combined with a suitable solid or liquid carrier or diluent to form capsules, tablets, powders, syrups, solutions, suspensions and the like. The pharmaceutical compositions may, if desired, contain additional components such as flavorants, sweeteners, excipients and the like.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

The compounds of the instant invention may also be administered parenterally. For parenteral administration the compounds may be combined with sterile aqueous or organic media to form injectable solutions or suspensions. Solutions or suspensions of these active compounds can be prepared in water suitably mixed with a surfactant such as hydroxypropylcellulose. If necessary, the aqueous solutions should be suitably buffered and the liquid diluent first rendered isotonic with sufficient saline or glucose. In this capacity, the sterile aqueous media employed are all readily available by standard techniques well known to those of ordinary skill in the art. The parenterally administrable preparations may also be manufactured in the form of sterile solid compositions which can also be dissolved in sterile water, or some other sterile injectable medium immediately prior to intended use. Dispersions can also be prepared in sesame or peanut oil, ethanol, water, polyol (e.g., glycerol, propylene glycol and liquid polyethylene glycol), suitable mixtures thereof, vegetable oils, N-methyl glucamine, polyvinylpyrrolidone and mixtures thereof in oils as well as aqueous solutions of water-soluble pharmaceutically acceptable salts of the compounds. Under ordinary conditions of storage and use, these preparations may contain a preservative to prevent the growth of microorganisms. The injectable solutions prepared in this manner can then be administered intravenously, intraperitoneally, subcutaneously, or intramuscularly.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. They may be sterilized, for example, by filtration through a bacteria-retaining filter, by incorporating sterilizing agents into the compositions, or by irradiating or heating the compositions where such irradiating or heating is both appropriate and compatible with the drug formulation.

Additional pharmaceutical formulations may include, inter alia, suppositories, sublingual tablets, topical dosage forms and the like and these may be prepared according to methods which are commonly accepted in the art.

The dosage of a compound of the instant invention which is administered will generally be varied according to principles well known in the art taking into account the severity of the condition being treated and the route of administration. In general, a compound will be administered to a warm blooded animal (such as a human) so that an effective dose, usually a daily dose administered in unitary or divided portions, is received, for example a dose in the range of about 0.1 to about 15 mg/kg body weight, preferably about 1 to about 5 mg/kg body weight. The total daily dose received will generally be between 1 and 1000 mg, preferably between 5 and 350 mg. The above dosages are exemplary of the average case; there can, of course, be individual instances where higher or lower dosage ranges are merited, and such deviations are within the scope of this invention.

The compounds of the instant invention are active as determined in the following biological screens.

The activity of a compound according to the invention can be assessed by measuring inhibition of Apo B secretion in HepG2 cells.

HepG2 cells are grown in Dulbecco's Modified Eagles Medium plus 10% fetal bovine serum (growth medium; Gibco) in 96-well culture plates in a humidified atmosphere containing 5% carbon dioxide until they are approximately 70% confluent A compound to be tested is dissolved at 10–20 mM in dimethyl sulfoxide which is then diluted to 1 mM in growth medium. Serial 1:1 dilutions of this stock are made in growth medium and 100 ml of each are added to separate wells of a 96-well culture plates containing HepG2 cells. Twenty four hours later, growth medium is collected and assayed by specific ELISA for Apo B and, as a corol, Apo Al concentrations. Inhibitors are identified as compounds that decrease Apo B secretion into the medium without affecting the secretion of apoAl. The ELISA for Apo B is performed as follows. Monoclonal antibody against human Apo B (Chemicon; Temecula, Calif.) is diluted to 5 mg/ml in phosphate buffered (8.76 g/L NaCl, 0.385 g/L $KH_2PO_4$, 1.25 g/L $K_2HPO_4$) saline/azide (PBS+0.02% Na azide) and 100 ml are added to each well of a 96-well plate (NUNC Maxisorb, Rochester, N.Y.). After an overnight incubation at room temperature, the antibody solution is removed and wells are washed 3 times with PBS/azide. Non-specific sites on the plastic are blocked by incubating wells for 1–3 hours in a solution of 1% (w/v) bovine serum albumin (BSA) made in PBS/azide. 100 μl of various dilutions of growth medium from the HepG2 cells or Apo B in the form of ultracentrifugally isolated LDL (diluted in 0.004% Tween 20/1% BSA in PBS/azide) are added to each well and incubated for 18 hours. Wells are aspirated and washed 3 times (0.1% Tween 20 in PBS) prior to adding 100 ml of a 1/1000 dilution of the secondary antibody, goat anti-human Apo B (Chemicon). After a 3 hr incubation at room temperature, this solution is aspirated and the wells are again washed 3 times as above. 100 ml of a 1:1600 dilution (in PBS/1% BSA/2 mM $MgCl_2$) of rabbit antigoat IgG conjugated to alkaline phosphatase (Sigma; St. Louis, Mo.)

are then added to each well and incubated for 1 hr at room temperature. After aspirating, the wells are washed 4 times as above and 100 ml of 1 mg/ml p-nitrophenylphosphate (pNPP; Sigma) in 25 mM sodium bicarbonate/2 mM $MgCl_2$, pH 9.5, are added to each well and incubated for 20–30 minutes and then the reaction is terminated by the addition of 50 ml of 0.2N NaOH. Absorbance of each well is read at 405 nm and the background at 650 nm is subtracted. Apo B concentration is calculated from a standard curve constructed from purified LDL standards that are run in parallel in the same assay. Apo Al is measured in an analogous manner except that antibodies for Apo Al (Chemicon) are used in place of the antibodies for Apo B and antigen incubation is at 37° instead of room temperature.

Activity can also be confirmed if a test compound inhibits MTP activity directly.

Inhibition of MTP activity by a compound may be quantitated by observing the inhibition of transfer of radiolabeled triglyceride from donor vesicles to acceptor vesicles in the presence of soluble human MTP. The procedure for preparing MTP is based on the method of Wetterau and Zilversmit (Biochem. Biophys. Acta (1986) 875: 610). Briefly, human liver chunks, frozen at −80° C., are thawed on ice, minced, and rinsed several times with ice cold 0.25 M sucrose with all subsequent steps being performed on ice. A 50% homogenate in 0.25 M sucrose is prepared using a Potter-Elvehjem Teflon pestle. The homogenate is diluted 1:1 with 0.25 M sucrose and centrifuged at 10,000×g for 20 min at 4° C. The pellet is resuspended in sucrose and recentrifuged at 10,000×g for 20 min. The supernatants are combined and the microsomes pelleted by centrifugation at 105,000×g for 75 min. The supernatant is discarded and the microsomal pellet is suspended in a minimal volume of 0.25 M sucrose, diluted to 3 ml per gm starting liver weight with 0.15 M Tris-HCl pH 8.0. This suspension is divided into 12 fractions, and centrifuged at 105,000×g for 75 min. The supernatants are discarded and the microsomal pellets are stored frozen at −80° C. until needed. For preparation of MTP prior to performing the assay, a thawed pellet is suspended in 12 ml of cold 50 mM Tris-HCl, 50 mM KCl, 5 mM MgCl, pH 7.4 and 1.2 ml of a 0.54% deoxycholate (pH 7.4) solution is added slowly with mixing to disrupt the microsomal membrane. After a 30 min incubation on ice with gentle mixing, the suspension is centrifuged at 105,000×g for 75 min. The supernatant, containing the soluble MTP protein, is dialyzed for 2–3 days with 4 changes of assay buffer (150 mM Tris-HCl, 40 mM NaCl, 1 mM EDTA, 0.02% NaN3, pH 7.4). The human liver MTP is stored at 4° C. and diluted 1:5 with assay buffer just before use. MTP preparations show no notable loss of transfer activity with storage up to 30 days.

Liposomes are prepared under a nitrogen atmosphere by the room temperature, bath sonication of a dispersion of 400 mM egg phosphatidylcholine (PC), 75 mM bovine heart cardiolipin, and 0.82 mM [$^{14}$C]-triolein (110 Ci/mol) (NEN; Boston, Mass.) in assay buffer. The lipids in chloroform are added in the proper amounts and dried under a nitrogen stream before hydrating with assay buffer. Acceptor liposomes are also prepared under a nitrogen atmosphere by the room temperature bath sonication of a dispersion of 1.2 mM PC, 2.3 mM triolein and 30 pM [$^3$H]-PC (50 Ci/mol) (NEN; Boston, Mass.) in assay buffer. The donor and acceptor liposomes are centrifuged at 160,000×g for 2 hrs at 7° C. The top 80% of the supernatant, that contains small unilamellar liposomes, is carefully removed and stored at 4° C. until required for subsequent use in the transfer assays.

MTP activity is measured using a transfer assay which is initiated by mixing donor and acceptor vesicles together with the soluble MTP and a compound to be tested. To 100 ml of either a 5% BSA (control) or 5% BSA containing the test compound, are added 500 ml assay buffer, 100 ml donor liposomes, 200 ml acceptor liposomes and 100 ml of diluted MTP protein. After incubabon at 37° C. for 45 min., triglyceride transfer is terminated by adding 500 ml of a 50% (w/v) DEAE cellulose suspension in assay buffer. Following 4 min of agitation, the donor liposomes, bound to the DEAE cellulose, are selectively sedimented using low speed centrigation. An aliquot of the supernatant containing the acceptor liposomes is counted and the $^3$H and $^{14}$C counts are used to calculate the percent recovery of acceptor liposomes and the percent triglyceride transfer using first order kinetics. Inhibition of triglyceride transfer by test compound is manifest as a decrease in $^{14}$C radioactivity compared to controls where no test compound is present.

Activity of a test compound as an MTP inhibitor may also be demonstrated in vivo according to the following assay:

Male mice (20–30 g.; various strains) are dosed by oral gavage (0.25 ml/25 g. body weight) with the test compound in the form of a suspension in an aqueous 0.5% methyl cellulose solution. Compound solutions are dosed either multiple times over several days or, alternatively, once 90 minutes before the mice are sacrificed and blood is collected for the preparation of serum. The serum is assayed for triglyceride and cholesterol concentration using commercial enzymatic assays (Triglyceride G: Wako Fine Chemicals; Edgewood, N.Y. and cholesterol HP; Boeringer Mannheim, Indianapolis, Ind.). Compounds which are MLTP inhibitors are identified by their ability to lower serum triglycerides as compared to control mice dosed solely with vehicle.

The present invention is illustrated by the following Examples. However, it is to be understood that these Examples are offered by way of illustration and are not to be construed as limiting in any way.

EXAMPLE 1

The following synthetic examples are illustrative of those procedures shown and described hereinabove for the sequential preparation of compounds 1–7 and (II) of Scheme 1. The numbers shown in parenthesis following the name of each tide compound correspond to the respective compound numbers in Scheme 1.

N-[2-(4-Bromo-phenyl)ethyl]-formamide (1)

500 g (1.78 mol) of 2-(4-Bromo-phenyl)ethylamine hydrobromide, 1 liter (12.4 mol) of ethyl formate and 248 mL (1.78 mol) of triethylamine were combined and heated to reflux for 3 hrs. The reaction was treated with 1 liter each of deionized water and ethyl acetate. The organic layer was separated and washed with 1 liter each of water and brine. The organic layer was dried over anhydrous magnesium sulfate, filtered and concentrated to yield 378 g of a solid.

MS (Cl): 245 (M+$NH_4^+$)

7-Bromo-3,4dihydro-isoquinoline hydrochloride (2)

In a 12 liter three neck round bottom flask, 4 kg of potyphosphoric add was heated to 150° C. and stirred. To the stirring polyphosphoric acid was added 530 g (3.75 mol) of phosphorus pentoxide in three portions of approximately 176.7 g each. Once the phosphorus pentoxide had dissolved, 378 g (1.66 mol) of N-[2-(4-bromo-phenyl)ethyl]-formamide was added. The reaction temperature was then raised to 200° C. and maintained for two hours. At this point, the reaction temperature was allowed to cool to 160° C. and poured onto 16 liters of ice. The mixture was stirred for 0.5 hours, basified to pH 12 with 10N sodium hydroxide solution and then extracted three times with 3 liters of methylene chloride. The combined organic layers were washed with 1 liter of saturated sodium chloride solution, dried over anhydrous sodium sulfate, filtered and concentrated to an oil. The oil was dissolved in 2.5 liters of methanol and saturated with anhydrous HCl gas. The resulting solution was concentrated to one liter in volume and 1 liter of diethyl ether was added. The resulting precipitate was filtered, washed with diethyl ether and air dried to yield 219 g of the title compound as a solid.

MS (Cl): 210 (M+H$^+$)

7-Bromo-1,2,3,4-tetrahydroisoquinoline (3)

A total of 219 g (0.89 mol) of 7-bromo-3,4-dihydroisoquinoline hydrochloride and 1.5 liters of water were combined and heated to 50° C. A total of 33.7 g (0.89 mol) of sodium borohydride was added in portions over 0.5 hours during which time the temperature rose to 62° C. The reaction was then cooled to ambient temperature and extracted three times with 1 liter of methylene chloride. The combined organic layers were washed with 1 liter of saturated sodium chloride solution, dried over anhydrous sodium sulfate and concentrated to yield 173 g of an oil.

MS (Cl): 212 (M+H$^+$)

7-Bromo-6-nitro-1,2,3,4-tetrahydroisoquinoline (4)

In a 5 liter three neck round bottom flask, 173 g (0.813 mol) of 7-bromo-1,2,3,4-tetrahydroisoquinoline was dissolved carefully into 950 mL of concentrated sulfuric add. The resulting solution was cooled to −5° C. and a solution of 82.7 g (0.816 mol) of potassium nitrate in 1 liter of concentrated sulfuric add was added dropwise. After addition, the reaction was maintained at −5° C. for 15 minutes and poured onto 3 liters of ice. The resulting mixture was basified to pH 14 with 50% sodium hydroxide solution. The basic solution was extracted three times with 1 liter of methylene chloride. The combined organic layers were washed with 1 liter each of water and saturated sodium chloride solution. The organic layer was dried over anhydrous sodium sulfate, filtered and concentrated to yield 201 g of an oil. The oil, preadsorbed onto silica gel, was charged onto a column of 4 kg of silica gel and eluted with a gradient of 1–5% methanol/methylene chloride. The fractions containing product were combined and concentrated to yield 115 g of a solid.

$^1$H NMR (300 MHz, CDCl$_3$) δ7.61 (s, 1H); 7.38 (s, 1H); 4.10 (s, 2H); 3.20 (t, 2H); 2.90 (t, 2H).

7-Bromo-6-nitro-3,4-dihydro-1H-isoquinoline-2-carboxylic acid tert-butyl ester (5)

A 115 g (0.447 mol) sample of 7-bromo-6-nitro-1,2,3,4-tetrahydroisoquinoline, 45.2 g (0.447 mol) of triethylamine, 97.5 g (0.447 mol) of di-tert-butyl dicarbonate, 3.2 liter of dioxane and 0.5 liter of water were combined and stirred at ambient temperature for 1.5 hrs. The reaction was concentrated to remove the dioxane, 1 liter of saturated sodium bicarbonate was added and the mixture was extracted two times with 1 liter of methylene chloride. The organic layer was washed with brine, dried over magnesium sulfate and concentrated. The resulting solid was recrystallized from isopropanol to yield 118 g of a solid.

$^1$H NMR (250 MHz, DMSO) δ7.89 (s, 1H); 7.81 (s, 1H); 4.58 (s, 2H); 3.56 (t, 2H); 2.81 (t, 2H); 1.42 (s, 9H).

6-Amino-3,4-dihydro-1H-isoquinoline-2-carboxylic acid tert-butyl ester (6)

A total of 59 g (0.16 mol) of 7-bromo-6-nitro-3,4-dihydro-1H-isoquinoline-2-carboxylic acid tert-butyl ester, 10 g of 5% palladium on calcium carbonate and 49 g of ammonium acetate in 1 liter of acetic acid was hydrogenated on a Parr shaker for 5 hrs. The reaction was filtered, concentrated, basified to pH 12 with 4N sodium hydroxide and extracted with methylene chloride. The organic layer was washed with water and brine, dried over magnesium sulfate and concentrated to yield 40 g of the title compound in the form of an oil.

$^1$H NMR (300 MHz, DMSO) δ4.87 (s, 2H); 4.27 (s, 2H); 3.44 (t, 2H); 2.57 (t, 2H); 1.39 (s, 9H).

6-[(4'-Trifluoromethyl-biphenyl-2-carbonyl)-amino]-3,4-dihydro-1H-isoquinoline-2-carboxylic acid tert-butyl ester (7)

A 7.6 g (29 mmol) sample of 4'-trifluoromethyl-biphenyl-2-carboxylic acid, 7.1 g (29 mmol) of 6-amino-3,4-dihydro-1H-isoquinoline-2-carboxylic acid tert-butyl ester, 100 mg of DMAP and 6.1 g (32 mmol) of EDCl were reacted in 130 mL of methylene chloride for 12 hrs. The reaction mixture was extracted with 2×150 mL 1N HCl, 2×150 mL 1N NaOH, 150 mL water, brine and then concentrated to yield 14 g of a beige foam.

MS (Cl): 519 (M+Na$^+$)

$^1$H NMR (250 MHz, CDCl$_3$) δ4.49 (s, 2H); 3.60 (t, 2H); 2.77 (t, 2H).

4'-Trifluoromethyl-biphenyl-2-carboxylic acid (1,2,3,4-tetrahydroisoquinolin-6-yl)-amide (II)

A total of 4 g (8 mmol) of 6-[(4'-trifluoromethyl-biphenyl-2-carbonyl)-amino]3,4-dihydro-1H-isoquinoline-2-carboxylic acid tert-butyl ester and 6 mL (78 mmol) of trifluoroacetic acid were mixed in 60 mL of methylene chloride for 5 hrs. Methylene chloride (40 mL) was added and the organic layer was washed with 3×50 mL of saturated sodium bicarbonate followed by brine. The organic layer was dried over odium sulfate and concentrated to yield 3.1 g of solid.

MS (Cl): 397 (M+H$^+$)

EXAMPLE 2

The following synthetic examples are illustrative of those procedures shown and described hereinabove for the sequential preparation of compounds 8–13 of Scheme 2. The numbers shown in parenthesis following the name of each title compound correspond to the respective compound numbers in Scheme 2.

2-(Carboxy-5-nitrophenyl)malonic acid dimethyl ester (8)

A solution of 2-chloro-4-nitrobenzoic acid (75 g, 372 mmol) in dimethyl malonate (900 mL) was perfused with nitrogen for 15 min. Sodium methoxide (48.3 g, 894 mmol) was added in one portion and the contents exothermed to 48° C. Fifteen minutes later, copper (I) bromide (5.4 g, 37 mmol) was added in one portion and the contents were heated to 70° C. for 24 hrs. The reaction, which was 70% complete as determined by NMR, was subsequently heated to 85° C. for 5 hrs to completely consume the remaining 2-chloro4-nitrobenzoic acid. Water (900 mL) was added to the cooled reaction followed by hexanes (900 mL). The aqueous layer was separated, toluene (900 mL) was added, the mixture was filtered and aqueous layer separated. Fresh toluene (1800 mL) was added to the aqueous layer and the biphasic mixture acidified with 6N aqueous HCl (90 mL). A white precipitate formed and the contents were stirred for 18 hrs.

The product was filtered off and dried to give a white solid (78.1 g, 70%) mp 153° C.

$^1$H NMR (DMSO) δ8.37 (d, J=2 Hz, 1H), 8.30 (d, J=1 Hz, 2H), 5.82 (s, 1H), 3.83 (s, 6H).

$^{13}$C NMR (DMSO) δ168.0, 167.3, 149.4, 137.1, 135.8, 132.5, 125.4, 123.7, 54.5, 53.4.

Anal. Calcd for $C_{11}H_{10}NO_8$: C, 48.49; H, 3.73; N, 4.71. Found: C, 48.27; H, 3.72; N, 4.76.

2-Carboxymethyl-4-nitrobenzoic acid (9)

To a solution of 2-(carboxy-5-nitrophenyl)malonic acid dimethyl ester, (25.0 g, 84 mmol) in methanol (200 mL), sodium hydroxide (5 g, 125 mmol) in water (200 mL) was added. After 3 hrs the reaction was complete, the methanol was removed under vacuum, the contents cooled to 0° C. and acidified with concentrated HCl (37 mL). The aqueous layer was extracted twice with ethyl acetate (200 mL then 100 mL), the combined organic layers were dried with magnesium sulfate, most of the solvent removed under vacuum, and methylene chloride (30 mL) was then added. The formed white solid was filtered off and dried to give 19.3 g of product as a white solid, mp 180–82°0 C. IR(KBr) 3080, 3055, 2983, 1707, 1611, 1585, 1516, 1491, 1424, 1358, 1298, 1237 cm–$^1$.

$^{13}$C NMR (DMSO) δ172.3, 167.5, 149.2, 138.8, 137.3, 132.1, 127.2, 122.4, 39.8. Anal. Calcd for $C_9H_{17}NO_6$: C, 48.01; H, 3.13; N, 6.22. Found: C, 47.67; H, 3.19; N, 6.31.

2-(2-Hydroxymethyl-5-nitrophenyl)ethanol (11) through alternative intermediate (10)

A mixture of 2-carboxymethyl-4-nitrobenzoic acid (13 g, 57.7 mmol), acetic anhydride (5.45 mL, 57.7 mmol) and toluene (130 mL) were heated to reflux for 5 hrs. The solvent was removed under vacuum to yield 6-nitro-isochroman-1,3-dione (compound 10) in Scheme 2) as a yellow solid (10.51 g, 88%). Borane tetrahydrofuran complex (35.6 mL, 1M in THF) was added dropwise over 40 min to a solution of 6-nitro-isochroman-1,3-dione (2 g, 9.66 mmol) in THF (40 mL) at 0° C. The contents were then stirred for 18 hrs at 25° C., cooled to 0° C., quenched with methanol (30 mL), and stirred for 1 hr. The solvents were removed under vacuum, ethyl acetate (30 mL) was added and the organic phase was washed with 10% aqueous hydrochloric acid. The aqueous acidic layer was backwashed with ethyl acetate (30 mL), the combined organic layers were dried with magnesium sulfate, and evaporated under vacuum until approximately 2 mL of ethyl acetate remained. This solution was filtered through silica gel washing with methylene chloride (30 mL) to remove impurities. The silica gel was flushed with ethyl acetate, the solvent was removed under vacuum to give a solid which was slurried in methylene chloride and filtered to afford the title diol as a white solid, 1.38 g , 73%.

2-(2-Hydroxymethyl-5-nitrophenyl)-ethanol (11)

A THF (60 mL) solution of 2-carboxymethyl-4-nitrobenzoic acid (3.0 g, 13.3 mmol) was treated with borane-THF complex (53.3 mL, 53.3 mmol) over 15 min at 0° C. The reaction was stirred for 18.5 hrs, quenched with THF/water (1:1, 30 mL), water (20 mL) added and the layers separated. The aqueous layer was backwashed with THF (30 mL), the combined organic phase was washed with brine, dried with magnesium sulfate, and the solvent removed under vacuum to give the product as a white solid (2.05 g, 78%) mp 79–81° C.

IR(KBr) 3277, 3192, 2964, 2932, 1614, 1525, 1507, 1170, 1134, 1089, 1067 cm–$^1$.

$^{13}$C NMR (DMSO) δ149.1, 146.6, 139.2, 127.8, 124.3, 121.3, 61.2, 60.6, 34.9.

Anal. Calcd for $C_9H_{11}NO_4$: C, 54.82; H, 5.62; N, 7.10. Found: C, 54.54; H, 5.49; N, 7.07.

6-Nitro-1,2,3,4-tetrahydroisoquinoline (12)

Methanesulfonyl chloride (0.9 mL, 11.63 mmol) was added dropwise over 10 min to a solution of 2-(2-hydroxymethyl-5-nitrophenyl)-ethanol (1.0 g, 5.07 mmol), triethyl amine (1.8 mL, 12.9 mmol), in methylene chloride (20 mL). TLC showed the reaction to be complete after 30 min.

$^1$H NMR (CD$_3$Cl) δ8.17–11 (m, 2H), 7.65 (d, J=9 Hz, 1H), 5.36 (s, 2H), 4.49 (t, J=6 Hz, 2H), 3.25 (t, J=6 Hz, 2H), 3.08 (s, 3H), 2.98 (s, 3H).

The reaction mixture was washed with 10% aqueous HCl, saturated aqueous sodium bicarbonate, and brine. The organic layer was dried with magnesium sulfate, methylene chloride removed under vacuum and chased with THF (3×100 mL). The product (1.9 g) was employed directly in the next step without further purification. Ammonia (50 mL) was added to the dimesylate (1.9 g) in THF (30 mL) at –78° C. The contents were warmed to 24° C for 60 hrs, the excess ammonia distilled out, and solvent removed under vacuum to give the crude product (786 mg, 82%). Toluene was added, the solution was filtered through magnesium sulfate and the solvent was removed under vacuum to yield 721 mg (75%) of an amber oil.

$^1$H NMR (CDCl$_3$) δ7.97 (s, 1H), 7.95 (d, J=9 Hz, 1H), 7.15 (d, J=9 Hz, 1H), 4.07 (s, 2H), 3.15 (t, J=6 Hz, 2H), 2.89 (t, J =6Hz, 2H), 1.98 (bs, 1H).

6-Nitro-3,4-dihydro-1H-isoquinoline-2-carboxylic acid tert-butyl ester (13)

To a solution of 6-nitro-1,2,3,4-tetrahydro-isoquinoline (840 mg, 4.71 mmol) in methylene chloride (17 mL) containing triethylamine (0.72 mL, 5.17 mmol) was added BOC-anhydride (1.44 mL, 6.26 mmol). Saturated aqueous sodium bicarbonate was added 5 hr later, the phases separated, the organic layer dried with magnesium sulfate, and the solvent was removed under vacuum to give the product as a pale white solid (1.2 g, 92%). mp 138–41° C.

IR(KBr) 3056, 3018, 2982, 2935,1734,1684,1612, 1522, 1399, 1236 cm–$^1$. $^1$H

NMR (CDCl$_3$) δ8.04 (t, J=5 Hz, 1H), 8.01 (s, 1H), 7.26 (t, J=5 Hz, 1H), 4.65 (s,2H), 3.68 (t, J=6 Hz, 2H), 2.93 (t, J=6 Hz, 2H), 1.49 (s, 9H).

6-Amino-3,4dihydro-1H-isoquinoline-2-carboxylic acid tert-butyl ester (6)

The 6-nitro-3,4-dihydro-1H-isoquinoline2-carboxylic acid tert-butyl ester (82 mg, 0.29 mmol) in THF (2 mL) was hydrogenated with 5% Pt-C (50% water wet, 10 mg) at 50 psi for 5 hrs. The catalyst was filtered off, the solvent was removed under vacuum and the residue chromatographed on silica with ethyl acetate/hexanes to give 42 mg (57%) of the title product.

IR(KBr) 3005, 2975, 2928, 1685, 1627, 1509, 1423, 1365, 1166 cm–$^1$.

$^1$H NMR (CDCl$_3$) δ6.90 (d, J=6 Hz, 1H), 6.56 (d, J=6 Hz, 1H), 6.48 (s, 1H), 4.47 (s, 2H), 3.60 (m, J=6 Hz, 4H), 2.73 (t, J=6 Hz, 2H), 1.49 (s, 9H).

The product was then reacted with an activated form of 4'-trifluoromethylbiphenyl-2-carboxylic acid as disclosed previously to afford N-protected tetrahydroisoquinoline (7) which was then deprotected to furnish compound (II).

EXAMPLE 3

The following synthetic examples are illustrative of those procedures shown and described hereinabove for the preparation of compounds 14, 15 and (II) in Scheme 3. The numbers shown in parenthesis following the name of each title compound correspond to the respective compound numbers in Scheme 3.

2-(5-Amino-2-hydroxymethylphenyl)-ethanol (14)

Pt-C (50% water wet, 200 mg) was added to a THF (40 mL) solution of 2-(2-hydroxymethyl-5-nitrophenyl)-ethanol (1.0 g, 5 mmol) and the mixture was hydrogenated at 50 psi for 2 hrs. NMR showed complete reaction to form 2-(5-amino-2-hydroxymethyl-phenyl)-ethanol (compound (14) in Scheme 3).

$^1$H NMR (CD$_3$Cl) δ7.08 (d, J=2 Hz, 1H), 6.54–6.50 (m, 2H), 4.51 (s, 2H), 3.82 (t, J=6 Hz, 2H), 3.80–2.95 (bs, 4H), 2.84 (t, J=6 Hz, 2H).

4'-Trifluoromethylbiphenyl-2-carbonyl chloride

A solution of 4'-(trifluoromethyl)-2-biphenylcarboxylic acid (9.08 g, 34 mmol), thionyl chloride (12 mL) and dimethylformamide (0.05 mL) was heated to reflux for 2 hrs. at which time the reaction was determined to be complete by NMR. The excess thionyl chloride was distilled by displacing with toluene (56 mL). The solvent was removed under vacuum to give the title acid chloride as a white solid (9.46 g, 97%).

$^1$H NMR (CDCl$_3$) δ8.12 (dd, J=1 Hz, J=8 Hz, 1H), 7.70–7.37 (m, 7H). $^{13}$C NMR CD$_3$Cl δ(CO) 168.

4'-Trifluoromethylbiphenyl-2-carboxylic acid-[3-(2-hydroxymethyl)-4-hydroxymethylphenyl)]-amide (15)

The catalyst from the Pt-C hydrogenation described above was filtered off, triethylamine (1.4 mL, 10 mmol) was added, followed by the dropwise addition of a THF (10 mL) solution of the 4'-trifluoromethylbiphenyl-2-carbonyl chloride (1.44 g, 5 mmol) over a period of 1 hr. The contents were stirred for 24 hrs, the solvent was removed under vacuum, and ethyl acetate (40 mL) was added. The organic phase was washed with water (2×40 mL), dried with magnesium sulfate, and evaporated under vacuum. The residue was chased with toluene (3×40 mL) and evaporated to furnish 2.11 g of a white solid which was re-pulped in methylene chloride (21 mL) for 18 hrs., filtered, and dried to give the ti product as a white solid 1.71 g (81%).

4'-Trifluoromethylbiphenyl-2-carboxylic acid-(1,2,3,4-tetrahydroisoquinolin-6-yl)-amide (II)

Methanesulfonyl chloride (0.085 mL) was added to a 0° C. solution of 4'-trifluoromethyl-biphenyl-2-carboxylic acid-[3-(2-hydroxy-ethyl)-4-hydroxymethyl-phenyl]-amide (214 mg, 0.51 mmol) and triethylamine (0.18 mL) in THF (8.5 mL). TLC showed complete reaction after 30 min. The contents were cooled to −78° C., excess ammonia was added, and the contents were stirred for 18 hrs at 25° C. The solvents were removed under vacuum, methylene chloride (10 mL) and aqueous 1N HCl were added and the contents were stirred for 1 hr. The phases were separated and the aqueous phase was rendered alkaline with aqueous sodium hydroxide to a pH of 12. The organic phase was extracted with methylene chloride (4×10 mL), the solvent removed under vacuum to give a white solid (108 mg) which was chromatographed on silica eluting with 5% methanol/methylene chloride with 0.5% ammonium hydroxide. The product was obtained as a white solid (40 mg, 20%).

$^1$H NMR (CDCl$_3$) δ7.76–6.83 (m, 11H), 3.89 (s, 2H), 3.52 (d, J=7 Hz, 0.5H), 3.04 (t, J=6 Hz, 2H), 2.74 (m, 0.5H), 2.66 (t, J=7 Hz, 2H), 2.27 (s, 1H). $^{13}$C NMR CD$_3$Cl δ (aliphatic carbons only) 47.8, 43.6, 29.1.

EXAMPLE 4

The following synthetic examples are illustrative of those procedures shown and described hereinabove for the sequential preparation of compounds 16–19 and (II) in Scheme 4. The numbers shown in parenthesis following the name of each title compound correspond to the respective compound numbers in Scheme 4.

2-Benzyl-6-nitro-4H-isoquinoline-1,3-dione (16)

To a suspension of the diacid (9) (55 g, 0.244 mole) in acetic acid (550 mL) was added benzylamine (28.91 g, 0.27 mole). The reaction was heated to 115° C. for 18 hrs., cooled to 25° C., water was added (450 mL), the contents stirred for 2 hrs., and the product filtered off as a white solid. The product was washed with water (400 mL) and vacuum dried to give 59.51 g (82%).

$^1$H NMR (DMSO) δ8.29–8.20 (m, 3H); 7.3–7.19 (m, 5H); 5.03 (s, 2H); 4.35 (s, 2H). IR 3076, 2976, 1712, 1669, 1618, 1528, 1338, 1308 cm$^{-1}$. Anal. Calc'd for C$_{16}$H$_{12}$N$_2$O$_4$: C, 64.83; H, 4.08; N, 9.46. Found C, 64.72; H, 3.97; N, 9.49.

2-Benzyl-6-nitro-1,2,3,4-tetrahydroisoquinoline (17)

To a suspension of sodium borohydride (2.13 g, 56.2 mmole) in THF (56 mL) at 0° C. was added boron trifluoride etherate (9 mL, 73 mmole) dropwise. After stirring the contents for 1 hr., dione (16) (5.0 g, 16.9 mmole) in THF (150 mL) was added at 0° C. over a period of 1.5 hr. The contents were warmed to 25° C. for 30 min. and then refluxed for 16 hr. The completed reaction was cooled to 0° C. and cautiously quenched with aqueous 1N sodium hydroxide (75 mL, 75 mmole) while maintaining the temperature at approximately 9° C. The quenched reaction was stirred for 30 min. at 0° C., 1 hr. at 25° C., 50° C. for 18 hrs. and then cooled to 20° C. The solvents were removed under vacuum, ethyl acetate (100 mL) was added and the layers separated. The organic layer was washed with brine, treated with sodium sulfate and the solvents removed under vacuum to afford 4.73 g of a light brown oil which was of sufficient purity to employ in the next step.

$^1$H NMR (CDCl$_3$) δ7.98–7.29 (m, 5H); 7.38–7.10 (m, 5H); 3.71 (m, 2H); 2.99 (m, 2H); 2.82 (m, 2H). IR 3064, 2940, 2794, 1589, 1518, 1492, 1347, 1315 cm$^{-1}$. Anal. Calc'd for C$_{16}$H$_{16}$N$_2$O$_2$: C, 71.50; H, 6.00; N. 10.44. Found C, 70.76; H, 5.99; N, 10.33.

4'-Trifluoromethylbiphenyl-2-carboxylic acid-(2-benzyl-1,2,3,4-tetrahydroisoquinolin-6-yl)-amide (19) through amine intermediate (18)

A THF (184 mL) solution of compound (17) (4.6 g, 17 mmole) with platinum oxide (230 mg) was hydrogenated for 18 hrs. at 50 psi. The catalyst was filtered off and platinum oxide (230 mg) was added and the hydrogenation continued for 72 hrs. The completed hydrogenation was filtered to provide a THF solution of the intermediate, 2-benzyl-1,2,3,4-tetrahydroisoquinolin-6-yl amine (18). Triethylamine was added to the THF solution of (18) followed by the dropwise addition of 4'-trifluoromethylbiphenyl-2-carbonyl chloride (4.88 g., 17 mmole) from Example 3. The contents were stirred subsequently for 17 hrs. The solvent was removed under vacuum, water (50 mL) was added, the contents stirred for 3 hr., the product filtered off and dried under vacuum to yield 5.93 g (71%) of compound (19) as a white solid.

4'-Trifluoromethylbiphenyl-2-carboxylic acid-(1,2,3,4-tetrahydroisoquinolin-6-yl-amide (II)

Methanol (65 mL) and THF (135 mL) were added to palladium hydroxide on carbon (1.5 g, 50% water wet) under a nitrogen atmosphere followed by amine (19) (5.0 g, 10.3 mmole) of the previous example and ammonium formate (6.48 g, 103 mmole). The contents were heated to 60° C. for 3 hr., cooled to 25° C. and filtered. Aqueous sodium hydroxide (1N, 10 mL) was added to the filtrate, the organic solvents were removed under vacuum and water (40 mL) was added. The contents were stirred for 2 hr. and the crude product was filtered off and dried yielding 4.09 g of solid. This material was suspended in hexane/methylene chloride (40 mL of a 3:1 ration respectively) and stirred for 2 hrs. The pure product was filtered off and dried to give the title compound as a white solid (3.74 g, 92%).

4'-Trifluoromethylbiphenyl-2-carboxylic acid-(1,2,3,4-tetrahydroisoquinolin-6-yl)-amide (II) tosylate salt A 1.13 g (2.85 mmole) sample of Compound (II) was dissolved in 3 mL of ethyl acetate and p-toluenesulfonic acid (436 mg, 2.3 mmole) was added. The contents were stirred at ambient temperature for 18 hrs. and the resulting white solid was filtered off and washed with ethyl acetate. The solid product was dried under vacuum to afford 1.097 g of the title tosylate salt, mp 187° C.

$^1$H NMR (250 MHz, DMSO) δ10.47 (s, 1H); 7.73–6.94 (m, 16H); 4.54 (s, 2H); 3.71 (s, 2H); 2.47 (s, 2H); 2.25 (s, 3H).

The following synthetic examples are exemplary of those procedures shown and described hereinabove in Methods A–J for the synthesis of the compounds of structure (I) shown hereinabove.

EXAMPLE 5

Compounds 20–39

The following compounds were produced by the procedure of Method A described hereinabove. The following synthesis is exemplary of the procedure of Method A.
Compound 20

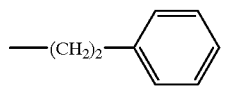

G is

4'-Trifluoromethylbiphenyl-2-carboxylic acid-(2-phenethyl-1,2,3,4-tetrahydroisoquinolin-6-yl)-amide A 400 mg (1.01 mmole) sample of compound (II), phenylacetaldehyde (121 mg, 1.01 mmole), sodium triacetoxyborohydride (320 mg, 1.52 mmole) and acetic acid (61 mg, 1.01 mmole) were stirred in 10 mL of 1,2-dichloroethane for 12 hrs. at ambient temperature. The reaction was diluted with methylene chloride, washed with 1N NaOH, water and brine. Purification was carried out with silica gel chromatography using 50% ethyl acetate/hexanes as the eluent.

MS (Cl): 501 (M+H$^+$)
$^1$H NMR (250 MHz, CDCl$_3$) δ3.65 (s, 2H); 2.91 (m, 4H); 2.87 (m, 4H).

The following compounds were synthesized in a manner analogous to that described hereinabove for Compound 20.
Compound 21
G is —CH$_2$CH$_3$ 4'-Trifluoromethylbiphenyl-2-carboxylic acid-(2-ethyl-1,2,3,4-tetrahydroisoquinolin-6-yl)-amide MS (Cl): 425 (M+H$^+$)
$^1$H NMR (250 MHz, CDCl$_3$) δ3.55 (s, 2H); 2.83 (t, 2H); 2.68 (t, 2H); 2.55 (q, 2H); 1.17 (t, 3H).
Compound 22
G is —(CH$_2$)$_2$CH$_3$ 4'-Trifluoromethylbiphenyl-2-carboxylic acid-(2-n-propyl-1,2,3,4-tetrahydroisoquinolin-6-yl)-amide MS (Cl): 439 (M+H$^+$)
$^1$H NMR (250 MHz, CDCl$_3$) d 3.55 (s, 2H); 2.82 (t, 2H); 2.67 (t, 2H); 2.44 (q, 2H); 1.61 (m, 2H); 0.94 (ti 2H).
Compound 23
G is —CH$_2$C(CH$_3$)$_3$ 4'-Trifluoromethylbiphenyl-2-carboxylic acid-[2-(2,2-dimethylpropyl)-1,2,3,4-tetrahydroisoquinolin-6-yl]-amide MS (Cl): 467 (M+H$^+$)
$^1$H NMR (250 MHz, CDCl$_3$) δ3.64 (s, 2H); 2.76 (m, 4H); 2.20 (s, 2H); 0.89 (s, 9H).
Compound 24

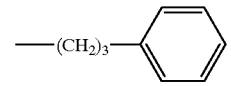

G is

4'-Trifluoromethylbiphenyl-2-carboxylic acid-[2-(3-phenylpropyl)-1,2,3,4-tetrahydroisoquinolin-6-yl]-amide MS (Cl): 515 (M+H$^+$)
$^1$H NMR (250 MHz, CDCl$_3$) δ3.55 (s, 2H); 2.82 (t, 2H); 2.68 (m, 4H); 2.52 (t, 2H); 1.91 (m, 2H).
Compound 25
G is —CH(CH$_3$)$_2$ 4'-Trifluoromethylbiphenyl-2-carboxylic acid-(2isopropyl-1,2,3,4-tetrahydroisoquinolin-6-yl)-amide MS (Cl): 440 (M+H$^+$)
$^1$H NMR (250 MHz, CDCl$_3$) δ3.65 (s, 2H); 2.87 (m, 1H); 2.80 (t, 2H); 2.72 (t, 2H); 1.11 (d, 6H).
Compound 26

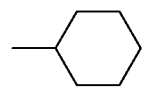

G is

4'-Trifluoromethylbiphenyl-2-carboxylic acid-(2-cyclohexyl-1,2,3,4-tetrahydroisoquinolin-6-yl)-amide MS (Cl): 479 (M+H$^+$)

$^1$H NMR (250 MHz, CDCl$_3$) δ3.71 (s, 2H); 2.79 (s, 4H); 2.45 (m, 1H); 1.92 (m, 2H); 1.83 (m, 2H); 1.60 (m, 1H); 1.29 (m, 5H).

Compound 27

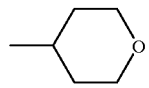

G is

4'-Trifluoromethylbiphenyl-2-carboxylic acid-[2-(tetrahydropyran-4-yl)-1,2,3,4-tetrahydroisoquinolin-6-yl]-amide MS (Cl): 481 (M+H$^+$)

$^1$H NMR (250 MHz, CDCl$_3$) δ4.04 (dd, 2H); 3.71 (s, 2H); 3.41 (t, 2H); 2.80 (s, 4H); 2.62 (m, 1H); 1.82 (d, 2H); 1.70 (dt, 2H).

Compound 28

G is —(CH$_2$)$_2$C(CH$_3$)$_3$

4'-Trifluoromethylbiphenyl-2-carboxylic acid-[2-(3,3-dimethylbutyl)-1,2,3,4-tetrahydroisoquinolin-6-yl]-amide MS (Cl): 482 (M+H$^+$)

$^1$H NMR (250 MHz, CDCl$_3$) δ3.55 (s, 2H); 2.82 (t, 2H); 2.68 (t, 2H); 2.49 (m, 2H); 1.49 (m, 2H); 0.93 (s, 9H).

The following compounds were synthesized by a modification of Method A. A general synthetic description and a listing of the compounds that were prepared by this modification are as follows:

A solution of an appropriately-substituted aldehyde (7.5 μmol), compound (II) (5 μmol), acetic add 7.5 μmol), and sodium triacetoxyborohydride (10 μmol) in 300 μL of 1,2 dichloroethane was shaken for 60 hrs. at ambient temperature. A 7.5 μL sample was removed and diluted with 93 μL of methanol for TLC and MS analysis. The remaining sample was evaporated to dryness under vacuum. The crude solid was dissolved in 500 μL of ethyl acetate and washed with 300 μL of 5% sodium bicarbonate. The organic layer was concentrated to dryness under vacuum.

Compound 29

G is —(CH$_2$)$_2$CH(CH$_3$)CH$_3$

4'-Trifluoromethylbiphenyl-2-carboxylic acid-[2-(3-methylbutyl)-1,2,3,4-tetrahydroisoquinolin-6-yl]-amide MS (Cl): 467 (M+H$^+$)

Compound 30

G is —(CH$_2$)$_6$CH$_3$

4'-Trifluoromethylbiphenyl-2-carboxylic acid-(2-n-heptyl-1,2,3,4-tetrahydroisoquinolin-6-yl)-amide MS (Cl): 495 (M+H$^+$)

Compound 31

G is —CH$_2$COCH$_3$

4'-Trifluoromethylbiphenyl-2-carboxylic acid-[2-(2-oxopropyl)-1,2,3,4-tetrahydroisoquinolin-6-yl]-amide MS (Cl): 453 (M+H$^+$)

Compound 32

G is —CH$_2$CH(CH$_3$)$_2$

4'-Trifluoromethylbiphenyl-2-carboxylic acid-(2-isobutyl-1,2,3,4-isoquinolin-6-yl)-amide MS (Cl): 453 (M+H$^+$)

Compound 33

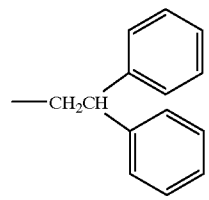

G is

4'-Trifluoromethylbiphenyl-2-carboxylic acid-[2-(2,2-diphenylethyl)-1,2,3,4-tetrahydroisoquinolin-6-yl]-amide MS (Cl): 577 (M+H$^+$)

$^1$H NMR (300 MHz, CDCl$_3$) δ4.30 (t, 1H); 3.61 (s, 2H).

Compound 34

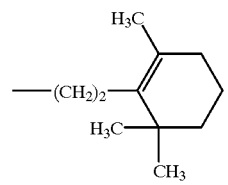

G is

4'-Trifluoromethylbiphenyl-2-carboxylic acid-{2-[2-(2,6,6-trimethylcyclohex-1-enyl)-ethyl]-1,2,3,4-tetrahydroisoquinolin-6-yl}-amide MS (Cl): 547 (M+H$^+$)

Compound 35

G is —(CH$_2$)$_{11}$CH$_3$

4'-Trifluoromethylbiphenyl-2-carboxylic acid-(2-dodecyl-1,2,3,4-tetrahydoisoquinolin-6-yl)-amide MS (Cl): 565 (M+H$^+$)

Compound 36

G is —CH$_2$C(CH$_3$)$_2$CH$_2$N(CH$_3$)$_2$

4'-Trifluoromethylbiphenyl-2-carboxylic acid-[2-(3-dimethylamino-2,2-dimethylpropyl)-1,2,3,4-tetrahydroisoquinolin-6-yl]-amide MS (Cl): 511 (M+H$^+$)

Compound 37

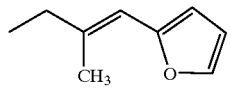

G is

4'-Trifluoromethylbiphenyl-2-carboxylic acid-[2-(3-furan-2-yl-2-methylallyl)-1,2,3,4-tetrahydroisoquinolin-6-yl]-amide MS (Cl): 517 (M+H$^+$)

Compound 38
G is —(CH₂)₂CH(CH₃)SCH₃

4'-Trifluoromethylbiphenyl-2-carboxylic acid-[2-(3-methylsulfanylbutyl)-1,2,3,4-tetrahydroisoquinolin-6-yl]-amide

MS (CI): 499 (M+H⁺)

Compound 39

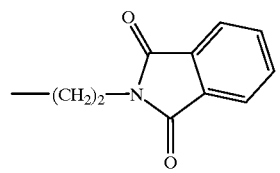

G is

4'-Trifluoromethylbiphenyl-2-carboxylic acid-{2-[2-(1,3-dioxo-1,3-dihydroisoindol-2-yl)-ethyl]-1,2,3,4-tetrahydroisoquinolin-6-yl}-amide

MS (CI): 570 (M+H⁺)

EXAMPLE 6

Compounds 40–67

The following compounds were produced by the procedure of Method B described hereinabove. The following synthesis is exemplary of the procedure of Method B.

Compound 40
G is —(CH₂)₃CH₃

4'-Trifluoromethylbiphenyl-2-carboxylic acid-(2-n-butyl-1,2,3,4-tetrahydroisoquinolin-6-yl)-amide Methanesulfonyl chloride (0.12 mL, 1.55 mmole) was added to a 0° C. solution of compound (15) (0.30 gm, 0.723 mmole) and triethylamine (0.25 mL, 1.79 mmole) in THF (7 mL). After 30 min. TLC indicated the reaction was complete. A total of 1.06 gm (14.4 mmole) of n-butylamine was added and the contents were stirred for 18 hrs. at ambient temperature. The solvent was removed under vacuum, the residue was dissolved in methylene chloride, washed with 1N NaOH and brine, and dried over sodium sulfate. Purification of the residue obtained upon evaporation was carried out on silica gel using a gradient of 0–8% methanol in methylene chloride as the eluent.

MS (CI): 453 (M+H⁺)

¹H NMR (250 MHz, DMSO) δ3.43 (s, 2H); 2.70 (t, 2H); 2.57 (t, 2H); 2.39 (t, 2H); 1.47 (m, 2H); 1.31 (m, 2H); 0.88 (t, 3H).

The following compounds were synthesized in a manner analogous to that described hereinabove for Compound 40.

Compound 41

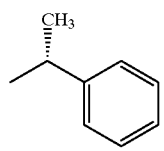

G is

4'-Trifluoromethylbiphenyl-2-carboxylic acid-[2-(1-(R)-phenylethyl)-1,2,3,4-tetrahydroisoquinolin-6-yl]-amide

MS (CI): 501 (M+H⁺)

¹H NMR (300 MHz, CDCl₃) δ3.75 (s, 2H); 1.45 (d, 3H).

Compound 42

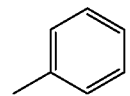

G is

4'-Trifluoromethylbiphenyl-2-carboxylic acid-(2-phenyl-1,2,3,4-tetrahydroisoquinolin-6-yl)-amide

MS (CI): 473 (M+H⁺)

¹H NMR (250 MHz, DMSO) δ4.29 (s, 2H); 3.48 (t, 2H); 2.82 (t, 2H).

Compound 43

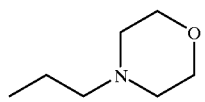

G is

4'-Trifluoromethylbiphenyl-2-carboxylic acid-[2-(2-morpholin-4-ethyl)-1,2,3,4-tetrahydroisoquinolin-6-yl]-amide

MS (CI): 510 (M+H⁺)

¹H NMR (300 MHz, DMSO) δ3.49 (s, 2H).

Compound 44
G is —CH₂CF₃

4'-Trifluoromethylbiphenyl-2-carboxylic acid-[2-(2,2,2-trifluoroethyl-1,2,3,4-tetrahydroisoquinolin-6-yl]-amide

MS (CI): 479 (M+H⁺)

¹H NMR (300 MHz, DMSO) δ3.72 (s, 2H).

Compound 45
G is —(CH₂)₂N(CH₃)₂

4'-Trifluoromethylbiphenyl-2-carboxylic acid-[2-(2-dimethylaminoethyl)-1,2,3,4-tetrahydroisoquinolin-6-yl]-amide

MS (CI): 468 (M+H⁺)

¹H NMR (300 MHz, DMSO) δ3.48 (s, 2H); 2.14 (s, 6H).

Compound 46
G is —(CH₂)₄N(CH₃)₂

4'-Trifluoromethylbiphenyl-2-carboxylic acid-[2-(2-dimethylaminobutyl)-1,2,3,4-tetrahydroisoquinolin-6-yl]-amide

MS (CI): 496 (M+H⁺)

¹H NMR (300 MHz, DMSO) δ3.43 (s, 2H); 2.11 (s, 6H).

Compound 47
G is —(CH₂)₂OCH₃

4'-Trifluoromethylbiphenyl-2-carboxylic acid-[2-(2-methoxyethyl)-1,2,3,4-tetrahydroisoquinolin-6-yl]-amide

MS (CI): 455 (M+H⁺)

¹H NMR (300 MHz, DMSO) δ3.50 (m, 4H); 3.24 (s, 3H); 2.64 (m, 6H).

Compound 48
G is —(CH$_2$)$_3$OH

4'-Trifluoromethylbiphenyl-2-carboxylic acid-[2-(3-hydroxypropyl)-1,2,3,4-tetrahydroisoquinolin-6-yl]-amide MS (Cl): 455 (M+H$^+$)
$^1$H NMR (300 MHz, DMSO) δ3.47 (s, 4H).

Compound 49
G is —(CH$_2$)$_2$NHCOCH$_3$

4'-Trifluoromethylbiphenyl-2-carboxylic acid-[2-(2-acetylaminoethyl)-1,2,3,4-tetrahydroisoquinolin-6-yl]-amide MS (Cl): 482 (M+H$^+$)
$^1$H NMR (250 MHz, DMSO) δ3.50 (s, 2H); 1.79 (s, 3H).

Compound 50

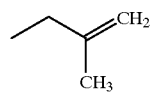

G is

4'-Trifluoromethylbiphenyl-2-carboxylic acid-[2-(2-methylallyl-1,2,3,4-tetrahydroisoquinolin-6-yl]-amide MS (Cl): 451 (M+H$^+$)
$^1$H NMR (300 MHz, DMSO) δ4.90 (s, 1H); 4.87 (s, 1H); 3.40 (s, 2H); 2.96 (s. 2H); 2.72 (t, 2H); 2.54 (t, 2H); 1.70 (s, 3H).

Compound 51
G is —CH$_2$)$_2$F

4'-Trifluoromethylbiphenyl-2-carboxylic acid-[2-(2-fluoroethyl)-1,2,3,4-tetrahydroisoquinolin-6-yl]-amide MS (Cl): 443 (M+H$^+$)
$^1$H NMR (300 MHz, DMSO) δ4.67 (t, 1H); 4.51 (t, 1H); 3.55 (s, 2H).

Compound 52

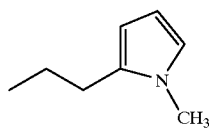

G is

4'-Trifluoromethylbiphenyl-2-carboxylic acid-{2-[2-(1-methyl-1H-pyrrol-2-yl)-ethyl]-1,2,3,4-tetrahydroisoquinolin-6-yl}-amide MS (Cl): 504 (M+H$^+$)
$^1$H NMR (300 MHz, DMSO) δ3.55 (s, 2H); 3.51 (s, 3H).

Compound 53
G is —(CH$_2$)$_3$N(CH$_3$)$_2$

4'-Trifluoromethylbiphenyl-2-carboxylic acid-[2-(3-dimethylaminopropyl)-1,2,3,4-tetrahydroisoquinolin-6-yl]-amide MS (Cl): 482 (M+H$^+$)
$^1$H NMR (300 MHz, DMSO) δ3.44 (s, 2H); 2.10 (s, 6H).

Compound 54

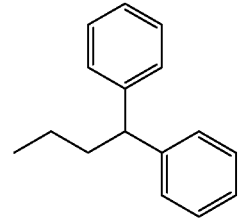

G is

4'-Trifluoromethylbiphenyl-2-carboxylic acid-[2-(3,3-diphenylpropyl)-1,2,3,4-tetrahydroisoquinolin-6-yl]-amide MS (Cl): 591 (M+H$^+$)
$^1$H NMR (300 MHz, DMSO) δ4.02 (t, 1H); 3.42 (s, 2H).

Compound 55
G is —CH$_2$CN

4'-Trifluoromethylbiphenyl-2-carboxylic acid-(2-cyanomethyl-1,2,3,4-tetrahydroisoquinolin-6-yl)-amide $^1$H NMR (300 MHz, DMSO) δ3.90 (s, 2H); 3.60 (s, 2H).

Compound 56
G is —(CH$_2$)$_5$CH$_3$

4'-Trifluoromethylbiphenyl-2-carboxylic acid-(2-n-hexyl-1,2,3,4-tetrahydroisoquiolin-6-yl)-amide MS (Cl): 481 (M+H$^+$)
$^1$H NMR (300 MHz, DMSO) δ3.44 (s, 2H); 0.85 (t, 3H).

Compound 57
G is —(CH$_2$)$_2$OCH$_2$CH$_3$

4'-Trifluoromethylbiphenyl-2-carboxylic acid-[2-(2-ethoxyethyl)-1,2,3,4-tetrahydroisoquinolin-6-yl]-amide MS (Cl): 469 (M+H$^+$)
$^1$H NMR (300 MHz, DMSO) δ3.53 (m, 4H); 1.10 (t, 3H).

Compound 58

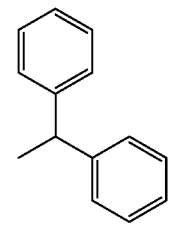

G is

4'-Trifluoromethylbiphenyl-2-carboxylic acid-(2-benzhydryl-1,2,3,4-tetrahydroisoquinolin-6-yl)-amide MS (Cl): 563 (M+H$^+$)
$^1$H NMR (300 MHz, DMSO) δ3.41 (s, 2H).

Compound 59
G is —(CH$_2$)$_3$OCH$_3$

4'-Trifluoromethylbiphenyl-2-carboxylic acid-[2-(3-methoxypropyl-1,2,3,4-tetrahydroisoquinolin-6-yl]-amide MS (Cl): 469 (M+H$^+$)
$^1$H NMR (300 MHz, DMSO) δ3.44 (s, 2H); 3.21 (s, 3H).

Compound 60

G is —(CH$_2$)$_4$CH$_3$

4'-Trifluoromethylbiphenyl-2-carboxylic acid-(2-n-pentyl-1,2,3,4-tetrahydroisoquiolin-6-yl)-amide MS (Cl): 467 (M+H$^+$)

$^1$H NMR (300 MHz, DMSO) δ3.44 (s, 2H); 0.86 (t, 3H).

Compound 61

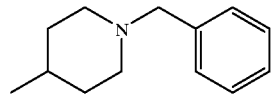

G is

4'-Trifluoromethylbiphenyl-2-carboxylic acid-[2-(1-benzylpiperidin-4-yl)-1,2,3,4-tetrahydroisoquinolin-6-yl]-amide MS (Cl): 570 (M+H$^+$)

$^1$H NMR (250 MHz, DMSO) δ3.61 (s, 2H); 3.44 (s, 2H); 2.70 (s, 4H).

Compound 62

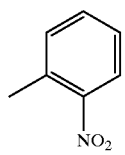

G is

4'-Trifluoromethylbiphenyl-2-carboxylic acid-[2-(2-nitrophenyl)-1,2,3,4-tetrahydroisoquinolin-6-yl]-amide MS (Cl): 518 (M+H$^+$)

$^1$H NMR (250 MHz, DMSO) δ4.58 (d, 2H); 4.36 (t, 2H).

Compound 63

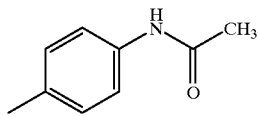

G is

4'-Trifluoromethylbiphenyl-2-carboxylic acid-[2-(4-acetaminophenyl)-1,2,3,4-tetrahydroisoquinolin-6-yl]-amide MS (Cl): 530 (M+H$^+$)

$^1$H NMR (250 MHz, DMSO) δ4.25 (s, 2H); 1.99 (s, 3H).

Compound 64

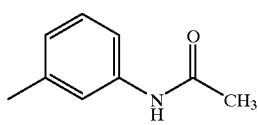

G is

4'-Trifluoromethylbiphenyl-2-carboxylic acid-[2-(3-acetylaminophenyl-1,2,3,4,-tetrahydroisoquinolin-6-yl]-amide MS (Cl): 530 (M+2)

$^1$H NMR (400 MHz, DMSO) δ4.25 (s, 2H); 3.44 (t, 2H); 1.99 (s, 3H).

Compound 65

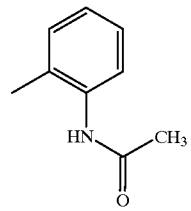

G is

4'-Trifluoromethylbiphenyl-2-carboxylic acid-[2-(2-acetylaminophenyl-1,2,3,4,-tetrahydroisoquinolin-6-yl]-amide MS (Cl): 530 (M+H$^+$)

$^1$H NMR (400 MHz, DMSO) δ4.00 (s, 2H); 3.04 (s, 2H); 2.88 (s, 2H); 2.04 (s, 3H).

Compound 66

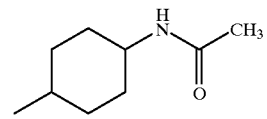

G is

4'-Trifluoromethylbiphenyl-2-carboxylic acid-[2-(4-acetylaminophenyl-1,2,3,4,-tetrahydroisoquinolin-6-yl]-amide MS (Cl): 536 (M+H$^+$)

$^1$H NMR (400 MHz, DMSO) δ2.26 (s, 3H).

Compound 67

G is —CH$_2$)$_2$OH

4'-Trifluoromethylbiphenyl-2-carboxylic acid-[2-(2-hydroxyethyl)-1,2,3,4-tetrahydroisoquinolin-6-yl]-amide MS (Cl): 441 (M+H$^+$)

EXAMPLE 7

Compounds 68–75

The following compounds were prepared by the procedure of Method C described hereinabove. The following synthesis is exemplary of the procedure of Method C.

Compound 68

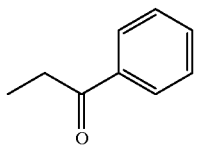

G is

4'-Trifluoromethylbiphenyl-2-carboxylic acid-[2-(2-oxo-phenylethyl)-1,2,3,4,-tetrahydroisoquinolin-6-yl]-amide Compound (II) (0.30 gm, 0.76 mmole), 2-bromoacetophenone (0.15 g, 0.76 mmole) and potassium carbonate (0.12 gm, 0.83 mmole) were combined in 20 mL of acetonitrile and heated to reflux for 1 hr., and then the solvent was evaporated under vacuum. The residue was dissolved in chloroform and washed with saturated sodium bicarbonate. Purification of the dried organic layer was accomplished with silica gel chromatography using 50% ethyl acetate in hexane as the eluent.

MS (Cl): 515 (M+H$^+$)

The following compounds were synthesized in a manner analogous to that described hereinabove for Compound 68. Preparative details for Compounds 74 and 75, which were synthesized by a minor modification of the above general method, are found under their respective headings.

Compound 69
G is —CH$_2$CONH$_2$

4'-Trifluoromethylbiphenyl-2-carboxylic acid-(2-carbamoylmethyl-1,2,3,4-tetrahydroisoquinolin-6-yl)-amide MS (Cl): 454 (M+H$^+$)
$^1$H NMR (250 MHz, DMSO) δ3.55 (s, 2H); 3.01 (s, 2H); 2.78 (m, 2H); 2.67 (m, 2H).

Compound 70
G is —CH$_2$COOH

{6-[(4-Trifluoromethylbiphenyl-2-carbonyl)-amino]-3,4-dihydro-1H-isoquinolin-2-yl}-acetic acid MS (Cl): 455 (M+H$^+$)
$^1$H NMR (250 MHz, DMSO) δ3.55 (s, 2H); 2.83 (s, 2H); 2.68 (s, 4H).

Compound 71
G is —CH$_2$COOCH$_3$

{6-[(4-Trifluoromethylbiphenyl-2-carbonyl)-amino]-3,4-dihydro-1H-isoquinolin-2-yl}-acetic acid methyl ester MS (Cl): 469 (M+H$^+$)
$^1$H NMR (300 MHz, CDCl$_3$) δ3.75 (s, 3H); 3.72 (s, 2H); 3.40 (s, 2H); 2.85 (s, 4H).

Compound 72
G is —CH$_2$CON(CH$_3$)$_2$

4'-Trifluoromethylbiphenyl-2-carboxylic acid-(2-dimethylcarbamoylmethyl-1,2,3,4-tetrahydroisoquinolin-6-yl)-amide MS (Cl): 482 (M+H$^+$)
$^1$H NMR (300 MHz, CDCl$_3$) δ3.65 (s, 2H); 3.32 (s, 2H); 3.10 (s, 3H); 2.96 (s, 3H); 2.81 (m, 2H); 2.77 (m, 2H).

Compound 73

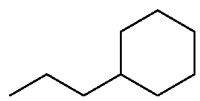

G is

4'-Trifluoromethylbiphenyl-2-carboxylic acid-[2-(2-cyclohexylethyl)-1,2,3,4-tetrahydroisoquinolin-6-yl]-amide MS (Cl): 507 (M+H$^+$)
$^1$H NMR (250 MHz, DMSO) δ3.44 (s, 2H).

Compound 74
G is —(CH$_2$)$_2$CN

4'-Trifluoromethylbiphenyl-2-carboxylic acid-[2-(2-cyanoethyl)1,2,3,4-tetrahydroisoquinolin-6-yl]-amide Compound (II) (780 mg, 1.97 mmole), 3-bromopropionitrile (290 mg, 2.17 mmole) and 4-dimethylaminopyridine (264 mg, 2.16 mmole) were combined in 10 mL of DMF and heated to 70° C. for 72 hrs. The reaction was diluted with methylene chloride, washed with water and brine, and then dried over magnesium sulfate. Purification of the residue obtained on evaporation was carried out with silica gel chromatography using a gradient of 10–100% ethyl acetate in hexane as the eluent.

MS (Cl): 450 (M+H$^+$)

Compound 75

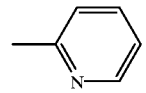

G is

4'-Trifluoromethylbiphenyl-2-carboxylic acid-(2-pyridin-2-yl)-1,2,3,4-tetrahydroisoquinolin-6-yl)-amide Compound (II) (0.20 g, 0.50 mmole), 2-bromopyridine (0.16 g, 1.0 mmole) and potassium carbonate (0.14 g, 1.0 mmole) were combined in 5 mL of chlorobenzene and the resulting mixture was heated to reflux for 48 hrs. The solvent was removed under vacuum and the residue was purified via silica gel chromatography using 50% ethyl acetate in hexane as the eluent MS (Cl): 474 (M+H$^+$)
$^1$H NMR (250 MHz, CDCl$_3$) δ4.63 (s, 2H); 3.79 (t, 2H); 2.89 (t, 2H).

EXAMPLE 8

Compounds 76 and 77

The following compounds were produced by the procedure of Method D described hereinabove. The following synthesis is exemplary of the procedure of Method D.

Compound 76

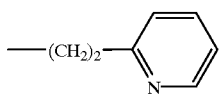

G is

4'-Trifluoromethylbiphenyl-2-carboxylic acid-[2-(2-pyridin-2-yl-ethyl)-1,2,3,4-tetrahydroisoquinolin-6-yl]-amide Compound (II) (300 mg, 0.76 mmole), 2-vinylpyridine (95 mg, 0.91 mmole) and glacial acetic acid (24 mg, 0.40 mmole) were combined in 15 mL of methanol and heated to reflux for 24 hrs. The solvent was removed under vacuum and the residue was purified using silica gel chromatography with a gradient of 0 to 3% methanol in ethyl acetate as the eluent.

MS (Cl): 502 (M+H$^+$)

$^1$H NMR (250 MHz, CDCl$_3$) δ3.67 (s, 2H); 3.09 (m, 2H); 2.92 (m, 2H); 2.80 (m, 4H).

The following compound was synthesized in a manner analogous to that described hereinabove for Compound 76.

Compound 77
G is —(CH$_2$)$_2$CON(CH$_3$)$_2$

4'-Trifluoromethylbiphenyl-2-carboxylic acid-[2-(2-dimethylcarbamoylethyl)-1,2,3,4-tetrahydroisoquinolin-6-yl]-amide MS (Cl): 496 (M+H$^+$)

$^1$H NMR (250 MHz, DMSO) δ3.50 (s, 2H); 2.98 (s, 3H); 2.80 (s, 3H).

EXAMPLE 9

Compounds 78–87

The following compounds were produced by the procedure of Method E described hereinabove. The following synthesis is exemplary of the procedure of Method E.

Compound 78

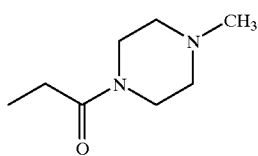

G is

4'-Trifluoromethylbiphenyl-2-carboxylic acid-{2-[2-(4-methylpiperazin-1-yl)-2-oxoethyl]-1,2,3,4-tetrahydroisoquinolin-6-yl}-amide Compound 70 of Example 7 (60 mg, 0.13 mmole), 1-methylpiperazine (22 μL, 0.20 mmole) and 1-(3-dimethylaminopropyl-3-ethylcarbodiimide hydrochloride (28 mg, 0.15 mmole) were combined in 4 mL of anhydrous methylene chloride and stirred at ambient temperature for 15 hrs. The reaction was diluted with methylene chloride and washed with 1 N NaOH followed by brine and then dried over sodium sulfate. The organic layer was evaporated under vacuum and the residue was purified by silica gel column chromatography using a gradient of 1 to 8% methanol in methylene chloride as the eluent.

MS (Cl): 537 (M+H$^+$)

The following compounds were synthesized in a manner analogous to that described hereinabove for Compound 78.

Compound 79

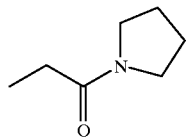

G is

4'-Trifluoromethylbiphenyl-2-carboxylic acid-[2-(2-oxo-2-pyrrolidin-1-ylethyl)-1,2,3,4-tetrahydroisoquinolin-6-yl-amide MS (Cl): 508 (M+H$^+$)

$^1$H NMR (300 MHz, CDCl$_3$) δ3.67 (s, 2H); 3.50 (s, 4H); 3.28 (s, 2H); 2.81 (m, 4H); 1.88 (m, 4H).

Compound 80

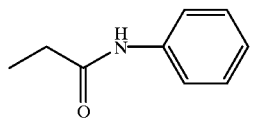

G is

4'-Trifluoromethylbiphenyl-2-carboxylic acid-(2-phenylcarbamoylmethyl-1,2,3,4-tetrahydroisquinolin-6-yl)-amide MS (Cl): 530 (M+H$^+$)

$^1$H NMR (300 MHz, CDCl$_3$) δ3.77 (s, 2H); 3.29 (s, 2H); 2.88 (m, 4H).

Compound 81
G is —CH$_2$CONHCH$_3$

4'-Trifluoromethylbiphenyl-2-carboxylic acid-(2-methylcarbamoylmethyl-1,2,3,4-tetrahydroisoquinolin-6-yl)-amide MS (Cl): 468 (M+H$^+$)

$^1$H NMR (250 MHz, DMSO) δ3.54 (s, 2H); 3.05 (s, 2H); 2.79 (m, 2H); 2.66 (m, 2H); 2.61 (d, 3H).

Compound 82
G is —CH$_2$CON(CH$_2$CH$_3$)$_2$

4'-Trifluoromethylbiphenyl-2-carboxylic acid-(2diethylcarbamoylmethyl -1,2,3,4-tetrahydoisoquinolin-6-yl)-amide MS (Cl): 510 (M+H$^+$)

Compound 83

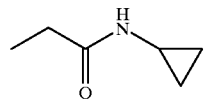

G is

4'-Trifluoromethylbiphenyl-2-carboxylic acid-(2-cyclopropylcarbamoylmethyl-1,2,3,4-tetrahydroisoquinolin-6-yl)-amide MS (Cl): 494 (M+H$^+$)

$^1$H NMR (250 MHz, DMSO) δ3.53 (s, 2H).

Compound 84

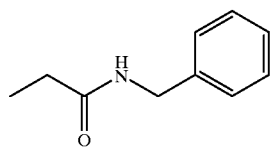

G is

4'-Trifluoromethylbiphenyl-2-carboxylic acid-[2-(benzylcarbamoylmethyl)-1,2,3,4-tetrahydroisoquinolin-6-yl]-amide MS (Cl): 544 (M+H$^+$)

$^1$H NMR (250 MHz, DMSO) δ4.30 (d, 2H); 3.58 (s, 2H); 3.14 (s, 2H); 2.78 (m, 2H); 2.68 (m, 2H).

Compound 85

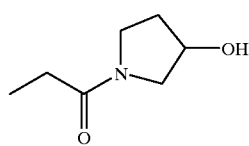

G is

4'-Trifluoromethylbiphenyl-2-carboxylic acid-{2-[2-(3-hydroxypyrrolidin-1-yl)-2-oxoethyl]-1,2,3,4-tetrahydroisoquinolin-6-yl}-amide MS (Cl): 524 (M+H$^+$)

Compound 86

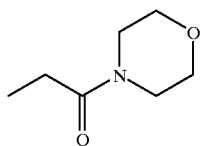

G is

4'-Trifluoromethylbiphenyl-2-carboxylic acid-[2-(2-morpholin-4-yl-2-oxoethyl)-1,2,3,4-tetrahydroisoquinolin-6-yl]-amide MS (Cl): 524 (M+H$^+$)

Compound 87

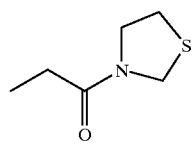

G is

4'-Trifluoromethylbiphenyl-2-carboxylic acid-[2-(2-oxo-2-thiazolidin-3-yl-ethyl)-1,2,3,4-tetrahydroisoquinolin-6-yl]-amide MS (Cl): 526 (M+H$^+$)

EXAMPLE 10

Compounds (II') and 88

The following compounds were produced by the procedure of Method F described hereinabove. For purposes of illustration, a preparation of carbonyl compound (II') is also included.

Compound (II')

4'-Trifluoromethylbiphenyl-2-carboxylic acid-[2-(thiophen-2-yl-acetyl)-1,2,3,4-tetrahydroisoquinolin-6-yl]-amide Compound (II) (3.1 g, 7.8 mmole), 2-thiopheneacetic acid (1.14 g, 8.0 mmole) and 1-(3-dimethylaminopropyl)-3-ethylcarbodiimide hydrochloride (1.7 g, 8.8 mmole) were stirred in 50 mL of methylene chloride for 12 hrs. at ambient temperature. The reaction was diluted with methylene chloride, washed with 1N hydrochloric acid, 1N NaOH, water and brine. Purification of the residue obtained on evaporation was accomplished with silica gel chromatography using 50% ethyl acetate in hexanes as the eluent to yield 3.6 g of the title compound as a solid.

Compound 88

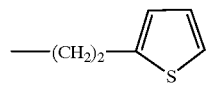

G is

4'-Trifluoromethylbiphenyl-2-carboxylic acid-[2-(2-thiophen-2-yl-ethyl)-1,2,3,4-tetrahydroisoquinolin-6-yl]-amide A 200 mg (0.38 mmole) sample of compound (II') and sodium borohydride (45 mg, 1.2 mmole) were combined in 1 mL of pyridine and the mixture was heated to reflux for 18 hrs. The pyridine was removed under vacuum and the residue was mixed with 10% hydrochloric acid for 20 hrs. at 50° C. The reaction was rendered basic (pH>12) and was extracted with methylene chloride. The organic layer was washed with water and brine and then dried over potassium carbonate. Purification of the residue obtained on evaporation was accomplished with silica gel chromatography using 0.5% methanol in methylene chloride as the eluent MS (Cl): 507 (M+H$^+$)

$^1$H NMR (250 MHz, CDCl$_3$) δ3.65 (s, 2H); 3.11 (t, 2H); 2.79 (m, 6H).

EXAMPLE 11

Compounds 89–93

The following compounds were produced by the procedure of Method G described hereinabove. The following synthesis is exemplary of the procedure of Method G.

Compound 89

G is —(CH$_2$)$_2$OCOCH$_3$

Acetic acid 2-{6-[(4'-trifluoromethylbiphenyl-2carbonyl)-amino]-3,4-dihydro-1H-isoquinolin-2-yl}-ethyl ester Acetyl chloride (100 mg, 1.25 mmole) and 4-dimethylaminopyridine (700 mg, 5.7 mmole) were combined in 5 mL of toluene and the mixture was cooled to 0° C. in an ice bath. To this mixture was added a solution of Compound 67 from Example 6 (500 mg, 1.14 mmole) in 3 mL of methylene chloride. The reaction was allowed to warm to ambient temperature and was stirred under a nitrogen atmosphere for 2 hrs. The reaction was washed with 1 N hydrochloric acid, saturated sodium bicarbonate, and brine and then dried over magnesium sulfate. Purification of the residue obtained on evaporation was accomplished with silica gel chromatography using 3% methanol in ethyl acetate as the eluent.

MS (Cl): 483 (M+H+)
$^1$H NMR (400 MHz, DMSO) δ4.25 (dd, 2H); 3.62 (s, 2H); 2.78 (m, 6H); 2.06 (s, 3H).

The following compounds were synthesized in a manner analogous to that described hereinabove for Compound 89.
Compound 90
G is —(CH$_2$)$_2$OCOC(CH$_3$)$_3$ 2,2-Dimethylpropionic acid 2-{6-[(4'-trifluoromethylbiphenyl-2-carbonyl)-amino}3,4-dihydro-1H-isoquinolin-2-yl}-ethyl ester MS (Cl): 525 (M+H+)
$^1$H NMR (250 MHz, DMSO) δ4.25 (dd, 2H); 3.63 (s, 2H); 2.77 (dd, 6H); 1.19 (s, 9H).
Compound 91
G is —(CH$_2$)$_2$OCON(CH$_3$)$_2$ Dimethylcarbamic acid 2-{6-[4'-trifluoromethylbiphenyl-2-carbonyl)-amino]-3,4-dihydro-1H -isoquinolin-2-yl}-ethyl ester MS (Cl): 512 (M+H+)
$^1$H NMR (400 MHz, CDCl$_3$) δ4.26 (t, 2H); 3.69 (t, 2H); 3.64 (s, 3H); 2.90 (s, 3H); 2.79 (m, 4H); 2.70 (t, 2H).
Compound 92
G is —(CH$_2$)$_2$OCOOCH$_3$ Carbonic acid methyl ester 2-{6-[(4'-trifluoromethylbiphenyl-2-carbonyl}-amino]-3,4-dihydro-1H-isoquinolin-2-}-ethyl ester MS (Cl): 499 (M+H+)
$^1$H NMR (400 MHz, CDCl$_3$) δ4.32 (t, 2H); 3.77 (s, 3H); 3.63 (s, 2H); 2.79 (m, 6H).
Compound 93

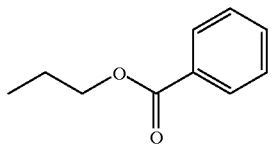

G is

Benzoic acid 2-{6-[(4'-trifluoromethylbiphenyl-2-carbonyl)-amino]-3,4-dihydro-1H-isoquinolin -2-yl}-ethyl ester MS (Cl): 545 (M+H+)
$^1$H NMR (400 MHz, CDCl$_3$) δ4.52 (t, 2H); 3.70 s, 2H); 2.93 (t, 2H); 2.83 (s, 4H).

EXAMPLE 12

Compounds 94–105
The following compounds were produced by the procedure of Method H described hereinabove.
Compound 94

4'-Trifluoromethylbiphenyl-2-carboxylic acid-[2-(2-aminoethyl)-1,2,3,4-tetrahydroisoquinolin-6-yl]-amide An 8.00 g (16.6 mmole) sample of Compound 49 from Example 6 was refluxed in 100 mL of 2N hydrochloric acid for 24 hrs. The reaction was rendered basic with 1 N NaOH and the mixture was extracted with ethyl acetate. The residue obtained upon evaporation was purified by silica gel chromatography using a gradient of 0–10% methanol in methylene chloride with 1% ammonium hydroxide as the eluent to furnish 3.5 of the title compound.

MS (Cl): 440 (M+H+)
$^1$H NMR (250 MHz, CDCl$_3$) δ3.58 (s, 2H); 2.84 (m, 4H); 2.70 (t, 2H); 2.58 (t, 2H).
Compound 95
G is —(CH$_2$)$_2$NHS(O)$_2$CH$_3$ 4'-Trifluoromethylbiphenyl-2-carboxylic acid-[2-(2-methanesulfonylaminoethyl)-1,2,3,4-tetrahydoisoquinolin-6-yl]-amide To a 5 mL solution of Compound 94 (250 mg, 0.57 mmole) in methylene chloride previously cooled to 0° C. was added methanesulfonyl chloride (65 mg, 0.57 mmole). The reaction was warned to ambient temperature and stirred for 12 hrs. The reaction was washed with saturated sodium bicarbonate, extracted with ethyl acetate and dried over magnesium sulfate. Purification of the residue obtained upon evaporation was accomplished with silica gel chromatography using 10% methanol in methylene chloride with 1% ammonium hydroxide as the eluent.

MS (Cl): 518 (M+H+)
$^1$H NMR (400 MHz, CDCl$_3$) δ3.62 (s, 2H); 3.29 (m, 2H); 2.95 (s, 3H); 2.77 (m, 6H).

The following compounds were synthesized in a manner analogous to that described hereinabove for Compound 95.
Compound 96
G is —(CH$_2$)$_2$NHCOCH$_2$CH$_3$ 4'-Trifluoromethylbiphenyl-2-carboxylic acid-[2-(2-propionylaminoethyl)1,2,3,4-tetrahydroisoquinolin-6-yl]-amide MS (Cl): 496 (M+H+)
$^1$H NMR (400 MHz, DMSO) δ3.70 (s, 2H); 3.42 (dd, 2H); 2.82 (t, 2H); 2.72 (t, 2H); 2.64 (t, 2H); 2.17 (q, 2H); 1.12 (t, 3H).
Compound 97
G is —(CH$_2$)$_2$NHCON(CH$_3$)$_2$ 4-Trifluoromethylbiphenyl-2-carboxylic acid-{2-[2-(3,3-dimethylureido)-ethyl]-1,2,3,4-tetrahydroisoquinolin-6-yl}-amide MS (Cl): 511 (M+H+) $^1$H NMR (400 MHz, CDCl$_3$) δ3.56 (s, 2H); 3.37 (m, 2H); 2.84 (s, 6H); 2.79 (t, 2H); 2.69 (t, 2H); 2.63 (t, 2H).
Compound 98
G is —(CH$_2$)$_2$NHCOOCH$_3$ (2-{6-[(4'-Trifluoromethylbiphenyl-2-carbonyl)-amino]-3,4-dihydro-1H-isoquinolin-2-yl}-ethyl)-carbamic acid methyl ester MS (Cl): 498 (M+H+)
$^1$H NMR (400 MHz, CDCl$_3$) δ3.64 (s, 3H); 3.55 (s, 2H); 3.34 (m, 2H); 2.80 (t, 2H); 2.69 (t, 2H); 2.61 (t, 2H).
Compound 99
G is —(CH$_2$)$_2$NHCOC(CH$_3$)$_3$ 4'-Trifluoromethylbiphenyl-2-carboxylic acid-{2-[2-(2,2-dimethylpropionylamino)-ethyl]-1,2,3,4-tetrahydroisoquinolin-6-yl}-amide MS (Cl): 524 (M+H+)
$^1$H NMR (400 MHz, CDCl$_3$) δ3.57 (s, 2H); 3.39 (m, 2H); 2.80 (t, 2H); 2.70 (t, 2H); 2.63 (t, 2H); 1.98 (s, 9H).

Compound 100

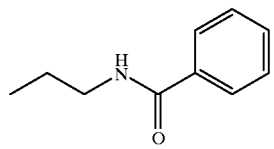

G is

4'-Trifluoromethylbiphenyl-2-carboxylic acid-[2-(2-benzoylaminoethyl)-1,2,3,4-tetrahydroisoquinolin-6-yl]-amide MS (Cl): 544 (M+H$^+$)

$^1$H NMR (400 MHz, CDCl$_3$) δ3.62 (m, 4H); 2.84 (m, 2H); 2.75 (m, 4H).

The following compounds were also synthesized according to the procedure for Compound 95, except the corresponding acid anydride was substituted for the acid halide.

Compound 101
G is —(CH$_2$)$_2$NHS(O)$_2$CF$_3$

4'-Trifluoromethylbiphenyl-2-carboxylic acid-[2-(2-trifluoromethanesulfonylaminoethyl)-1,2,3,4-tetrahydroisoquinolin-6-yl]-amide MS (Cl): 572 (M+H$^+$)

$^1$H NMR (400 MHz, CDCl$_3$) δ3.77 (s, 2H); 3.51 (t, 2H); 2.88 (m, 6H).

Compound 102
G is —(CH$_2$)$_2$NHCOCF$_3$

4'-Trifluoromethylbiphenyl-2-carboxylic acid-{2-[2-(2,2,2-trifluoroacetylamino)-ethyl]-1,2,3,4-tetrahydroisoquinolin-6-yl}-amide MS (Cl): 536 (M+H$^+$)

$^1$H NMR (400 MHz, CDCl$_3$) δ3.61 (s, 2H); 3.51 (dd, 2H); 2.82 (t, 2H); 2.73 (m, 4H).

Compound 103
G is —(CH$_2$)$_2$NHCHO

4'-Trifluoromethylbiphenyl-2-carboxylic acid-[2-(2-formylaminoethyl)-1,2,3,4-tetrahydroisoquinolin-6-yl]-amide Compound 94 (250 mg, 0.57 mmole) was combined with formic acid (66 mg, 1.4 mmole) and heated to reflux for 30 min. Purification of the residue obtained on evaporation was accomplished with silica gel chromatography using 10% methanol in methylene chloride with 1% ammonium hydroxide as the eluent MS (Cl): 468 (M+H$^+$)

$^1$H NMR (400 MHz, CDCl$_3$) δ3.59 (s, 2H); 3.48 (m, 2H); 2.83 (m, 2H); 2.74 2H); 2.67 (t, 2H).

Compound 104
G is —(CH$_2$)$_2$NHCONH$_2$

4'-Trifluoromethylbiphenyl-2-carboxylic acid-[2-(2-ureidoethyl)-1,2,3,4-tetrahydroisoquinolin-6-yl]-amide Compound 94 (250 mg, 0.57 mmole) was combined with 1,1'-carbonyldiimidazole in 6 mL of methylene chloride and stirred for 4 hrs. The reaction was cooled to 0° C. in an ice bath and gaseous ammonia was perfused into the solution. The reaction was then stirred at ambient temperture for 12 hrs. Purification of the residue obtained on evaporation was accomplished with silica gel chromatography using 10% methanol in methylene chloride with 1% ammonium hydroxide as the eluent.

MS (Cl): 483 (M+H$^+$)

$^1$H NMR (400 MHz, CDCl$_3$) δ3.62 (m, 1H); 3.58 (s, 2H); 3.35 (m, 1H); 2.82 (m, 2H); 2.76 (m, 2H); 2.65 (m, 2H).

The following compound was synthesized in a manner analogous to that described for Compound 104.

Compound 105
G is —(CH$_2$)$_2$NHCONHCH$_3$

4'-Trifluoromethylbiphenyl-2-carboxylic acid-{2-[2-(3-methylureido)-ethyl]-1,2,3,4-tetrahydroisoquinolin-6-yl}-amide MS (Cl): 497 (M+H$^+$)

$^1$H NMR (400 MHz, CDCl$_3$) δ3.59 (s, 2H); 3.35 (s, 2H); 2.82 (m, 2H); 2.74 (t, 2H); 2.70 (s, 3H); 2.65 (t, 2H).

EXAMPLE 13

Compounds 106–110

The following compounds were produced by the procedure of Method I described hereinabove.

Compound 106

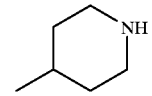

4'-Trifluoromethylbiphenyl-2-carboxylic acid-(2-piperidin-4-yl-1,2,3,4-tetrahydroisoquinolin-6-yl)-amide A 20 g (415 mmole) sample of Compound 61 from Example 6 was combined with palladium hydroxide on carbon (6.1 g) in 260 mL of methanol and 550 mL of THF. Ammonium formate (26 g, 415 mmole) was added and the reaction mixture was heated to 60° C. for 4 hrs. The reaction was filtered and the filter cake was washed with THF followed by methanol. The solution was concentrated and 40 mL of 1N NaOH and 150 mL of water were added. The mixture was stirred for 2 hrs. and filtered to give 15 g of the title compound.

The following compound was synthesized by functionalizing Compound 106 in the reductive amination procedure of Method A.

Compound 107

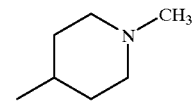

G is

4'-Trifluoromethylbiphenyl-2-carboxylic acid-[2-(1-methylpiperidine-4-yl)-1,2,3,4-tetrahydroisoquinolin-6-yl]-amide MS (Cl): 494 (M+H$^+$)

$^1$H NMR (250 MHz, CDCl$_3$) δ3.70 (s, 2H); 2.95 (d, 2H); 2.79 (s, 4H); 2.29 (s, 3H).

The following compound was synthesized by functionalizing Compound 106 in the amidation procedure of Method H.

Compound 108

G is

4'-Trifluoromethylbiphenyl-2-carboxylic acid-[2-(1-acetylpiperidin-4-yl)-1,2,3,4-tetrahydroisoquinolin-6-yl]-amide MS (Cl): 522 (M+H$^+$)
$^1$H NMR (250 MHz, CDCl$_3$) δ3.72 (s, 2H); 2.81 (s, 4H); 2.10 (s, 3H).

Compound 109

G is

4'-Trifluoromethylbiphenyl-2-carboxylic acid-[2-(1-trifluoroacetylpiperidin-4-yl)-1,2,3,4-tetrahydroisoquiolin-6-yl]-amide MS (Cl): 576 (M+H$^+$)
$^1$H NMR (250 MHz, CDCl$_3$) δ3.72 (s, 2H); 3.17 (t, 1H); 2.83 (m, 6H).

Compound 110

G is

4'-Trifluoromethylbiphenyl-2-carboxylic acid-2-(1-benzoylpiperidin-4-yl)-1,2,3,4-tetrahydoisoquinolin-6-yl]-amide MS (Cl): 584 (M+H$^+$)
$^1$H NMR (250 MHz, CDCl$_3$) δ3.75 (s, 2H); 2.83 (s, 6H).

EXAMPLE 14

Compound 111

The following compound was synthesized by the procedure of Method J described hereinabove. Compound 111

G is

4'-Trifluoromethylbiphenyl-2-carboxylic acid-{2-[2-(2H-[1,2,4-]triazol-3-yl)ethyl]-1,2,3,4-tetrahydroisoquinolin6-yl}-amide A 300 mg (0.67 mmole) sample of Compound 74 and sodium methoxide (3.6 mg, 0.067 mmole) were combined in 2 mL of methanol and stirred at ambient temperature for 5 hrs. Formic hydrazine (40 mg, 0.67 mmole) in 1 mL of methanol was added and the reaction was stirred at ambient temperature for 12 hrs., followed by reflux for 48 hrs. The reaction was concentrated and diluted with chloroform. The organic layer was washed with saturated sodium bicarbonate, brine and dried over sodium sulfate. Purification was accomplished with silica gel chromatography using a gradient of 2–16% ethanol in chloroform as the eluent MS (Cl): 492 (M+H$^+$)

We claim:

1. A compound of the formula or the stereoisomers, pharmaceutically acceptable salts and hydrates thereof, wherein G is selected from:

(a) a phenyl or heterocyclic ring wherein said heterocyclic ring contains a total of from 3 to 14 ring atoms, wherein said heterocyclic ring incorporates a total of from 1 to 4 ring heteroatoms selected independently from oxygen, nitrogen, and sulfur, wherein the individual rings of said heterocyclic ring may be independently saturated, partially saturated or aromatic, and wherein each of said phenyl or heterocyclic rings may have optionally from 1 to 4 substituents selected independently from halogen, hydroxy, cyano, nitro, oxo, thioxo, aminosulfonyl, phenyl, phenoxy, phenylthio, benzyl, benzoyl, benzyloxy, (C$_1$–C$_{10}$)alkyl, (C$_1$–C$_4$) perfluoroalkyl, (C$_1$–C$_{10}$)alkoxy, (C$_1$–C$_4$) perfluoroalkoxy, (C$_1$–C$_{10}$)alkoxycarbonyl, (C$_1$–C$_{10}$) alkylthio, (C$_1$–C$_{10}$)alkylamino, di(C$_1$–C$_{10}$)alkylamino, (C$_1$–C$_{10}$)alkylaminocarbonyl, di(C$_1$–C$_{10}$) alkylaminocarbonyl, (C$_1$–C$_{10}$)acyl, (C$_1$–C$_{10}$) perfluoroacyl, (C$_1$–C$_{10}$)acyloxy, (C$_1$–C$_6$)acylamino and (C$_1$–C$_6$)perfluoroacylamino;

(b) —CH$_2$CN, (c) —CH(phenyl)$_2$ (d) (C$_2$–C$_{12}$)alkyl or (C$_2$–C$_{12}$)perfluoroalkyl wherein each of said (C$_2$–C$_{12}$)alkyl and (C$_2$–C$_{12}$)perfluoroalkyl is substituted optionally with from 1–3 substituents selected independently from:

(1) phenyl, halogen, nitro, cyano, hydroxy, —NR$^1$R$^2$, —OCOR$^3$, (C$_1$–C$_4$)alkoxy, (C$_1$–C$_4$)perfluoroalkoxy, (C$_1$–C$_4$)thioalkoxy or (C$_1$–C$_4$)perfluorothioalkoxy,
where R$^1$ and R$^2$ in the definition of —NR$^1$R$^2$ are each selected independently from hydrogen, formyl, phenyl, benzyl, benzoyl, $(C_3-C_8)$cycloalkyl, $(C_3-C_8)$cycloalkenyl, $(C_1-C_4)$alkyl, $(C_1-C_4)$perfluoroalkyl, $(C_1-C_{10})$alkoxycarbonyl, $(C_1-C_6)$acyl, $(C_1-C_6)$perfluoroacyl, aminocarbonyl, $(C_1-C_{10})$alkylaminocarbonyl, di$(C_1-C_{10})$alkylaminocarbonyl, aminosulfonyl, $(C_1-C_4)$alkylaminosulfonyl, di$(C_1-C_4)$alkylaminosulfonyl, $(C_1-C_4)$perfluoroalkylaminosulfonyl, $(C_1-C_4)$perfluoroalkylaminosulfonyl, $(C_1-C_4)$alkylsulfonyl, and$(C_1-C_4)$perfluoroalkylsulfonyl, or where $R^1$ and $R^2$, taken together with the nitrogen atom to which they are attached, form a saturated, partially-saturated or aromatic heterocyclic ring, wherein said heterocyclic ring contains a total of from 3 to 14 ring atoms and incorporates optionally an additional 1 to 4 ring heteroatoms selected independently from oxygen, nitrogen and sulfur, wherein said heterocyclic ring may have optionally from 1 to 4 substituents selected independently from halogen, hydroxy, cyano, nitro, oxo, thioxo, aminosulfonyl, phenyl, phenoxy, phenylthio, benzyl, benzoyl, benzyloxy, $(C_1-C_{10})$alkyl, $(C_1-C_4)$perfluoroalkyl, $(C_1-C_{10})$alkoxy, $(C_1-C_4)$perfluoroalkoxy, $(C_1-C_{10})$alkoxycarbonyl, $(C_1-C_{10})$alkylthio, $(C_1-C_{10})$alkylamino, di$(C_1-C_{10})$alkylamino, $(C_1-C_{10})$alkylaminocarbonyl, di$(C_1-C_{10})$alkylaminocarbonyl, $(C_1-C_{10})$acyl, $(C_1-C_{10})$perfluoroacyl, $(C_1-C_{10})$acylamino, and $(C_1-C_{10})$acyloxy, where $R^3$ in the definition of —OCOR$^3$ is selected from —NR$^1$R$^2$, phenyl, $(C_1-C_{10})$alkyl, $(C_1-C_4)$perfluoroalkyl, $(C_1-C_6)$alkoxy and $(C_1-C_6)$perfluoroalkoxy, (2) $(C_3-C_8)$cycloalkyl or $(C_3-C_8)$cycloalkenyl wherein each of said $(C_3-C_8)$cycloalkyl and $(C_3-C_8)$cycloalkenyl may have optionally from 1 to 4 substituents selected independently from halogen, hydroxy, cyano, nitro, oxo, thioxo, aminosulfonyl, phenyl, phenoxy, phenylthio, benzyl, benzoyl, benzyloxy, $(C_1-C_{10})$alkyl, $(C_1-C_4)$perfluoroalkyl, $(C_1-C_{10})$alkoxy, $(C_1-C_4)$perfluoroalkoxy, $(C_1-C_{10})$alkoxycarbonyl, $(C_1-C_{10})$alkylthio, $(C_1-C_{10})$alkylamino, di$(C_1-C_{10})$alkylamino, $(C_1-C_{10})$alkylaminocarbonyl, di$(C_1-C_{10})$alkylaminocarbonyl, $(C_1-C_{10})$acyl, $(C_1-C_{10})$perfluoroacyl, $(C_1-C_{10})$acylamino, $(C_1-C_{10})$perfluoroacylamino, $(C_1-C_{10})$acyloxy, and (3) a saturated, partially-saturated or aromatic heterocyclic ring containing a total of from 3 to 14 ring atoms, wherein said heterocyclic ring incorporates a total of from 1 to 4 ring heteroatoms selected independently from oxygen, nitrogen and sulfur, wherein said heterocyclic ring may have optionally from 1 to 4 substituents selected independently from halogen, hydroxy, cyano, nitro, oxo, thioxo, aminosulfonyl, phenyl, phenoxy, phenylthio, benzyl, benzoyl, benzyloxy, $(C_1-C_{10})$alkyl, $(C_1-C_4)$perfluoroalkyl, $(C_1-C_{10})$alkoxy, $(C_1-C_4)$perfluoroalkoxy, $(C_1-C_{10})$alkoxycarbonyl, $(C_1-C_{10})$alkylthio, $(C_1-C_{10})$alkylamino, di$(C_1-C_{10})$alkylamino, $(C_1-C_{10})$alkylaminocarbonyl, di$(C_1-C_{10})$alkylaminocarbonyl, $(C_1-C_{10})$acyl, $(C_1-C_{10})$perfluoroacyl, $(C_1-C_{10})$acylamino, $(C_1-C_{10})$perfluoroacylamino, $(C_1-C_{10})$acyloxy, provided that $(C_2-C_{12})$alkyl does not include unsubstituted allyl;

(e) $(C_3-C_8)$cycloalkyl or $(C_3-C_8)$cycloalkenyl wherein each of said $(C_3-C_8)$cycloalkyl and $(C_3-C_8)$cycloalkenyl may have optionally from 1 to 4 substituents selected independently from halogen, hydroxy, cyano, nitro, oxo, thioxo, aminosulfonyl, phenyl, phenoxy, phenylthio, benzyl, benzoyl, benzyloxy, $(C_1-C_{10})$alkyl, $(C_1-C_4)$perfluoroalkyl, $(C_1-C_{10})$alkoxy, $(C_1-C_4)$perfluoroalkoxy, $(C_1-C_{10})$alkoxycarbonyl, $(C_1-C_{10})$alkylthio, $(C_1-C_{10})$alkylamino, di$(C_1-C_{10})$alkylamino, $(C_1-C_{10})$alkylaminocarbonyl, di$(C_1-C_{10})$alkylaminocarbonyl, $(C_1-C_{10})$acyl, $(C_1-C_{10})$perfluoroacyl, $(C_1-C_{10})$acylamino, $(C_1-C_{10})$perfluoroacylamino, $(C_1-C_{10})$acyloxy; and (f) —$(CH_2)_n COR^4$ where $R^4$ in the definition of —$(CH_2)_n COR^4$ is selected from hydroxy, phenyl, —NR$^1$R$^2$, $(C_1-C_4)$alkyl, $(C_1-C_4)$perfluoroalkyl, $(C_1-C_4)$alkoxy, $(C_1-C_4)$perfluoroalkoxy, $(C_3-C_8)$cycloalkyl, and $(C_3-C_8)$cycloalkenyl, where n is an integer from 1 to 4.

2. A compound as claimed in claim 1 and the stereoisomers, pharmaceutically acceptable salts and hydrates thereof, wherein G is selected from:

(a) a phenyl or heterocyclic ring wherein said heterocyclic ring contains a total of from 3 to 7 ring atoms, wherein said heterocyclic ring incorporates a total of from 1 to 4 ring heteroatoms selected independently from oxygen, nitrogen, and sulfur, wherein said heterocyclic ring may be saturated, partially saturated or aromatic, and wherein each of said phenyl or heterocyclic rings may each have optionally from 1 to 4 substituents selected independently from halogen, hydroxy, phenyl, benzyl, benzoyl, benzyloxy, $(C_1-C_{10})$alkyl, $(C_1-C_4)$perfluoroalkyl, $(C_1-C_{10})$alkoxy, $(C_1-C_4)$perfluoroalkoxy, $(C_1-C_{10})$alkoxycarbonyl, $(C_1-C_{10})$alkylthio, $(C_1-C_{10})$alkylamino, di$(C_1-C_{10})$alkylamino, $(C_1-C_{10})$alkylaminocarbonyl, di$(C_1-C_{10})$alkylaminocarbonyl, $(C_1-C_{10})$acyl, $(C_1-C_{10})$perfluoroacyl, $(C_1-C_6)$acylamino, $(C_1-C_6)$perfluoroacylamino, $(C_1-C_{10})$acyloxy;

(b) $(C_2-C_{12})$alkyl wherein said $(C_2-C_{12})$alkyl is substituted optionally with from 1–3 substituents selected independently from:

(1) phenyl, halogen, cyano, hydroxy, —NR$^1$R$^2$, —OCOR$^3$, $(C_1-C_4)$alkoxy, or $(C_1-C_4)$perfluoroalkoxy, where $R^3$ in the definition of —OCOR$^3$ is selected from —NR$^1$R$^2$, $(C_1-C_4)$alkyl and $(C_1-C_4)$perfluoroalkyl, (2) $(C_3-C_6)$cycloalkyl or $(C_3-C_6)$cycloalkenyl wherein each of said $(C_3-C_6)$cycloalkyl and $(C_3-C_6)$cycloalkenyl may optionally have from 1 to 4 substituents selected independently from hydroxy, $(C_1-C_4)$alkyl, $(C_1-C_4)$alkoxy, and $(C_1-C_4)$alkoxycarbonyl, and (3) a saturated, partially-saturated or aromatic heterocyclic ring containing a total of from 3 to 6 ring atoms, wherein said heterocyclic ring incorporates a total of from 1 to 4 ring heteroatoms selected independently from oxygen, nitrogen and sulfur, wherein said heterocyclic ring may have optionally from 1 to 4 substituents selected independently from halogen, hydroxy, phenyl, benzyl, benzoyl, benzyloxy, $(C_1-C_{10})$alkyl, $(C_1-C_4)$perfluoroalkyl, $(C_1-C_{10})$alkoxy, $(C_1-C_{10})$alkoxycarbonyl, $(C_1-C_{10})$alkylthio, $(C_1-C_{10})$alkylamino, di$(C_1-C_{10})$alkylamino, $(C_1-C_{10})$alkylaminocarbonyl, di$(C_1-C_{10})$alkylaminocarbonyl, $(C_1-C_4)$perfluoroalkoxy, $(C_1-C_{10})$acyl, $(C_1-C_{10})$acylamino, $(C_1-C_{10})$perfluoroacylamino, $(C_1-C_{10})$acyloxy, provided that (C$_2$–C$_{12}$)alkyl does not include unsubstituted allyl;

(c) (C$_3$–C$_6$)cycloalkyl or (C$_3$–C$_6$)cycloalkenyl wherein each of said (C$_3$–C$_6$)cycloalkyl and (C$_3$–C$_6$)cycloalkenyl may have optionally from 1 to 4 substituents selected independently from hydroxy, (C$_1$–C$_4$)alkyl, (C$_1$–C$_4$)alkoxy, (C$_1$–C$_{10}$)acylamino, (C$_1$–C$_{10}$)perfluoroacylamino and (C$_1$–C$_4$)alkoxycarbonyl; and (d) —(CH$_2$)$_n$COR$^4$, where R$^4$ in the definition of —(CH$_2$)$_n$COR$^4$ is selected from hydroxy, phenyl, —NR$^1$R$^2$, (C$_1$–C$_4$)alkyl, (C$_1$–C$_4$)perfluoroalkyl, (C$_1$–C$_4$)alkoxy, (C$_1$–C$_4$)perfluoroalkoxy, (C$_3$–C$_6$)cycloalkyl, and (C$_3$–C$_6$)cycloalkenyl, where n is an integer from 1 to 4.

3. A compound as claimed in claim 2, and the stereoisomers, pharmaceutically acceptable salts and hydrates thereof, wherein G is (C$_2$–C$_{12}$)alkyl, wherein said (C$_2$–C$_{12}$)alkyl is substituted optionally with a group selected from phenyl, halogen, cyano, hydroxy, (C$_1$–C$_4$)alkoxy, or a saturated, partially-saturated or aromatic heterocyclic ring selected from thienyl, pyrazolyl, pyrrolidinyl, pyrrolyl, furanyl, thiazolyl, isoxazolyl, imidazolyl, triazolyl, tetrahydropyranyl, pyridyl, and pyrimidyl, wherein each of said heterocyclic rings may have optionally from 1 to 3 substitutents selected independently from halogen, (C$_1$–C$_4$) acyl, (C$_1$–C$_4$)perfluoroacyl, (C$_1$–C$_4$)alkyl, (C$_1$–C$_4$) perfluoroalkyl, (C$_1$–C$_4$)alkoxy, (C$_1$–C$_4$) alkylaminocarbonyl, and (C$_1$–C$_4$)acylamino, provided that (C$_2$–C$_{12}$)alkyl does not include unsubstituted allyl.

4. A compound as claimed in claim 2, and the stereoisomers, pharmaceutically acceptable salts and hydrates thereof, wherein G is —(CH$_2$)$_n$NR$^1$R$^2$ and n is an integer from 2 to 4.

5. A compound as claimed in claim 2, and the stereoisomers, pharmaceutically acceptable salts and hydrates thereof, wherein G is —(CH$_2$)$_n$COR$^4$ and n is 1 or 2.

6. The compound of claim 2, wherein G is —(CH$_2$)$_2$OCOCH$_3$.

7. The compound of claim 2, wherein G is —(CH$_2$)$_2$OCON(CH$_3$)$_2$.

8. The compound of claim 2, wherein G is

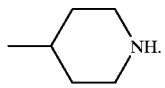

9. The compound of claim 2, wherein G is

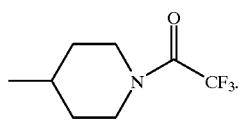

10. The compound of claim 3, wherein G is —(CH$_2$)$_4$CH$_3$.

11. The compound of claim 3, wherein G is —(CH$_2$)$_2$OCH$_3$.

12. The compound of claim 3, wherein G is —(CH$_2$)$_2$OCH$_2$CH$_3$.

13. The compound of claim 3, wherein G is —(CH$_2$)$_3$OCH$_3$.

14. The compound of claim 3, wherein G is —(CH$_2$)$_2$CN.

15. The compound of claim 3, wherein G is

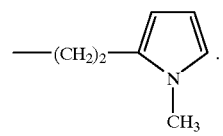

16. The compound of claim 3, wherein G is

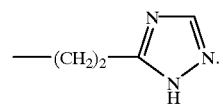

17. The compound of claim 3, wherein G is

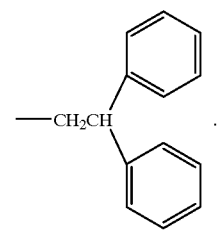

18. The compound of claim 3, wherein G is

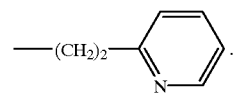

19. The compound of claim 3, wherein G is

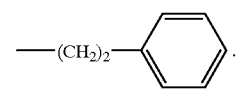

20. The compound of claim 4, wherein G is —(CH$_2$)$_2$NHS(O)$_2$CH$_3$.

21. The compound of claim 4, wherein G is —(CH$_2$)$_2$NHCHO.

22. The compound of claim 4, wherein G is —(CH$_2$)$_2$NHCOCH$_2$CH$_3$.

23. The compound of claim 4, wherein G is —(CH$_2$)$_2$NHCOCF$_3$.

24. The compound of claim 4, wherein G is —(CH$_2$)$_2$NHCONHCH$_3$.

25. The compound of claim 4, wherein G is —(CH$_2$)$_2$NHCOOCH$_3$.

26. The compound of claim 4, wherein G is —(CH$_2$)$_2$NHCOCH$_3$.

27. The compound of claim 4, wherein G is —(CH$_2$)$_2$NH$_2$.

28. The compound of claim 5, wherein G is —CH$_2$CON(CH$_3$)$_2$.

29. The compound of claim 5, wherein G is —CH$_2$CON(CH$_2$CH$_3$)$_2$.

30. The compound of claim 5, wherein G is —(CH$_2$)$_2$CON(CH$_3$)$_2$.

31. The compound of claim 5, wherein G is —CH$_2$COOH.

32. A method for inhibiting or decreasing Apo B secretion in a mammal in need thereof which method comprises the administration of an Apo B secretion inhibiting or decreasing amount of a compound of claim 1 or a stereoisomer, pharmaceutically acceptable salt or hydrate thereof.

33. A method for the treatment of a condition selected from atherosclerosis, pancreatitis, obesity, hypercholesterolemia, hypertriglyceridemia, hyperlipidemia or diabetes which method comprises administering to a mammal in need of such treatment a therapeutically effective amount of a compound of claim 1 or a stereoisomer, pharmaceutically acceptable salt or hydrate thereof.

34. A method as claimed in claim 33 wherein said condition is selected from hypercholesterolemia, hypertriglyceridemia, or hyperlipidemia.

35. A method as claimed in claim 34 wherein said condition is hypercholesterolemia.

36. A method as claimed in claim 34 wherein said condition is hypertriglyceridemia.

37. A method as claimed in claim 34 wherein said condition is hyperlipidemia.

38. A method as claimed in claim 33 wherein said condition is selected from atherosclerosis, obesity, or diabetes.

39. A method as claimed in claim 38 wherein said condition is atherosclerosis.

40. A method as claimed in claim 38 wherein said condition is obesity.

41. A method as claimed in claim 38 wherein said condition is diabetes.

42. A pharmaceutical composition which comprises a therapeutically effective amount of a compound of claim 1 or a stereoisomer, pharmaceutically acceptable salt or hydrate thereof in combination with a pharmaceutically-acceptable carrier or diluent.

43. A pharmaceutical composition for the treatment of a condition selected from atherosclerosis, pancreatitis, obesity, hypercholesterolemia, hypertriglyceridemia, hyperlipidemia or diabetes in a mammal which comprises a therapeutically effective amount of a compound of claim 1 or the stereoisomer, pharmaceutically acceptable salt or hydrate thereof in combination with a pharmaceutically acceptable carrier or diluent.

44. A pharmaceutical composition comprising:
a. a therapeutically effective amount of a first compound, wherein said first compound is a compound of claim 1 or a stereoisomer, pharmaceutically acceptable salt or hydrate thereof;
b. a therapeutically effective amount of a second compound, wherein said second compound is selected from a cholesterol absorption inhibitor, a CETP inhibitor, an HMG-CoA reductase inhibitor, an HMG-CoA synthase inhibitor, an inhibitor of HMG-CoA reductase gene expression, niacin, an antioxidant, an ACAT inhibitor or a squalene synthetase inhibitor; and
c. a pharmaceutically acceptable carrier or diluent.

45. A pharmaceutical composition as claimed in claim 44 wherein said second compound is selected from lovastatin, simvastatin, pravastatin, fluvastatin, atorvastatin or rivastatin.

46. A pharmaceutical composition as claimed in claim 45 wherein said second compound is atorvastatin.

47. A method for the treatment of a condition selected from atherosclerosis, pancreatitis, obesity, hypercholesterolemia, hypertriglyceridemia, hyperlipidemia or diabetes which method comprises administering to a mammal in need of such treatment:

a. a therapeutically effective amount of a first compound, wherein said first compound is a compound of claim 1 or a stereoisomer, pharmaceutically acceptable salt or hydrate thereof; and
b. a therapeutically effective amount of a second compound, wherein said second compound is selected from a cholesterol absorption inhibitor, a CETP inhibitor, an HMG-CoA reductase inhibitor, an HMG-CoA synthase inhibitor, an inhibitor of HMG-CoA reductase gene expression, niacin, an antioxidant, an ACAT inhibitor or a squalene synthetase inhibitor.

48. A method as claimed in claim 47 wherein said second compound is selected from lovastatin, simvastatin, pravastatin, fluvastatin, atorvastatin or rivastatin.

49. A method as claimed in claim 48 wherein said second compound is atorvastatin.

50. A compound as claimed in claim 1, wherein said compound is selected from:

{6[(4'-trifluoromethylbiphenyl-2-carbonyl)-amino]-3,4-dihydro-1H-isoquinolin-2-yl}-acetic acid, 4'-trifluoromethylbiphenyl-2-carboxylic acid-(n-pentyl-1,2,3,4-tetrahydroisoquinolin-6-yl)-amide, 4'-trifluoromethylbiphenyl-2-carboxylic acid-[2-(3-methoxypropyl)-1,2,3,4-tetrahydroisoquinolin-6-yl]-amide, 4'-trifluoromethylbiphenyl-2-carboxylic acid-[2-(2-methoxyethyl)-1,2,3,4-tetrahydroisoquinolin-6-yl]-amide, 4'-trifluoromethylbiphenyl-2-carboxylic acid-[2-(2-ethoxyethyl)-1,2,3,4-tetrahydroisoquinolin-6-yl]-amide, 4'-trifluoromethyl-biphenyl-2-carboxylic acid-[2-(2-cyanoethyl)-1,2,3,4-tetrahydroisoquinolin-6-yl]-amide, acetic acid 2-{6-[(4'-trifluoromethylbiphenyl-2-carbonyl)-amino]-3,4-dihydro-1H-isoquinolin-2-yl}-ethyl ester, and dimethylcarbamic acid 2-{6-[(4'-trifluoromethylbiphenyl-2-carbonyl)-amino]-3,4-dihydro-1H-isoquinolin-2-yl}-ethyl ester.

51. A compound as claimed in claim 1, wherein said compound is selected from:

4'-trifluoromethylbiphenyl-2-carboxylic acid-[2-(2-aminoethyl)-1,2,3,4-tetrahydroisoquinolin-6-yl]-amide 4'-trifluoromethylbiphenyl-2-carboxylic acid-[2-(2-acetylaminoethyl)-1,2,3,4-tetrahydroisoquinolin-6-yl]-amide, 4'-trifluoromethyl-biphenyl-2-carboxylic acid-[2-(2-dimethylcarbamoylethyl)-1,2,3,4-tetrahydroisoquinolin-6-yl]-amide, 4'-trifluoromethylbiphenyl-2-carboxylic acid-(2-dimethylcarbamoylmethyl-1,2,3,4-tetrahydroisoquinolin-6-yl)-amide, 4'-trifluoromethylbiphenyl-2-carboxylic acid-(2-diethylcarbamoylmethyl-1,2,3,4-tetrahydroisoquinolin-6-yl)-amide, 4'-trifluoromethylbiphenyl-2-carboxylic acid-[2-(2-methanesulfonylaminoethyl)-1,2,3,4-tetrahydroisoquinolin-6-yl]-amide, 4'-trifluoromethylbiphenyl-2-carboxylic acid-{2-[2-(2,2,2-trifluoroacetylamino)-ethyl]-1,2,3,4-tetrahydroisoquinolin-6-yl}-amide, 4'-trifluoromethylbiphenyl-2-carboxylic acid-[2-(2-propionylaminoethyl)-1,2,3,4-tetrahydroisoquinolin-6-yl]-amide, (2-{6-[4'-trifluoromethylbiphenyl-2-carbonyl)amino]-3,4-dihydro-1H-isoquinolin-2-yl}-ethyl)-carbamic acid methyl ester, 4'-trifluoromethylbiphenyl-2-carboxylic acid-[2-(2-formylaminoethyl)-1,2,3,4-tetrahydroisoquinolin-6-yl]-amide, and 4'-trifluoromethylbiphenyl-2-carboxylic acid-{2-[2-(3-methylureido)-ethyl]-1,2,3,4-tetrahydroisoquinolin-6-yl}amide.

52. A compound as claimed in claim 1, wherein said compound is selected from:

4'-trifluoromethylbiphenyl-2-carboxylic acid{2-[2-(1-methyl-1H-pyrrol-2-yl)ethyl]-1,2,3,4-tetrahydroisoquinolin-6-yl}amide, 4'-trifluoromethylbiphenyl-2-carboxylic acid-{2-[2-(2H-[1,2,4]triazol-3-yl-ethyl]-1,2,3,4-tetrahydroisoquinolin-6-yl}-amide, 4'-trifluoromethylbiphenyl-2-carboxylic acid-[2-(2,2-diphenylethyl)-1,2,3,4-tetrahydroisoquinolin-6-yl]-amide, 4'-trifluoromethylbiphenyl-2-carboxylic acid-[2-(2-pyridin-2-yl-ethyl)-1,2,3,4-tetrahydroisoquinolin-6-yl]-amide, 4'-trifluoromethylbiphenyl-2-carboxylic acid-(2-phenylethyl-1,2,3,4-tetrahydroisoquinolin-6-yl)-amide, 4'-trifluoromethylbiphenyl-2-carboxylic acid-(2-piperidin-4-yl-1,2,3,4-tetrahydroisoquinolin-6-yl)amide, and 4'-trifluoromethylbiphenyl-2-carboxylic acid-[2-(1-trifluoromethylacetyl-piperidin-4-yl)-1,2,3,4-tetrahydroisoquinolin-6-yl]-amide.

53. A process for the preparation of a compound having the structural formula

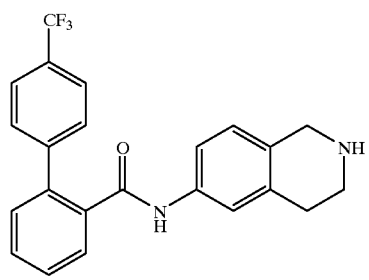

which process comprises the steps of:

(a) cyclizing a diacid of the structural formula

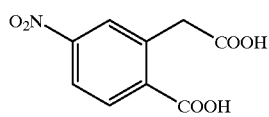

or an activated form thereof, with benzylamine to provide a dione derivative of structural formula

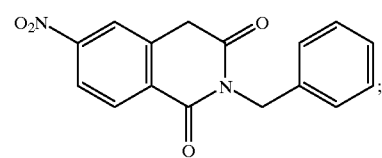

(b) reducing the product of Step (a) to provide an isoquinoline derivative of structural formula

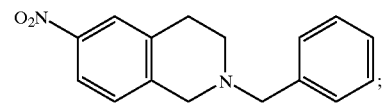

(c) reducing the product of Step (b) to provide an amino derivative of structural formula

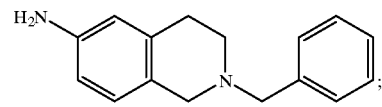

(d) coupling the product of Step (c) with the compound 4'-trifluoromethylbiphenyl-2-carboxylic acid, or an activated form thereof to provide an amide derivative of structural formula

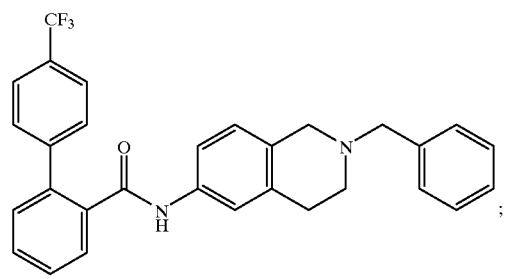

(e) deprotecting the amide derivative of Step (d) to provide said amino derivative of structural formula

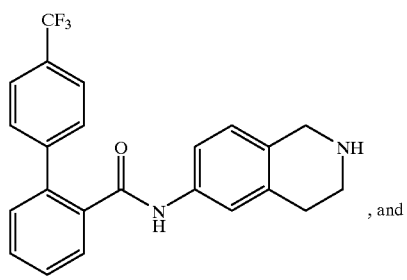

, and (f) isolating the amino derivative of Step (e) in the free base form or an acid addition salt thereof.

54. A process for the preparation of a compound having the structural formula

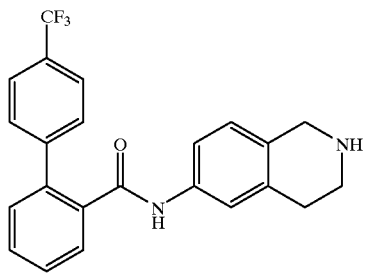

which process comprises the steps of:

(a) deprotecting an amide derivative of the structural formula

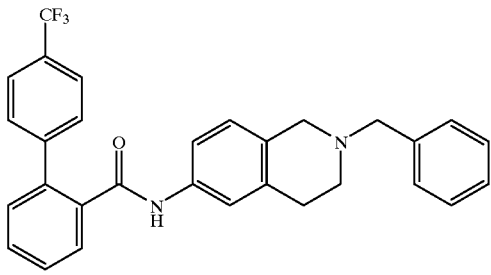

to provide said amino derivative of structural formula

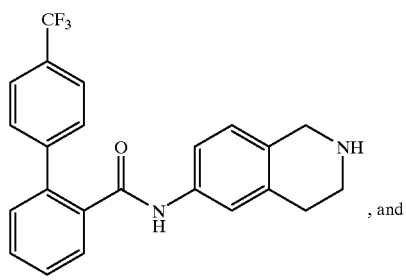, and (b) isolating the amino derivative of Step (a) in the free base form or an add addition salt thereof.

55. The tosylate acid addition salt of the compound

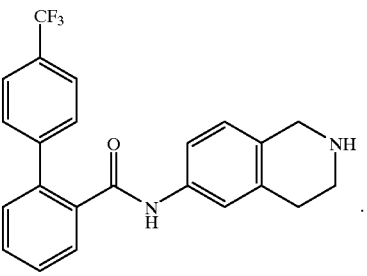

56. A compound having the structural formula

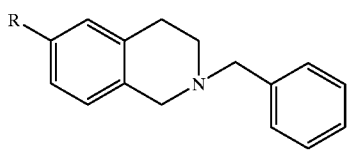

or an acid addition salt thereof, wherein R is selected from —NO$_2$, and —NH$_2$.

* * * * *